(12) United States Patent
Sharma et al.

(10) Patent No.: US 7,968,548 B2
(45) Date of Patent: Jun. 28, 2011

(54) MELANOCORTIN RECEPTOR-SPECIFIC PIPERAZINE COMPOUNDS WITH DIAMINE GROUPS

(75) Inventors: Shubh D. Sharma, Cranbury, NJ (US); Yi-Qun Shi, East Brunswick, NJ (US); Kevin D. Burris, Washington Crossing, PA (US); Zhijun Wu, Plainsboro, NJ (US); Papireddy Purma, Plainsboro, NJ (US); Yadi Reddy Bonuga, Plainsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 612 days.

(21) Appl. No.: 11/464,053

(22) Filed: Aug. 11, 2006

(65) Prior Publication Data
US 2006/0287331 A1    Dec. 21, 2006

Related U.S. Application Data

(60) Provisional application No. 60/707,488, filed on Aug. 11, 2005.

(51) Int. Cl.
*A61K 31/495*    (2006.01)
*C07D 241/04*    (2006.01)

(52) U.S. Cl. .................. 514/252.12; 544/399

(58) Field of Classification Search .......... 514/252.12; 544/399
See application file for complete search history.

(56) References Cited

U.S. PATENT DOCUMENTS

| | | | |
|---|---|---|---|
| 4,148,923 A | 4/1979 | Giudicelli et al. | |
| 4,239,763 A | 12/1980 | Milavec et al. | |
| 4,626,549 A | 12/1986 | Molloy et al. | |
| 4,680,289 A | 7/1987 | Applezweig | |
| 4,711,957 A | 12/1987 | Lai | |
| 4,766,125 A | 8/1988 | Van Daele | |
| 4,937,267 A | 6/1990 | Holloway et al. | |
| 4,938,763 A | 7/1990 | Dunn et al. | |
| 4,943,578 A | 7/1990 | Naylor et al. | |
| 4,968,684 A | 11/1990 | Van Daele et al. | |
| 4,997,836 A | 3/1991 | Sugihara et al. | |
| 5,120,713 A | 6/1992 | Mugica | |
| 5,292,726 A | 3/1994 | Ashton et al. | |
| 5,331,573 A | 7/1994 | Balaji et al. | |
| 5,334,830 A | 8/1994 | Fukuyama et al. | |
| 5,348,955 A | 9/1994 | Greenlee et al. | |
| 5,464,788 A | 11/1995 | Bock et al. | |
| 5,494,919 A | 2/1996 | Morriello et al. | |
| 5,550,131 A | 8/1996 | Sugihara et al. | |
| 5,574,031 A | 11/1996 | Abramo et al. | |
| 5,579,250 A | 11/1996 | Balaji et al. | |
| 5,599,809 A | 2/1997 | Hickey et al. | |
| 5,639,778 A | 6/1997 | Andersson et al. | |
| 5,672,602 A | 9/1997 | Burkholder et al. | |
| 5,721,250 A | 2/1998 | Morriello et al. | |
| 5,721,251 A | 2/1998 | Chen et al. | |
| 5,736,539 A | 4/1998 | Graham et al. | |
| 5,753,445 A | 5/1998 | Fillit et al. | |
| 5,753,653 A | 5/1998 | Bender et al. | |
| 5,763,445 A | 6/1998 | Kruse et al. | |
| 5,798,359 A | 8/1998 | Shue et al. | |
| 5,804,578 A | 9/1998 | Chakravarty et al. | |
| 5,856,326 A | 1/1999 | Anthony et al. | |
| 5,872,262 A | 2/1999 | Dolle et al. | |
| 5,877,182 A | 3/1999 | Nargund et al. | |
| 5,880,125 A | 3/1999 | Nargund | |
| 5,880,128 A | 3/1999 | Doll et al. | |
| 5,891,418 A | 4/1999 | Sharma | |
| 5,892,038 A | 4/1999 | Dolle et al. | |
| 5,936,089 A | 8/1999 | Carpino et al. | |
| 5,965,565 A | 10/1999 | Chen et al. | |
| 5,968,938 A | 10/1999 | Williams et al. | |
| 6,020,334 A | 2/2000 | Fukushi et al. | |
| 6,027,711 A | 2/2000 | Sharma | |
| 6,033,656 A | 3/2000 | Mikami et al. | |

(Continued)

FOREIGN PATENT DOCUMENTS
WO    WO 96/38471    12/1996

(Continued)

OTHER PUBLICATIONS

U.S. Appl. No. 11/110,060, filed Apr. 19, 2005, Sharma et al.

(Continued)

*Primary Examiner* — Joseph R Kosack
(74) *Attorney, Agent, or Firm* — Stephen A. Slusher

(57) ABSTRACT

Melanocortin receptor-specific compounds with diamine groups of the general formula

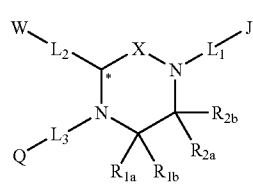

and pharmaceutically acceptable salts thereof, where W is a diamine heteroatom unit with at least one cationic center, hydrogen bond donor or hydrogen bond acceptor, J, Q, $L_1$, $L_2$, $L_3$, $R_{1a}$, $R_{1b}$, $R_{2a}$, $R_{2b}$ and X are as defined in the specification, and the carbon atom marked with an asterisk can have any stereochemical configuration. Compounds disclosed herein bind to one or more melanocortin receptors and may be an agonist, a partial agonist, an antagonist, an inverse agonist or an antagonist of an inverse agonist as to one or more melanocortin receptors, and may be employed for treatment of one or more melanocortin receptor-associated conditions or disorders, including specifically treatment of obesity and related conditions.

16 Claims, No Drawings

U.S. PATENT DOCUMENTS

| | | | |
|---|---|---|---|
| 6,127,381 A | 10/2000 | Basu et al. |
| 6,127,424 A | 10/2000 | Martin et al. |
| 6,140,354 A | 10/2000 | Dax et al. |
| 6,162,805 A | 12/2000 | Hefti |
| 6,191,117 B1 | 2/2001 | Kozachuk |
| 6,207,665 B1 | 3/2001 | Bauman et al. |
| 6,207,699 B1 | 3/2001 | Rothman |
| 6,214,831 B1 | 4/2001 | Yokoo et al. |
| 6,245,764 B1 | 6/2001 | Kahn et al. |
| 6,284,735 B1 | 9/2001 | Girten et al. |
| 6,294,539 B1 | 9/2001 | Lou et al. |
| 6,303,611 B1 | 10/2001 | Zhang et al. |
| 6,316,470 B1 | 11/2001 | Kover et al. |
| 6,331,285 B1 | 12/2001 | Sharma |
| 6,340,868 B1 | 1/2002 | Lys et al. |
| 6,350,760 B1 | 2/2002 | Bakshi et al. |
| 6,372,747 B1 | 4/2002 | Taveras et al. |
| 6,376,509 B1 | 4/2002 | Bakshi et al. |
| 6,410,548 B2 | 6/2002 | Nargund et al. |
| 6,432,438 B1 | 8/2002 | Shukla |
| 6,432,959 B1 | 8/2002 | Cooper et al. |
| 6,451,783 B1 | 9/2002 | Hadcock et al. |
| 6,458,789 B1 | 10/2002 | Forood et al. |
| 6,458,790 B2 | 10/2002 | Palucki et al. |
| 6,469,006 B1 | 10/2002 | Blair et al. |
| 6,472,398 B1 | 10/2002 | Palucki et al. |
| 6,486,165 B2 | 11/2002 | Zhang et al. |
| 6,515,122 B1 | 2/2003 | Lang et al. |
| 6,531,476 B1 | 3/2003 | Heymans et al. |
| 6,534,503 B1 | 3/2003 | Dines et al. |
| 6,534,509 B1 | 3/2003 | Bauman et al. |
| 6,555,537 B2 | 4/2003 | Bauman et al. |
| 6,569,861 B2 | 5/2003 | Bakthavatchalam et al. |
| 6,579,968 B1 | 6/2003 | Blood et al. |
| 6,612,805 B2 | 9/2003 | Rietsch |
| 6,648,848 B1 | 11/2003 | Keldmann et al. |
| 6,673,767 B1 | 1/2004 | Brodbeck et al. |
| 6,699,873 B1 | 3/2004 | Maguire et al. |
| 6,715,485 B1 | 4/2004 | Djupesland |
| 6,734,175 B2 | 5/2004 | Hadcock et al. |
| 6,811,543 B2 | 11/2004 | Keldmann et al. |
| 6,949,552 B2 | 9/2005 | Nakazato et al. |
| 7,326,707 B2 | 2/2008 | Sharma et al. |
| 7,354,923 B2 | 4/2008 | Sharma et al. |
| 7,456,184 B2 | 11/2008 | Sharma et al. |
| 2001/0018075 A1 | 8/2001 | Shigeyuki et al. |
| 2001/0047001 A1 | 11/2001 | Varkhedkar et al. |
| 2002/0004512 A1 | 1/2002 | Bakshi et al. |
| 2002/0010182 A1 | 1/2002 | Masaaki et al. |
| 2002/0019523 A1 | 2/2002 | Palucki et al. |
| 2002/0022620 A1 | 2/2002 | Kahn et al. |
| 2002/0032238 A1 | 3/2002 | Priepke et al. |
| 2002/0037837 A1 | 3/2002 | Takada et al. |
| 2002/0042399 A1 | 4/2002 | Kruse et al. |
| 2002/0052383 A1 | 5/2002 | Bakthavatchalam et al. |
| 2002/0065277 A1 | 5/2002 | Hadcock et al. |
| 2002/0065416 A1 | 5/2002 | Stasiak et al. |
| 2002/0072604 A1 | 6/2002 | Carpino et al. |
| 2002/0082263 A1 | 6/2002 | Lou et al. |
| 2002/0107253 A1 | 8/2002 | Koh et al. |
| 2002/0107255 A1 | 8/2002 | Blumberg et al. |
| 2002/0128247 A1 | 9/2002 | Dow et al. |
| 2002/0128270 A1 | 9/2002 | Neya et al. |
| 2002/0137664 A1 | 9/2002 | Bakshi et al. |
| 2002/0143141 A1 | 10/2002 | Chen et al. |
| 2002/0173512 A1 | 11/2002 | Moltzen et al. |
| 2002/0177598 A1 | 11/2002 | Bauman et al. |
| 2002/0183316 A1 | 12/2002 | Pan et al. |
| 2003/0004162 A1 | 1/2003 | Treadway |
| 2003/0013721 A1 | 1/2003 | Meghani et al. |
| 2003/0040520 A1 | 2/2003 | Guzi et al. |
| 2003/0055008 A1 | 3/2003 | Marcotte |
| 2003/0055009 A1 | 3/2003 | Steiner et al. |
| 2003/0055247 A1 | 3/2003 | Cosford et al. |
| 2003/0055265 A1 | 3/2003 | Binggeli et al. |
| 2003/0060473 A1 | 3/2003 | Neya et al. |
| 2003/0064921 A1 | 4/2003 | Millhauser et al. |
| 2003/0069169 A1 | 4/2003 | Macor et al. |
| 2003/0083228 A1 | 5/2003 | Carpino et al. |
| 2003/0083335 A1 | 5/2003 | Hayward |
| 2003/0092732 A1 | 5/2003 | Yu et al. |
| 2003/0096827 A1 | 5/2003 | Yu et al. |
| 2003/0105106 A1 | 6/2003 | Chiang et al. |
| 2003/0109556 A1 | 6/2003 | Mazur et al. |
| 2003/0125334 A1 | 7/2003 | Chiang et al. |
| 2003/0139425 A1 | 7/2003 | Bauman et al. |
| 2003/0144277 A1 | 7/2003 | DeLucca |
| 2003/0149019 A1 | 8/2003 | Bremberg et al. |
| 2003/0158205 A1 | 8/2003 | Bauman et al. |
| 2003/0158209 A1 | 8/2003 | Dyck et al. |
| 2003/0162819 A1 | 8/2003 | Eisinger et al. |
| 2003/0166637 A1 | 9/2003 | Lehmann-Lintz et al. |
| 2003/0176425 A1 | 9/2003 | Eisinger et al. |
| 2003/0181441 A1 | 9/2003 | McClure et al. |
| 2003/0191136 A1 | 10/2003 | Bakthavatchalam et al. |
| 2003/0195212 A1 | 10/2003 | Lundstedt et al. |
| 2004/0006067 A1 | 1/2004 | Fotsch et al. |
| 2004/0024211 A1 | 2/2004 | Boyce et al. |
| 2004/0034034 A1 | 2/2004 | Blumberg et al. |
| 2004/0053933 A1 | 3/2004 | Pontillo et al. |
| 2004/0147567 A1 | 7/2004 | Nakazato et al. |
| 2004/0152534 A1 | 8/2004 | Chapman et al. |
| 2004/0157264 A1 | 8/2004 | Sharma et al. |
| 2004/0171520 A1 | 9/2004 | Sharma et al. |
| 2004/0204398 A1 | 10/2004 | Bakshi et al. |
| 2004/0224957 A1 | 11/2004 | Sharma et al. |
| 2004/0254198 A1 | 12/2004 | Reynolds et al. |
| 2005/0124636 A1 | 6/2005 | Sharma et al. |
| 2005/0130988 A1 | 6/2005 | Sharma et al. |
| 2005/0176728 A1 | 8/2005 | Sharma et al. |
| 2006/0009456 A1 | 1/2006 | Hutchinson et al. |
| 2006/0084657 A1 | 4/2006 | Nakazato et al. |
| 2006/0287330 A1 | 12/2006 | Sharma et al. |
| 2006/0287331 A1 | 12/2006 | Sharma et al. |
| 2006/0287332 A1* | 12/2006 | Sharma et al. .......... 514/252.12 |
| 2008/0070921 A1 | 3/2008 | Burris et al. |
| 2008/0234289 A1 | 9/2008 | Sharma et al. |
| 2009/0076029 A1 | 3/2009 | Sharma et al. |

FOREIGN PATENT DOCUMENTS

| | | |
|---|---|---|
| WO | WO 97/46553 | 12/1997 |
| WO | WO 98/10653 | 3/1998 |
| WO | WO 98/17625 | 4/1998 |
| WO | WO 99/55679 | 11/1999 |
| WO | WO 99/58501 | 11/1999 |
| WO | WO 99/64002 | 12/1999 |
| WO | WO 00/01726 | 1/2000 |
| WO | WO 00/05373 | 2/2000 |
| WO | WO 00/17348 | 3/2000 |
| WO | WO 00/35952 | 6/2000 |
| WO | WO 00/36136 | 6/2000 |
| WO | WO 00/40247 | 7/2000 |
| WO | WO 00/53148 | 9/2000 |
| WO | WO 00/68185 | 11/2000 |
| WO | WO 00/74679 | 12/2000 |
| WO | WO 01/05401 | 1/2001 |
| WO | WO 01/10842 | 2/2001 |
| WO | WO 01/12176 | 2/2001 |
| WO | WO 01/13112 | 2/2001 |
| WO | WO 01/18210 | 3/2001 |
| WO | WO 01/21634 | 3/2001 |
| WO | WO 01/21647 | 3/2001 |
| WO | WO 01/23392 | 4/2001 |
| WO | WO 01/30343 | 5/2001 |
| WO | WO 01/30808 | 5/2001 |
| WO | WO 01/35970 | 5/2001 |
| WO | WO 01/52880 | 7/2001 |
| WO | WO 01/55106 | 8/2001 |
| WO | WO 01/55107 | 8/2001 |
| WO | WO 01/55109 | 8/2001 |
| WO | WO 01/70708 | 9/2001 |
| WO | WO 01/91752 | 12/2001 |
| WO | WO 02/00259 | 1/2002 |
| WO | WO 02/00654 | 1/2002 |
| WO | WO 02/12178 | 2/2002 |
| WO | WO 02/15909 | 2/2002 |
| WO | WO 02/18437 | 3/2002 |

| | | |
|---|---|---|
| WO | WO 02/47670 | 6/2002 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/062766 | 8/2002 |
| WO | WO 02/064091 | 8/2002 |
| WO | WO 02/064734 | 8/2002 |
| WO | WO 02/067869 | 9/2002 |
| WO | WO 02/068387 | 9/2002 |
| WO | WO 02/068388 | 9/2002 |
| WO | WO 02/069905 | 9/2002 |
| WO | WO 02/070511 | 9/2002 |
| WO | WO 02/079146 | 10/2002 |
| WO | WO 02/079203 | 10/2002 |
| WO | WO 02/079753 | 10/2002 |
| WO | WO 02/081443 | 10/2002 |
| WO | WO 02/085925 | 10/2002 |
| WO | WO 02/092566 | 11/2002 |
| WO | WO 03/006620 | 1/2003 |
| WO | WO 03/007949 | 1/2003 |
| WO | WO 03/009847 | 2/2003 |
| WO | WO 03/009850 | 2/2003 |
| WO | WO 03/013509 | 2/2003 |
| WO | WO 03/013571 | 2/2003 |
| WO | WO 03/020724 | 3/2003 |
| WO | WO 03/027239 | 4/2003 |
| WO | WO 03/031410 | 4/2003 |
| WO | WO 03/045920 | 6/2003 |
| WO | WO 03/053927 | 7/2003 |
| WO | WO 03/055477 | 7/2003 |
| WO | WO 03/061660 | 7/2003 |
| WO | WO 03/066587 | 8/2003 |
| WO | WO 03/066597 | 8/2003 |
| WO | WO 03/072056 | 9/2003 |
| WO | WO 03/092690 | 11/2003 |
| WO | WO 03/093234 | 11/2003 |
| WO | WO 03/094918 | 11/2003 |
| WO | WO 2004/037796 | 5/2004 |
| WO | WO 2005/102340 | 11/2005 |
| WO | WO 2006/014552 | 2/2006 |
| WO | WO 2007/021990 | 2/2007 |
| WO | WO 2007/021991 | 2/2007 |

OTHER PUBLICATIONS

U.S. Appl. No. 12/130,299, filed May 30, 2008, Burris et al.
U.S. Appl. No. 12/130,316, filed May 30, 2008, Sharma et al.
Abou-Gharbia et al. "Synthesis and SAR of Adatanserin: Novel Adamantyl Aryl- and Heteroarylpiperazines with Dual Serotonin 5-$HT_{1A}$ and 5-$HT_2$ Activity as Potential Anxiolytic and Antidepressant Agents" J. Med. Chem. 42(25):5077-5094 (1999).
Alterman et al. "Design and synthesis of new potent C2-symmetric HIV-1 protease inhibitors. Use of L-mannaric acid as a peptidomimetic scaffold" J. Med. Chem. 41:3782-3792 (1998).
Baldwin et al. "Synthesis of a bicyclic γ-lactam dipeptide analogue" Tetrahedron Letters 34(10):1665-1668 (1993).
Chang et al. "Morphiceptin (NH4-tyr-pro-phe-pro-COHN2): a potent and specific agonist for morphine (mu) receptors" Science 212(4490):75-77 (1981).
Cho et al. "Discovery of novel, potent and orally active nonpeptide antagonist of the human luteinizing hormone-releasing hormone (LHRH) receptor" J. Med. Chem. 41:4190-4195 (1998).
Chorev et al. "Toward nonpeptidal substance P mimetic analogues: Design, synthesis, and biological activity" Biopolymers 31(6):725-733 (1991).
Cornille et al. "Anodic amide oxidations: Conformationally restricted peptide building blocks from the direct oxidation of dipeptides" Tetrahedron Letters 35(38):6989-6992 (1994).
DiMaio et al. "Synthesis of chiral piperazin-2-ones as model peptidomimetics" J Chem. Soc., Perkin Trans I, 1687-1689 (1989).
Gante "Peptidomimetics—Tailored enzyme-inhibitors" Angewandte Chemie International Edition in English 33(17):1699-1720 (1994).
Giannis et al. "Peptidomimetics in drug design" Advances in Drug Research 29:1-78 (1997).
Haskell-Luevano et al. "Discovery of Prototype Peptidomimetic Agonists at the Human Melanocortin Receptors MC1R and MC4R" J. Med. Chem. 40:2133-2139 (1997).

Hruby et al. "Molecular organization of receptors—Efficacy, agonists, and antagonists" Annals of the New York Academy of Sciences 757:7-22 (1995).
Jones et al. "Clinically validated peptides as templates for de novo peptidomimetic drug design at G-protein coupled receptors" Current Opinion in Pharmacology 3:530-543 (2003).
Kask et al. "Discovery of a novel superpotent and selective melanocortin-4 receptor antagonist (HS024): Evaluation in vitro and in vivo" Endocrinology 139(12):5006-5014 (1998).
Kim et al. "Synthesis of (3R)-carboxy pyrrolidine (a β-proline analogue) and its oligomer" Bioorganic & Medicinal Chemistry Letters 10(21):2417-2419 (2000).
Klein et al. "O-benzyl hydroxyproline as a bioisostere for Phe-Pro: Novel dipeptide thrombin inhibitors" Bioorganic & Medicinal Chemistry Letters 6(18):2225-2230 (1996).
Lerner et al. "Synthetic melanocortin receptor. Agonist and antagonists" Cutaneous Neuroimmunomodulation: The Proopiomelanocortin System, Annals of the New York Academy of Sciences 885:153-160 (1995).
Medical Encyclopaedia: Female sexual dysfunction [online]. Retrieved on Oct. 10, 2007 from http://www.nlm.nih.gov/medlineplus/ency/article/003151.htm.
Moore et al. "A rapid screening system to determine drug affinities for the instestinal dipeptide transporter 2: Affinities of ACE inhibitors" International Journal of Pharmaceutics 210: 29-44 (2000).
Moore et al. "Designing Peptide Mimetics" Trends Pharmacol. Sci. 15:124-129 (1994).
Rarey et al. "Similarity searching in large combinatorial chemistry spaces" J. Computer-Aided Mol. Des. 15(6):497-520(2001).
Rubsam et al. "Synthesis of chiral piperazinones as versatile scaffolds for peptidomimetics" Tetrahedron 56(43):8481-8487 (2000).
Sasaki et al. "Discovery of a thieno[2,3-d]pyrimidine-2,4-dione bearing a p-methoxyureidophenyl moiety at the 6-position: A highly potent and orally bioavailable non-peptide antagonist for the human luteinizing hormone-releasing hormone receptor" J. Med. Chem. 46:113-124 (2003).
Schioth et al. "" Regulatory Peptides 106:7-12 (2002).
Shvachkin et al. "Synthesis of analogs of the thyrotropin-releasing hormone" Journal of General Chemistry of the USSR in English Translation 43(3):686-687 (1973).
Stavropoulos et al. "" Review of Clinical Pharmacology and Pharmacokinetics 103-106 (1995).
Sudoh et al. "Transport characteristics of peptidomimetics. Effect to the pyrrolinone bioisostere of transport across caco-2 cell monolayers" Pharmaceutical Research 15(5):719-725 (1998).
Takenaka et al. "Synthesis of met- and leu-enkephalin analogues containing chiral N,N-ethylene-bridged phenylalanyl-methionine and -leucine" J Chem. Soc., Perkin Trans I, 8:933-937 (1993).
Torres et al. "Neoglycopeptide synthesis and purification in multigram scale: preparation of O-(2,3,4,6-tetra-O-acetyl-beta-D-galactopyranosyl)-N alpha-fluoren-9-yl-methoxycarbonyl-hydroxyproline and its use in the pilot-scale synthesis of the potent analgesic glycopeptide O1.5-beta-D-galactopyranosyl [DMet2, Hyp5]enkephalinamide." Journal of Peptide Science 3(2):99-109 (1997).
Torres et al. "Synthesis and conformational analysis of a series of galactosyl enkephalin analogues showing high analgesic activity" The EMBO Journal 8(10):2925-2932 (1989).
Yamamoto "Synthesis and adhesive studies of marine polypeptides" J. Chem. Soc., Perkin Trans I, 3:613-618 (1987).
Zhorov et al. "Similarity of Ca2+-bound conformations of morphine and Met-enkephalin: A computational study" FEBS Letters 354(2):131-134 (1994).
Schioth et al. "Pharmacological comparison of rat and human melanocortin 3 and 4 receptors in vitro" Regulatory Peptides 106:7-12 (2002).
Stavropoulos et al. "Synthesis of cis-4-hydroxy-L-proline and its incorporation into biologically important peptides" Review of Clinical Pharmacology and Pharmacokinetics 103-106 (1995).
Adan et al. "Identification of antagonists for melanocortin MC3, MC4 and MC5 receptors" Eur. J. Pharmacol. 269(3): 331-337 (1994).

Adan et al. "Inverse agonism gains weight" Trends Pharmacol Sci. 24(6):315-321 (2003).

Door et al. "Evaluation of melanotan-II, a superpotent cyclic melanotropic peptide in a pilot phase-I clinical study" Life Science 58(20):1777-1784 (1996).

Grant "Synthetic Peptides: A User's Guide" GA Grant, editor W.H. Freeman & Co., New York 11-24 (1992).

Hadley et al. "Discovery and development of novel melanogenic drugs. Melanotan-I and -II" Pharm Biotechnol. 11:575-595 (1998).

Hruby et al. "Emerging approaches in the molecular design of receptor-selective peptide ligands: conformational, topographical and dynamic considerations" Biochem. J. 268:249-262 (1990).

Mitsunobu "The use of diethyl azodicarboxylate and triphenylphosphine in synthesis and transfromation of natural products" Synthesis 1:1-28 (1981).

Toniolo "Conformationally restricted peptides through short-range cyclizations" Int. J. Peptide Protein Res. 35:287-300 (1990).

Cachexia [online], retrieved on Nov. 19, 2009 from the internet (URL: http://en.wikipedia.org/wiki/Cachexia).

Inui "Cancer anorexia-cachexia syndrome: Current issues in research and management" CA A Cancer Journal for Clinicians 52:72-91 (2002).

Fan et al. "Role of melanocortinergic neurons in feeding and the agouti obesity syndrome" Nature 385(6612):165-168 (1997).

Holder et al. "Melanocortin ligands: 30 years of structure-activity relationship (SAR) studies" Medicinal Research Reviews 24(3): 325-356 (2004).

Hruby et al. "Synthesis of oligopeptide and peptidomimetic libraries" Current Opinion in Chemical Biology 1(1): 114-119 (1997).

* cited by examiner

MELANOCORTIN RECEPTOR-SPECIFIC PIPERAZINE COMPOUNDS WITH DIAMINE GROUPS

CROSS-REFERENCE TO RELATED APPLICATIONS

This application claims priority to and the benefit under 35 USC §119(e) of U.S. Provisional Patent Application Ser. No. 60/707,488, entitled "Substituted Melanocortin Receptor-Specific Piperazine Compounds", filed on Aug. 11, 2005.

A series of commonly-owned and related applications are being filed concurrently herewith, including specifically the U.S. utility applications entitled "Melanocortin Receptor-Specific Piperazine and Keto-Piperazine Compounds" and "Melanocortin Receptor-Specific Single Acyl Piperazine Compounds".

The specification and claims of each of the foregoing patent applications are incorporated herein by reference.

BACKGROUND OF THE INVENTION

1. Field of the Invention (Technical Field)

The present invention relates to tetra-substituted piperazine compounds with diamine groups that bind to one or more melanocortin receptors and are agonists, antagonists, mixed agonist-antagonists, inverse agonist or antagonists of inverse agonists with respect to one or more melanocortin receptors, and use thereof for the treatment of metabolic, immune, infection-related and other melanocortin receptor-mediated disorders, including treatment of obesity and related energy homeostasis disorders and diseases.

2. Background Art

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R), expressed primarily in cells in the hypothalamus, midbrain and brainstem, and melanocortin-5 receptors (MC5-R), expressed in a wide distribution of tissues.

In general, compounds specific for MC1-R are believed to be useful for treatment of melanoma. Compounds specific for MC3-R or MC4-R are believed to be useful in regulation of energy homeostasis, including use as agents for attenuating food intake and body weight gain, for use in treatment of anorexia, as a weight gain aid, for treatment of obesity, and treatment of other food intake and metabolism-related purposes. Compounds specific for MC3-R and MC4-R can further be used as agents for treatment of sexual dysfunction, including male erectile dysfunction and female sexual dysfunction. Other melanocortin receptor-specific compounds, such as MCR-1 agonists, can be used as tanning agents to increase melanin production in the skin, acting as chemopreventive agents against harmful effects of UV solar radiation. Compounds specific for MCR-1 and MCR-3 may further be useful in regulation of inflammatory processes.

There is a significant need for compounds with high specificity for discrete melanocortin receptors, as well as for compounds that are either agonists or antagonists for specific melanocortin receptors. High affinity compounds for melanocortin receptors can be used to exploit varied physiological responses associated with the melanocortin receptors, either as agonists or antagonists. In addition, melanocortin receptors have an effect on the activity of various cytokines, and high affinity compounds for melanocortin receptors can be used to regulate cytokine activity.

There are piperazine and piperidine compounds known, such as those disclosed in WO 02/070511 (Bristol-Myers Squibb Company), WO 02/059095 (Eli Lilly and Company), and WO 00/74679 (Merck & Co., Inc.), asserted to be specific for melanocortin or related receptors. However, in general such compounds have at most two functional substituted groups, have relatively poor affinity and specificity, and are not suitable for use as a drug compound. There is a significant need for compounds with high specificity for discrete receptors, such as melanocortin and other receptors, as well as compounds that are agonists or antagonists for such receptors. High affinity compounds for such receptors can be used to exploit varied physiological responses associated with the receptors, either as agonists or antagonists. There is thus a need for compounds that are more selective, including higher affinity and specificity, and in particular for compounds that have at least three or four biologically active substituted groups. This invention addresses that need.

WO 02/085925, "Melanocortin Receptor Ligands", to The Proctor & Gamble Company, discloses ketopiperazine structures and methods of synthesis thereof, but does not disclose piperazine structures, piperazine structures with four or more substituted groups, methods to synthesize piperazine structures, methods to synthesize piperazine structures with four or more substituted groups, or methods to synthesize optically pure structures, and further does not disclose structures with a single substituent group that is a single D-Phe or D-Nal residue, or a derivative or homolog thereof, optionally with an amine capping group.

Commonly owned of U.S. patent application Ser. No. 10/837,519, published as Publication No. US 2004/0224957 A1, discloses piperazine compounds specific for one or more melanocortin receptors, but does not disclose piperazine compounds with four substituted groups where one substituted group includes a diamine heteroatom unit with at least one cationic center, hydrogen bond donor or hydrogen bond acceptor, and the remaining three substituted groups each include a ring structure.

With respect to certain objects, methods, synthetic schemes, utilities, applications, definitions, protocols and other disclosures, this application is related to U.S. patent application Ser. No. 10/762,079, entitled "Piperazine Melanocortin-Specific Compounds", filed on Jan. 21, 2004 and International Application No. PCT/US02/25574, International Publication No. WO 03/013571, entitled "Peptidomimetics of Biologically Active Metallopeptides", filed on Aug. 12, 2002; and the specifications of each of the foregoing are incorporated herein by reference as if set forth in full.

There remains a significant need for compounds specific for MC4-R for treatment of conditions relating to regulation of energy homeostasis, including use as agents for attenuating food intake and body weight gain, for treatment of obesity, and treatment of other food intake and metabolism-related purposes.

SUMMARY OF THE INVENTION

The invention provides a compound having the formula of structure I:

or an enantiomer, stereoisomer or diastereoisomer thereof, or a pharmaceutically acceptable salt thereof, wherein J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, two substituted or unsubstituted aromatic carbocyclic rings wherein the rings are joined by a bond, —$CH_2$—, or —O—, and substituted or unsubstituted aromatic fused heterobicyclic ring groups, wherein in each instance the rings include 5 or 6 ring atoms;

W is a diamine heteroatom unit with at least one cationic center, hydrogen bond donor or hydrogen bond acceptor;

Q is an aromatic carbocyclic ring selected from the group consisting of phenyl, substituted phenyl, naphthyl and substituted naphthyl;

$L_1$ is a bond or a linker unit comprising from one to eight backbone atoms selected from the group consisting of carbon, sulfur, oxygen and nitrogen;

$L_2$ is a bond or —$(CH_2)_z$—;

$L_3$ is a bond or a linker unit comprising from one to nine backbone atoms selected from the group consisting of carbon, sulfur, oxygen and nitrogen;

one or two of $R_{1a}$, $R_{1b}$, $R_{2a}$, and $R_{2b}$ are independently a $C_1$ to $C_6$ aliphatic linear or branched chain and the remaining of $R_{1a}$, $R_{1b}$, $R_{2a}$, and $R_{2b}$ are hydrogen, provided that at least one of $R_{1a}$ and $R_{1b}$ and at least one of $R_{2a}$ and $R_{2b}$ are hydrogen;

or one of $R_{1a}$, $R_{1b}$, $R_{2a}$, and $R_{2b}$ are and the remaining of $R_{1a}$, $R_{1b}$, $R_{2a}$, and $R_{2b}$ are hydrogen;

or $R_{1a}$ and $R_{1b}$ together form =O and one of $R_{2a}$ and $R_{2b}$ is a $C_1$ to $C_6$ aliphatic linear or branched chain, and the remaining of $R_{2a}$ and $R_{2b}$ is hydrogen;

X is $CH_2$, C=O or C=S;

z is an index value from 1 to 6; and y is an index value from 0 to 5;

wherein the carbon atom marked with an asterisk can have any stereochemical configuration. In the compound of structure I, J may be:

unsubstituted or substituted with one or more ring substituents, including one or more ring substituents independently selected from the group consisting of hydroxyl, halogen, sulfonamide, alkyl, —O-alkyl, aryl, and —O-aryl.

In the compound of structure I, Q may be:

where $R_{3a}$, $R_{3b}$ and $R_{3c}$ are optional ring substituents, and when one or more are present, are the same or different and independently hydroxyl, halogen, alkyl, —O-alkyl, aryl, or —O-aryl. In one aspect, at least one of $R_{3a}$, $R_{3b}$ or $R_{3c}$ is —$CH_3$ or —O—$CH_3$. In another aspect, at least one of $R_{3a}$, $R_{3b}$ or $R_{3c}$ is —Cl or —$CF_3$.

In one aspect of the invention, Q and J are the same. In another aspect, $L_1$-J and $L_3$-Q are the same. Where Q and J are the same, both may be an aromatic carbocyclic ring selected from the group consisting of phenyl, substituted phenyl, naphthyl and substituted naphthyl.

In the compound of structure I, W may include an amine, amide, alcohol, carboxylic acid, ether, ester, or urea. Thus in one aspect W is where $R_4$ is
  NH,
  O, provided that $R_5$ comprises a diamine,
  $CH_2$, provided that $R_5$ comprises a diamine,
  $C_6H_5$, provided that $R_5$ comprises a diamine,
  N(—$CH_2$)$_z$ where N($CH_2$)$_z$ together with $R_5$ forms a ring,
  N(—($CH_2$)$_y$—$CH_3$),
  NH—C(=O),
  NH—C(=O)—NH, provided that $R_5$ does not comprise an N,
  C(=O), provided that $R_5$ comprises a diamine,
  C(=O)—NH,
  C(=O)—O, provided that $R_5$ comprises a diamine, or
  O—C(=O), provided that $R_5$ comprises a diamine;
$R_5$ is
  $NH_2$, provided that $R_4$ comprises one N,
  hydroxyl, provided that $R_4$ comprises a diamine, $CH_3$, provided that $R_4$ comprises a diamine, $NH-(CH_2)_z$ where $NH-(CH_2)_z$ together with $R_4$ forms a ring, $NH-(CH_2)_y-CH_3$, $N(-(CH_2)_y-CH_3)_2$, $NH-(CH_2)_z-NH_2$, $NH-(CH_2)_z-NH-(CH_2)_y-CH_3$, $NH-(CH_2)_z-N-((CH_2)_y-CH_3)_2$, $N(-(CH_2)_y-CH_3)-(CH_2)_z-NH(CH_2)_y-CH_3$, $N(-(CH_2)_y-CH_3)-(CH_2)_z-N((CH_2)_y-CH_3)_2$, $NH-C(=O)-(CH_2)_y-NH_2$, $O-(CH_2)_y-CH_3$, provided that $R_4$ comprises a diamine, $SO_2-NH_2$, $SO_2-NH-(CH_2)_y-CH_3$, $SO_2-N(-(CH_2)_y-CH_3)_2$, $SO_2-(CH_2)_y-CH_3$, provided that $R_4$ comprises a diamine,

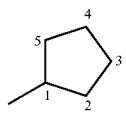

where none, one or more of positions 1 to 5 are a heteroatom selected from N for position 1 and S, O or NH for positions 2 to 5, provided that only one N is present if $R_4$ comprises an N, no N is present if $R_4$ comprises a diamine and otherwise $R_5$ comprises a diamine,

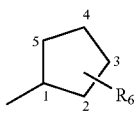

where none, one or two of positions 1 to 5 are a heteroatom selected from N for position 1 and for the position to which $R_6$ is bound if such position does not comprise C, and otherwise S, O or NH, provided that $R_5$ including $R_6$ comprises only one N if $R_4$ comprises an N, no N is present if $R_4$ comprises a diamine and otherwise $R_5$ including $R_6$ comprises a diamine,

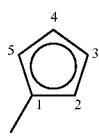

where at least one bond between adjacent ring atoms is a double bond, and none or one or more of positions 1 to 5 are a heteroatom selected from N for position 1 and any double bond position and otherwise S, O or NH for positions 2 to 5, provided that not more than one position is S or O, and further provided that only one N is present if $R_4$ comprises an N, no N is present if $R_4$ comprises a diamine and otherwise $R_5$ comprises a diamine,

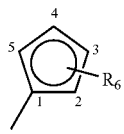

where at least one bond between adjacent ring atoms is a double bond, and one or more of positions 1 to 5 are optionally a heteroatom selected from N for position 1, the position to which $R_6$ is bound if such position does not comprise C, and any double bond position and otherwise S, O or NH for positions 2 to 5, provided that not more than one position is S or O, and further provided that $R_5$ including $R_6$ comprises only one N if $R_4$ comprises an N, no N is present if $R_4$ comprises a diamine and otherwise $R_5$ including $R_6$ comprises a diamine,

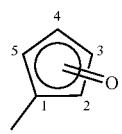

where at least one bond between adjacent ring atoms is a double bond, the oxo is bound to a ring carbon, and one or more of the remaining of positions 1 to 5 are optionally a heteroatom selected from N for position 1 and any double bond position and otherwise S, O or NH for positions 2 to 5, provided that not more than one ring position is S or O, and further provided that only one N is present if $R_4$ comprises an N, no N is present if $R_4$ comprises a diamine and otherwise $R_5$ comprises a diamine,

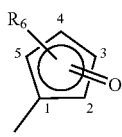

where at least one bond between adjacent ring atoms is a double bond, the oxo is bound to a ring carbon, and one or more of positions 1 to 5 are optionally a heteroatom selected from N for position 1, the position to which $R_6$ is bound if such position does not comprise C, and any double bond position and otherwise S, O or NH for positions 2 to 5, provided that not more than one position is S or O, and further provided that $R_5$ including $R_6$ comprises only one N if $R_4$ comprises an N, no N is present if $R_4$ comprises a diamine and otherwise $R_5$ including $R_6$ comprises a diamine,

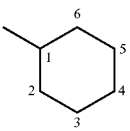

where one or more of positions 1 to 6 are a heteroatom selected from N for position 1 and S, O or NH for positions 2 to 6, provided that $R_5$ together with $R_6$ comprises only one N if $R_4$ comprises an N, no N is present if $R_4$ comprises a diamine and otherwise $R_5$ including $R_6$ comprises a diamine,

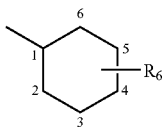

where none, one or two of positions 1 to 6 are a heteroatom selected from N for position 1 and the position to which $R_6$ is bound if such position does not comprise C, and otherwise S, O or NH, provided that $R_5$ including $R_6$ comprises only one N if $R_4$ comprises an N, no N is present if $R_4$ comprises a diamine and otherwise $R_5$ including $R_6$ comprises a diamine,

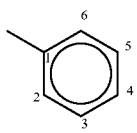

where at least one bond between adjacent ring atoms is a double bond, and one or more of positions 1 to 6 are a heteroatom selected from N for position 1 and any double bond position and otherwise S, O or NH or N—$(CH_2)_y$—$CH_3$ for positions 2 to 6, provided that not more than two positions are S or O, and further provided that $R_5$ together with $R_6$ comprises only one N if $R_4$ comprises an N, no N is present if $R_4$ comprises a diamine and otherwise $R_5$ including $R_6$ comprises a diamine,

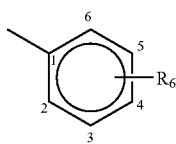

where at least one bond between adjacent ring atoms is a double bond, and one or more of positions 1 to 6 are optionally a heteroatom selected from N for position 1 and any double bond position and otherwise S, O or NH for positions 2 to 6, provided that not more than two positions are S or O, and further provided that $R_5$ including $R_6$ comprises only one N if $R_4$ comprises an N, no N is present if $R_4$ comprises a diamine and otherwise $R_5$ including $R_6$ comprises a diamine,

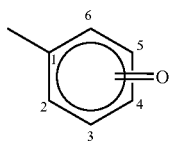

where at least one bond between adjacent ring atoms is a double bond, the oxo is bound to a ring carbon, and one or more of the remaining of positions 1 to 6 are optionally a heteroatom selected from N for position 1 and any double bond position and otherwise S, O or NH for positions 2 to 6, provided that not more than two positions are S or O, and further provided that only one N is present if $R_4$ comprises an N, no N is present if $R_4$ comprises a diamine and otherwise $R_5$ comprises a diamine, or

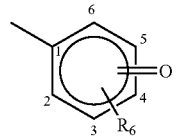

where at least one bond between adjacent ring atoms is a double bond, the oxo is bound to a ring carbon, and one or more of positions 1 to 6 are optionally a heteroatom selected from N for position 1, the position to which $R_6$ is bound if such position does not comprise C, and any double bond position and otherwise S, O or NH for positions 2 to 6, provided that not more than two positions are S or O, and further provided that $R_5$ including $R_6$ comprises only one N if $R_4$ comprises an N, no N is present if $R_4$ comprises a diamine and otherwise $R_5$ including $R_6$ comprises a diamine;

$R_6$ is hydroxyl, $(CH_2)_y$—$CH_3$, $(CH_2)_y$—$NH_2$, $NH_2$, NH—$(CH_2)_y$—$CH_3$ or N(—$(CH_2)_y$—$CH_3)_2$;

t is an index value from 0 to 6;

z is an index value from 1 to 6; and y is in each instance independently an index value from 0 to 5;

provided that, any NH or $NH_2$ in the foregoing may be substituted by N-Prg or NH-Prg, respectively, where each Prg is independently an amine protecting group. In the foregoing depictions of ring structures containing a circle within the ring, it is to be understood that the ring structure may include only one double bond, or may include more than one double bond, and in particular, the use of the circle does not imply that all possible double bonds are present. Where a Prg is present, each Prg may independently be acetyl, adamantyloxy, benzoyl, benzyl, benzyloxy, t-butoxycarbonyl, mesitylene-2-sulfonyl, 4-methoxy-2,3-6-trimethyl-benzenesulfonyl, 2,2,4,6,7-pentamethyldihydrobenzofurane-5-sulfonyl, 2,2,5,7,8-pentamethylchromane-6-sulfonyl, or tosyl.

In another aspect of the compound of structure I, W is

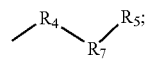

where $R_4$ is

NH,

O, provided that $R_5$ comprises a diamine, $CH_2$, provided that $R_5$ comprises a diamine, N(—$CH_2)_z$ where N$(CH_2)_z$ together with $R_5$ forms a ring, N(—$(CH_2)_y$—$CH_3$),

NH—C(=O),

NH—C(=O)—NH, provided that $R_5$ does not comprise an N,

C(=O), provided that $R_5$ comprises a diamine,

C(=O)—NH,

C(=O)—O, provided that $R_5$ comprises a diamine, or

O—C(=O), provided that $R_5$ comprises a diamine;

$R_5$ is
NH$_2$, provided that $R_4$ comprises one N,
hydroxyl, provided that $R_4$ comprises a diamine,
CH$_3$, provided that $R_4$ comprises a diamine,
NH—(CH$_2$)$_z$ where NH—(CH$_2$)$_z$ together with $R_4$ forms a ring,
NH—(CH$_2$)$_y$—CH$_3$,
N(—(CH$_2$)$_y$—CH$_3$)$_2$,
NH—(CH$_2$)$_z$—NH$_2$,
NH—(CH$_2$)$_z$—NH—(CH$_2$)$_y$—CH$_3$,
NH—(CH$_2$)$_z$—N—((CH$_2$)$_y$—CH$_3$)$_2$,
N(—(CH$_2$)$_y$—CH$_3$)—(CH$_2$)$_z$—NH(CH$_2$)$_y$—CH$_3$,
N(—(CH$_2$)$_y$—CH$_3$)—(CH$_2$)$_z$—N((CH$_2$)$_y$—CH$_3$)$_2$,
NH—C(=O)—(CH$_2$)$_y$—NH$_2$,
O—(CH$_2$)$_y$—CH$_3$, provided that $R_4$ comprises a diamine,
SO$_2$—NH$_2$,
SO$_2$—NH—(CH$_2$)$_y$—CH$_3$,
SO$_2$—N(—(CH$_2$)$_y$—CH$_3$)$_2$,
SO$_2$—(CH$_2$)$_y$—CH$_3$, provided that $R_4$ comprises a diamine,

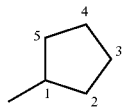

where none, one or more of positions 1 to 5 are a heteroatom selected from N for position 1 and S, O or NH for positions 2 to 5, provided that only one N is present if $R_4$ comprises an N, no N is present if $R_4$ comprises a diamine and otherwise $R_5$ comprises a diamine,

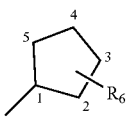

where none, one or two of positions 1 to 5 are a heteroatom selected from N for position 1 and for the position to which $R_6$ is bound if such position does not comprise C, and otherwise S, O or NH, provided that $R_5$ including $R_6$ comprises only one N if $R_4$ comprises an N, no N is present if $R_4$ comprises a diamine and otherwise $R_5$ including $R_6$ comprises a diamine,

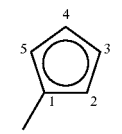

where at least one bond between adjacent ring atoms is a double bond, and none or one or more of positions 1 to 5 are a heteroatom selected from N for position 1 and any double bond position and otherwise S, O or NH for positions 2 to 5, provided that not more than one position is S or O, and further provided that only one N is present if $R_4$ comprises an N, no N is present if $R_4$ comprises a diamine and otherwise $R_5$ comprises a diamine,

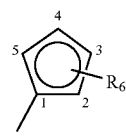

where at least one bond between adjacent ring atoms is a double bond, and one or more of positions 1 to 5 are optionally a heteroatom selected from N for position 1, the position to which $R_6$ is bound if such position does not comprise C, and any double bond position and otherwise S, O or NH for positions 2 to 5, provided that not more than one position is S or O, and further provided that $R_5$ including $R_6$ comprises only one N if $R_4$ comprises an N, no N is present if $R_4$ comprises a diamine and otherwise $R_5$ including $R_6$ comprises a diamine,

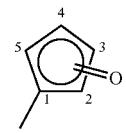

where at least one bond between adjacent ring atoms is a double bond, the oxo is bound to a ring carbon, and one or more of the remaining of positions 1 to 5 are optionally a heteroatom selected from N for position 1 and any double bond position and otherwise S, O or NH for positions 2 to 5, provided that not more than one ring position is S or O, and further provided that only one N is present if $R_4$ comprises an N, no N is present if $R_4$ comprises a diamine and otherwise $R_5$ comprises a diamine,

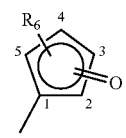

where at least one bond between adjacent ring atoms is a double bond, the hydroxyl is bound to a ring carbon, and one or more of positions 1 to 5 are optionally a heteroatom selected from N for position 1, the position to which $R_6$ is bound if such position does not comprise C, and any double bond position and otherwise S, O or NH for positions 2 to 5, provided that not more than one position is S or O, and further provided that $R_5$ including $R_6$ comprises only one N if $R_4$ comprises an N, no N is present if $R_4$ comprises a diamine and otherwise $R_5$ including $R_6$ comprises a diamine,

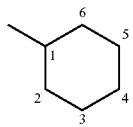

where one or more of positions 1 to 6 are a heteroatom selected from N for position 1 and S, O or NH for positions 2 to 6, provided that $R_5$ together with $R_6$ comprises only one N if $R_4$ comprises an N, no N is present if $R_4$ comprises a diamine and otherwise $R_5$ including $R_6$ comprises a diamine,

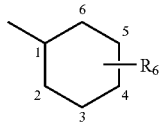

where none, one or two of positions 1 to 6 are a heteroatom selected from N for position 1 and the position to which $R_6$ is bound if such position does not comprise C, and otherwise S, O or NH, provided that $R_5$ including $R_6$ comprises only one N if $R_4$ comprises an N, no N is present if $R_4$ comprises a diamine and otherwise $R_5$ including $R_6$ comprises a diamine,

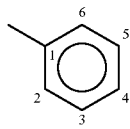

where at least one bond between adjacent ring atoms is a double bond, and one or more of positions 1 to 6 are a heteroatom selected from N for position 1 and any double bond position and otherwise S, O or NH or N—$(CH_2)_y$—$CH_3$ for positions 2 to 6, provided that not more than two positions are S or O, and further provided that $R_5$ together with $R_6$ comprises only one N if $R_4$ comprises an N, no N is present if $R_4$ comprises a diamine and otherwise $R_5$ including $R_6$ comprises a diamine,

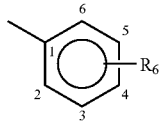

where at least one bond between adjacent ring atoms is a double bond, and one or more of positions 1 to 6 are optionally a heteroatom selected from N for position 1 and any double bond position and otherwise S, O or NH for positions 2 to 6, provided that not more than two positions are S or O, and further provided that $R_5$ including $R_6$ comprises only one N if $R_4$ comprises an N, no N is present if $R_4$ comprises a diamine and otherwise $R_5$ including $R_6$ comprises a diamine,

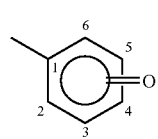

where at least one bond between adjacent ring atoms is a double bond, the oxo is bound to a ring carbon, and one or more of the remaining of positions 1 to 6 are optionally a heteroatom selected from N for position 1 and any double bond position and otherwise S, O or NH for positions 2 to 6, provided that not more than two positions are S or O, and further provided that only one N is present if $R_4$ comprises an N, no N is present if $R_4$ comprises a diamine and otherwise $R_5$ comprises a diamine, or

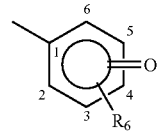

where at least one bond between adjacent ring atoms is a double bond, the oxo is bound to a ring carbon, and one or more of position 1 to 6 are optionally a heteroatom selected from N for position 1, the position to which $R_6$ is bound if such position does not comprise C, and any double bond position and otherwise S, O or NH for positions 2 to 6, provided that not more than two positions are S or O, and further provided that $R_5$ including $R_6$ comprises only one N if $R_4$ comprises an N, no N is present if $R_4$ comprises a diamine and otherwise $R_5$ including $R_6$ comprises a diamine;

$R_6$ is hydroxyl, $(CH_2)_y$—$CH_3$, $(CH_2)_y$—$NH_2$, $NH_2$, NH—$(CH_2)_y$—$CH_3$ or N(—$(CH_2)_y$—$CH_3)_2$;

$R_7$ is a $C_4$ to $C_{10}$ aliphatic comprising an optionally substituted cycloalkane or aryl ring;

z is an index value from 1 to 6; and y is in each instance independently an index value from 0 to 5;

wherein any NH or $NH_2$ in the foregoing may be substituted by N-Prg or NH-Prg, respectively, where each Prg is independently an amine protecting group. In the foregoing depictions of ring structures containing a circle within the ring, it is to be understood that the ring structure may include only one double bond, or may include more than one double bond, and in particular, the use of the circle does not imply that all possible double bonds are present. Here too if Pro is present each Prg may independently be acetyl, adamantyloxy, benzoyl, benzyl, benzyloxycarbonyl, t-butoxycarbonyl, mesitylene-2-sulfonyl, 4-methoxy-2,3-6-trimethyl-benzenesulfonyl, 2,2,4,6,7-pentamethyldihydrobenzofurane-5-sulfonyl, 2,2,5,7,8-pentamethylchromane-6-sulfonyl, 9-fluorenylmethoxycarbonyl or tosyl.

The invention further includes compounds of structure I of the formulas:

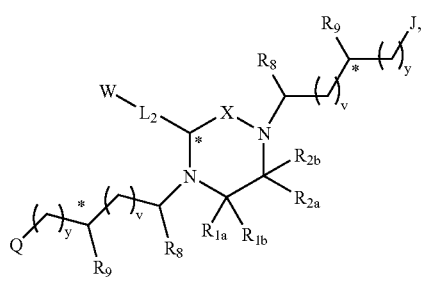

-continued

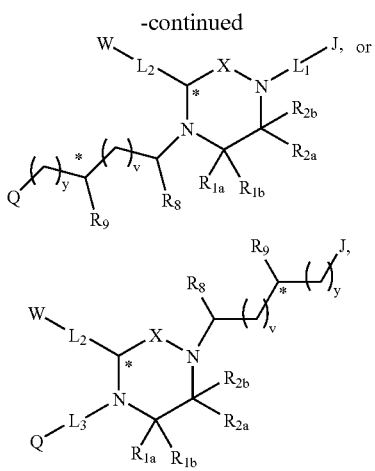

wherein
each occurrence of $R_8$ is independently H or =O;
each occurrence of $R_9$ is independently hydrogen or $N(R_{10a}R_{10b})$;
each occurrence of $R_{10a}$ and $R_{10b}$ is independently hydrogen, acetyl, methyl, ethyl, propyl, isopropyl, butyl, pentyl, hexyl, isobutyl, benzyl, benzoyl, hexanoyl, propionyl, butanoyl, pentanoyl, heptanoyl, cyclopropyl, cyclopropylmethyl, cyclobutyl, cyclobutylmethyl, cyclohexyl, cyclohexylmethyl, or polyethylene glycol;
v is in each instance an independent index value from 0 to 2; and
y is in each instance an independent index value from 0 to 5;
wherein if $R_9$ is not hydrogen, the carbon atom marked with an asterisk can have any stereochemical configuration. Where polyethylene glycol is present, it may have a formula molecular weight of between 100 and 50,000.

In one aspect of the compound of structure I, one of $R_{2a}$ and $R_{2b}$ is

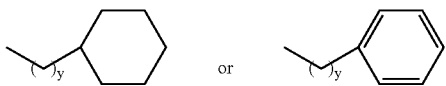

and the remaining of $R_{2a}$ and $R_{2b}$ and both $R_{1a}$ and $R_{1b}$ are hydrogen. The invention further provides a compound having the formula of structure II

II

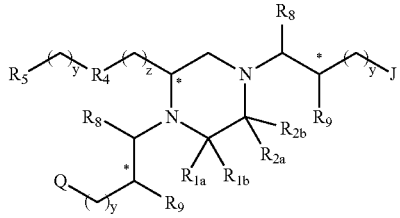

or an enantiomer, stereoisomer or diastereoisomer thereof, or a pharmaceutically acceptable salt thereof,
wherein
J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, two substituted or unsubstituted aromatic carbocyclic rings wherein the rings are joined by a bond, —$CH_2$— or —O—, and substituted or unsubstituted aromatic fused heterobicyclic ring groups, wherein in each instance the rings include 5 or 6 ring atoms;

Q is an aromatic carbocyclic ring selected from the group consisting of phenyl, substituted phenyl, naphthyl and substituted naphthyl;

one or two of $R_{1a}$, $R_{1b}$, $R_{2a}$, and $R_{2b}$ are independently a $C_1$ to $C_6$ aliphatic linear or branched chain and the remaining of $R_{1a}$, $R_{1b}$, $R_{2a}$, and $R_{2b}$ are hydrogen, provided that at least one of $R_{1a}$ and $R_{1b}$ and at least one of $R_{2a}$ and $R_{2b}$ are hydrogen;
or one of $R_{1a}$, $R_{1b}$, $R_{2a}$, and $R_{2b}$ are

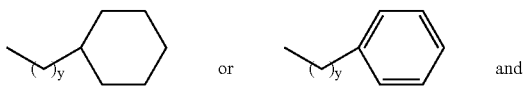

the remaining of $R_{1a}$, $R_{1b}$, $R_{2a}$, and $R_{2b}$ are hydrogen;
or $R_{1a}$ and $R_{1b}$ together form =O and one of $R_{2a}$ and $R_{2b}$ is a $C_1$ to $C_6$ aliphatic linear or branched chain,

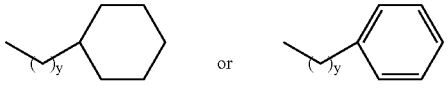

and the remaining of $R_{2a}$ and $R_{2b}$ is hydrogen;
$R_4$ is NH, N(—$(CH_2)_y$—$CH_3$), NH—C(=O), or C(=O)—NH;
$R_5$ is $NH_2$, NH—$(CH_2)_y$—$CH_3$, or N(—$(CH_2)_y$—$CH_3$)$_2$;
$R_8$ is in each instance independently H or =O;
$R_9$ is in each instance independently H or $N(R_{10a})(R_{10b})$;
$R_{10a}$ and $R_{10b}$ are each independently hydrogen, acetyl, methyl, ethyl, propyl, isopropyl, butyl, pentyl, hexyl, isobutyl, benzyl, pentyl, hexyl, benzoyl, hexanoyl, propionyl, butanoyl, pentanoyl, heptanoyl, cyclopropyl, cyclopropylmethyl, cyclobutyl, cyclobutylmethyl, cyclohexyl, or cyclohexylmethyl;
y is in each instance independently an index value from 0 to 5; and
z is an index value from 1 to 6;
wherein the carbon atoms marked with an asterisk can have any stereochemical configuration.

In another aspect there is provided a pharmaceutical composition comprising a compound of structure I or structure II and a pharmaceutically acceptable carrier. Such pharmaceutical composition may be employed in a method for affecting melanocortin receptor function in a human or non-human mammal, comprising the step of administering the pharmaceutical composition. There is further provided a method for treating a condition responsive to changes in melanocortin receptor function in a human or non-human mammal, comprising the step of administering the pharmaceutical composition. In the method, the condition may be selected from the group consisting of male sexual dysfunction, female sexual dysfunction, an eating disorder, above optimal body weight, obesity, below-optimal body weight and cachexia.

The present invention further provides compounds that are agonists of a melanocortin receptor, including one or more of MC1-R, MC3-R, MC4-R, or MC5-R. The compounds alternatively are antagonists of a melanocortin receptor, including one or more of MC1-R, MC3-R, MC4-R, or MC5-R. The compounds alternatively are inverse agonists of a melanocortin receptor, including one or more of MC1-R, MC3-R, MC4-R, or MC5-R. The compounds alternatively are antagonists of an inverse agonist of a melanocortin receptor, including one or more of MC1-R, MC3-R, MC4-R, or MC5-R.

The invention further includes methods for altering a disorder or condition associated with the activity of a melanocortin receptor, comprising administering to a patient a pharmaceutically effective amount a compound of this invention. In one embodiment the disorder or condition is an eating disorder such as cachexia. In another embodiment the disorder or condition is obesity and associated impairment of energy homeostasis. In yet another embodiment the disorder or condition is sexual dysfunction such as erectile dysfunction or female sexual dysfunction.

One object of the present invention is to provide conformationally constrained and optically pure isomers of tetra-substituted piperazine, wherein the pendant group substituents are amino acid moieties, amino acid side chain moieties or derivatives thereof, such that the resulting ring compound biologically mimics a relevant reverse turn peptide structure.

Another object of the present invention is to provide methods for the synthesis of optically pure tetra-substituted piperazine compounds.

Another object of the present invention is to provide piperazine compounds with four pendant groups, such pendant groups consisting of any moiety other than H, O, S, or a halogen.

Another object of the present invention is to provide piperazine core compounds wherein pendant groups are provided, which pendant groups are or include amino acid side chain moieties.

Another object of the present invention is to provide a tetra-substituted piperazine compound wherein such compound is specific for one or more melanocortin receptors.

Another object of the present invention is to provide a method for synthesis of tetra-substituted piperazine compounds of the invention.

Other objects, advantages and novel features, and the further scope of applicability of the present invention will be set forth in part in the detailed description to follow, and in part will become apparent to those skilled in the art upon examination of the following, or may be learned by practice of the invention.

DETAILED DESCRIPTION OF THE INVENTION

In this invention it is disclosed that piperazine rings may be employed with four descriptors, wherein each descriptor is a separate pendant group unique to a given ring atom, and where one descriptor includes a heteroatom diamine group. At least two, and optionally all three, of the remaining pendant groups comprise a ring structure, wherein the ring in each of the descriptors or pendant groups may be heterocyclic or carbocyclic, and where at least two of such rings are aromatic. By employing four descriptors, the inventors have further found that the chirality of the ring, and stereo structure generally, is fixed in a desired structure, thereby more closely mimicking the desired pharmacophores, and with the descriptors positioned in the most relevant chemical space.

This invention thus discloses the use of tetra-substituted piperazine templates where one substitution comprises a diamine for drug design. The invention further also relates to enantiomerically pure tetra-substituted piperazines, preferably made by the synthetic schemes disclosed herein or variants thereof. A classical piperazine ring is a conformationally dynamic six-membered ring structure. It can exist in a variety of conformational states, commonly referred to as chair, boat, twisted chair or twisted boat conformations. Because of this dynamism in structural states, the location of descriptors on the ring plays an important role in stabilizing the ring in a single conformational state; if the appropriate conformational state is selected, this is conducive to making a molecule more selective for its receptor. For example, a 1,3 axial placement of two bulky descriptors generally causes unfavorable steric interactions between these two groups, and thus make a chair conformation energetically less stable. Consequently, the chair conformation is less preferred, resulting in a twisted chair or boat conformation. The twisted chair or boat conformation results in a specific stereochemical alignment of the descriptors, which is specifically relevant to interaction with the desired receptor. Thus, a conformation resulting from 1,3 axial placement of two descriptors may result in a structure more selective for a given receptor sub-type.

In yet another embodiment, the invention describes tetra-substituted piperazine compounds in which one substituted group includes a diamine which are specific for G-protein coupled receptor systems, such systems including, but not limited to, melanotropin or melanocortin receptors (MC1-R, MC3-R, MC4-R and MC5-R).

In yet another embodiment, the invention provides novel schemes and methods of synthesis of tetra-substituted piperazine compounds.

Definitions. Before proceeding further with the description of the invention, certain terms are defined as set forth herein.

The "amino acid" and "amino acids" used in this invention, and the terms as used in the specification and claims, include the known naturally occurring protein amino acids, which are referred to by both their common three letter abbreviation and single letter abbreviations. See generally *Synthetic Peptides: A User's Guide*, G A Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference.

The term "amino acid side chain moiety" used in this invention includes any side chain of any amino acid, as the term "amino acid" is defined herein, including any derivative of an amino acid side chain moiety, as the term "derivative" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, and saturated or unsaturated alkyl, aryl or aralkyl moieties.

In the listing of compounds according to the present invention, conventional amino acid residues have their conventional meaning as given in Chapter 2400 of the *Manual of Patent Examining Procedure,* 8$^{th}$ Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine, "Ser" is serine and so on.

In the specification and the claims, the term "homolog" includes, without limitation, (a) a D-amino acid residue or side chain substituted for an L-amino acid residue side chain, (b) a post-translationally modified residue or side chain substituted for the residue or side chain, (c) a non-peptide or other modified amino acid residue or side chain based on another such residue or side chain, such as phenylglycine, homophenylalanine, ring-substituted halogenated, and alkylated or arylated phenylalanines for a phenylalanine residue, diamino proionic acid, diamino butyric acid, ornithine, lysine and homoarginine for an arginine residue, and the like, and (d) any amino acid residue or side chain, coded or otherwise, or a construct or structure that mimics an amino acid residue or side chain, and which has at least a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —R$^a$R$^b$ where R$^a$ is an alkylene (a bivalent alkyl) group and R$^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group CH$_3$CO—.

A group or aliphatic moiety is "acylated" when an alkyl or substituted alkyl group as defined above is bonded through one or more carbonyl [—(C=O)—] groups.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—CO.NH$_2$), such as methylamide, ethylamide, propylamide, and the like.

An "imide" includes compounds containing an imido group (—CO.NH.CO—).

An "amine" includes compounds that contain an amino group (—NH$_2$).

A "nitrile" includes compounds that are carboxylic acid derivatives and contain a (—CN) group bound to an organic group.

An amino acid side chain moiety is "hydrogen bonding" when the side chain includes hydrogen bond donors and/or hydrogen bond acceptors.

An "amine capping group" includes any terminal group attached through a terminal amine, including but not limited to any omega amino derivative, acyl group or terminal aryl or aralkyl, including groups such as a C$_1$ to C$_6$ linear or branched chain such as methyl, dimethyl, ethyl, propyl, isopropyl, butyl, isobutyl, pentyl, or hexyl, groups such as allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc, or a molecule such as polyethylene glycol with a formula molecular weight of between 100 and 50,000.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and one or more pharmaceutically acceptable carriers and/or other excipients, and optionally one or more other pharmaceutically active ingredients and agents.

A variety of chemicals and compounds are employed in this invention, and the following abbreviations have the meanings given:

| | |
|---|---|
| Boc | tertiary butyloxycarbonyl |
| Cbz | benzyloxycarbonyl |
| DCM | dichloromethane |
| DIAD | diisopropyl azodicarboxylate |
| DMF | N,N-dimethylformamide |
| DMSO | dimethyl sulfoxide |
| EDC | N-(3-dimethylaminopropyl)-N'-ethylcarbodiimide hydrochloride |
| EtOAc | ethyl acetate |
| Fmoc | 9-fluorenylmethoxycarbonyl |
| HEPES | 4-(2-hydroxyethyl)1-piperazine-ethanesulfonic acid |
| HOAt | 1-hydroxy-7-azabenzotriazole |
| IBCF | isobutyl chloroformate |
| LAH | lithium aluminum hydride |
| NMM | N-methylmorpholine |
| Pd/C | palladium on carbon |
| TBTU | 2-(1H-Benzotriazole-1-yl)-1,1,3,3-tetramethyluronium tetrafluoroborate |
| TEA | triethylamine |
| THF | tetrahydrofuran |
| TPP | triphenylphosphine |

A "tetra-substituted piperazine", as used herein, is a piperazine compound or derivative thereof wherein a group other than solely H, and preferably including an amino acid residue or an amino acid side chain moiety, is attached to each ring N member, and further wherein groups other than solely H, O, S or a halogen, preferably including an amino acid side chain moiety, are attached to two ring C members.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and may include the inability to attain or sustain an erection of sufficient rigidity for coitus. Symptoms of erectile dysfunction include an inability to achieve or maintain an erection, ejaculatory failure, premature ejaculation, or inability to achieve an orgasm, which symptoms may occur separately or in any combination. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females may also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, stress, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By a melanocortin receptor "agonist" is meant an endogenous or drug substance or compound, including a compound of this invention, which can interact with a melanocortin receptor and initiate a pharmacological response characteristic of the melanocortin receptor. By a melanocortin receptor "antagonist" is meant a drug or a compound, including a compound of this invention, which opposes the melanocortin receptor-associated responses normally induced by a melanocortin receptor agonist agent.

By "binding affinity" is meant the ability of a compound or drug to bind to its biological target.

The chemical naming protocol and structure diagrams used herein employ and rely on the chemical naming features as utilized by the ChemDraw program (available from Cambridgesoft Corp.) or ISIS Draw (MDL Information Systems, Inc.). In particular, the compound names were derived from the structures using the Autonom program as utilized by ChemDraw Ultra or ISIS Draw.

Clinical Applications. The compounds disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Melanocortin receptor-specific compounds of this invention that are MC1-R specific can be used as chemoprevention agents against sun-induced, such as by UV radiation, neoplastic activity in human skin. MC1-R agonist compounds of this invention may be employed to stimulate epidermal melanocytes to produce melanin as well as to convert pheomelanin to eumelanin. Eumelanin, which is dark brown or black pigmentation, is considered more photo-protective than pheomelanin, which is yellow or red pigmentation. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is proposed to result from the same pathway by local production of melanotropic peptide from a POMC gene in the epidermis. Thus, stimulation of eumelanin production and conversion of pheomelanin to eumelanin may be a desirable chemoprevention modality in blocking sun- or UV-induced neoplastic activity in skin. A potent, high-affinity and highly selective MC1-R agonist compound of this invention can accordingly be used as a therapeutic chemoprevention agent for combating harmful sun or UV exposure that induces neoplastic activity in skin melanocytes.

In another embodiment, compounds of this invention, including but not limited to compounds that are MC4-R agonists, partial agonists or functionally inactive may be used as a therapeutic agent to modify energy metabolism and feeding behavior, including treatment of pathologic obesity and related conditions. In addition to use in treatment of patients clinically diagnosed as obese, compounds of this invention may be employed with persons who are above optimal body weight, as an aid in weight loss. Compounds of this invention, including but not limited to MC4-R antagonists, may be used as a therapeutic agent in eating disorders, such as treatment of anorexia and cachexia, which is malnutrition and wasting due to illness. In addition to use in treatment of patients diagnosed with anorexia or cachexia, compounds of this invention may be employed with persons who have below optimal body weight, and in particular with patients desiring to gain additional muscle mass.

In yet another embodiment, compounds of this invention can be used as therapeutic agents for treatment of sexual dysfunction, including treatment of both male erectile dysfunction and female sexual dysfunction.

In yet another embodiment, compounds of this invention may be used as therapeutic agents for treatment of inflammation, including specifically MC1-R, MC3-R and MC5-R agonists.

In yet another embodiment of the invention, compounds of this invention that are MC5-R specific can be used as agents to decrease sebum production, and thus may be efficacious in the treatment of acne and related diseases. The compounds for this application may be conveniently formulated for local administration, as through a gel, lotion, cream or other topical formulation.

In yet another embodiment, compounds of this invention may be employed in the treatment of drug or alcohol dependence, depression, anxiety and related conditions and indications.

Formulations and Administration. The compounds may be formulated by any means, such as those known in the art, including but not limited to tablets, capsules, caplets, suspensions, powders, lyophilized forms and aerosols/aerosolizable formulations and may be mixed and formulated with buffers, binders, stabilizers, anti-oxidants and other agents known in the art. The compounds may be administered by any systemic or partially systemic means such as those known in the art, including but not limited to intravenous injection, subcutaneous injection, administration through mucous membranes, oral administration, dermal administration, skin patches, aerosols and the like.

The invention further provides a pharmaceutical composition that includes a compound of this invention and a pharmaceutically acceptable carrier. The compound of this invention may thus be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is suitable, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, such that the dosage may be formulated so as to effect delivery of a compound of this invention over a period of time.

The compounds of this invention may be in the form of any pharmaceutically acceptable salt. Acid addition salts of the compounds of this invention are prepared in a suitable solvent from the compound and an excess of an acid, such as hydrochloric, hydrobromic, sulfuric, phosphoric, acetic, trifluoroacetic, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The compounds and pharmaceutical compositions of this invention may be administered by injection, which injection may be intravenous, subcutaneous, intramuscular, intraperitoneal or by any other means known in the art. In general, any route of administration by which the compounds of this invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means, of an amount sufficient to bring about the desired therapeutic effect.

One advantageous route of administration is nasal administration, such as by means of a liquid spray, gel or powder. In one route of administration, an aqueous solution is employed, preferably administered by means of a metered delivery device. By "nasal administration" is meant any form of intranasal administration of any of the compounds and pharmaceutical compositions of this invention. Thus in one embodiment, compounds and pharmaceutical compositions of this invention include an aqueous solution, such as a solution including saline, citrate or other common excipients or preservatives, formulated for intranasal administration. In another embodiment, compounds and pharmaceutical compositions of this invention include a dry or powder formulation, formulated for intranasal administration. A preparation for nasal administration can take a variety of forms, such as for administration in nasal drops, nasal spray, gel, ointment, cream, powder or suspension. A variety of dispensers and delivery vehicles are known in the art, including single-dose ampoules, metered dose devices, atomizers, nebulizers, pumps, nasal pads, nasal sponges, nasal capsules, and the like.

The pharmaceutical composition may be in a solid, semi-solid, or liquid form. For a solid form, the compound and other components may be mixed together by blending, tumble mixing, freeze-drying, solvent evaporation, co-grinding, spray-drying, and/or other techniques known in the art. A semi-solid pharmaceutical composition suitable for intranasal administration may take the form of an aqueous or oil-based gel or ointment. For example, the compound and other components can be mixed with microspheres of starch, gelatin, collagen, dextran, polylactide, polyglycolide or other similar materials that form hydrophilic gels. In one embodiment, the microspheres can be internally loaded or coated with compound, which upon administration forms a gel that adheres to the nasal mucosa. In another embodiment, the formulation is liquid, it being understood that this includes, for example, an aqueous solution, an aqueous suspension, an oil solution, an oil suspension, or an emulsion, depending on the physicochemical properties of the compound and other components.

For liquid formulations, excipients necessary or desirable for formulation, stability, and/or bioavailability may be included in the pharmaceutical composition. Exemplary excipients include sugars (such as glucose, sorbitol, mannitol, or sucrose), uptake enhancers (such as chitosan), thickening agents and stability enhancers (such as celluloses, polyvinyl pyrrolidone, starch, and the like), buffers, preservatives, and/or acids and bases to adjust the pH. In one embodiment, an absorption promoting component is included in the pharmaceutical composition. Exemplary absorption promoting components include surfactant acids, such as cholic acid, glycocholic acid, taurocholic acid, and other cholic acid derivatives, chitosan and cyclodextrins.

The pharmaceutical composition may further include optional components such as humectants, preservatives and the like. A humectant or moisturizing agent can be employed to decrease water loss from the pharmaceutical composition and optionally moisturize nasal mucosa. Exemplary humectants include hygroscopic materials such as glycerine, propylene glycol, polyethylene glycol, polysaccharides and the like. Preservatives may be employed, to prevent or limit bacteria and other microbial growth. One such preservative that may be employed is benzalkonium chloride, such as 0.05% benzalkonium chloride. Other preservatives include, for example, benzyl alcohol, methylparaben, propylparaben, butylparaben, chlorobutanol, phenethyl alcohol, phenyl mercuric acetate and the like.

The pharmaceutical composition may also include rheology modifying agents, such as for varying the viscosity of the pharmaceutical composition. Exemplary rheology modify agents include polyers and similar materials, such as sodium carboxymethyl cellulose, algin, carageenans, carbomers, galactomannans, hydroxypropyl methylcellulose, hydroxypropyl cellulose, polyethylene glycols, polyvinyl alcohol, polyvinylpyrrolidone, sodium carboxymethyl chitin, sodium carboxymethyl dextran, sodium carboxymethyl starch, xanthan gum and combinations of the foregoing. Such agents may also act as bioadhesives, to extend the residence time of a compound of the invention within the nasal mucosa.

Depending on the formulation and route of administration, an aqueous solution of compounds or pharmaceutical compositions of this invention may be appropriately buffered by means of saline, acetate, phosphate, citrate, acetate or other buffering agents, which are at any physiologically acceptable pH, generally from about pH 4 to about pH 8. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed.

In another route of administration, compounds and pharmaceutical compositions of this invention are administered directly into the lung. Intrapulmonary administration may be performed by means of a metered dose inhaler, a device allowing self-administration of a metered bolus of a compound and pharmaceutical composition of this invention when actuated by a patient during inspiration. Both dry powder inhalation and nebulized aerosols may be employed. Thus, it is possible and contemplated that compounds and pharmaceutical compositions of this invention may be in a dried and particulate form. In one embodiment, the particles are between about 0.5 and 6.0 μm, such that the particles have sufficient mass to settle on the lung surface and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the constructs may be deposited to the deep lung, thereby providing quick and efficient absorption into the bloodstream. Further, with such an approach, penetration enhancers are not required, as is sometimes necessary with transdermal, nasal or oral mucosal delivery routes. Any of a variety of inhalers may be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 μm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

The compounds and pharmaceutical compositions of this invention may be formulated for and administered by means of an injection, such as a deep intramuscular injection, such as in the gluteal or deltoid muscle, of a time release injectable formulation. In one embodiment, a compound or pharmaceutical composition of this invention is formulated with a PEG, such as poly(ethylene glycol) 3350, and optionally one or more additional excipients and preservatives, including but not limited to excipients such as salts, polysorbate 80, sodium hydroxide or hydrochloric acid to adjust pH, and the like. In another embodiment a compound or pharmaceutical composition of this invention is formulated with a poly(ortho ester), which may be an auto-catalyzed poly(ortho ester) with any of a variable percentage of lactic acid in the polymeric backbone, and optionally one or more additional excipients. In one embodiment, poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining a compound of this invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a time release injectable formulation. The teachings of U.S. Pat. Nos. 4,938,763, 6,432,438, and 6,673,767, and the biodegradable polymers and methods of formulation disclosed therein, are incorporated herein by reference. The formulation may be such that an injection is required on a weekly, monthly or other periodic basis, depending on the concentration and amount of construct, the biodegradation rate of the polymer, and other factors known to those of skill in the art.

Pharmaceutically Effective Amount. In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired effect. This may readily be determined by one of ordinary skill in the art through means such as pharmacokinetic studies, plasma half-life studies, dose escalation studies, and the like. Thus a pharmaceutically effective amount includes an amount of a compound or pharmaceutical composition of this invention that is sufficient to induce the desired effect.

In general, the compounds of this invention are highly active, with dose responses as low as 0.01 μg/kg, generally with optimal or peak dose responses between about 0.01 μg/kg and 25 μg/kg, depending on the specific compound and the route of administration. For example, the compound can be administered at 0.01, 0.05, 0.1, 0.5, 1, 5, 10, 50, 100, or 500 μg/kg body weight, depending on specific compound selected, the desired response, the route of administration, the formulation and other factors known to those of skill in the art. Conventional dose response studies and other pharmacological means may be employed to determine the optimal dose for a desired effect with a given compound, given formulation and given route of administration.

Combination Therapy and Weight Regulation. It is also possible and contemplated to use compounds of this invention in combination with other drugs or agents for treatment of various weight and feeding-related disorders. Compounds of this invention may be employed for decreasing food intake and/or body weight in combination with any other agent or drug heretofore employed as a diet aid, or for decreasing food intake and/or body weight. Compounds of this invention may further be employed for increasing food intake and/or body weight in combination with any other agent or drug heretofore employed for increasing food intake and/or body weight.

Drugs that reduce energy intake include, in part, various pharmacological agents, referred to as anorectic drugs, which are used as adjuncts to behavioral therapy in weight reduction programs. Classes of anorectic drugs include, but are not limited to, noradrenergic and serotonergic agents. Noradrenergic medications may be described as those medications generally preserving the anorectic effects of amphetamines but with weaker stimulant activity. The noradrenergic drugs, except phenylpropanolamine, generally act through a centrally mediated pathway in the hypothalamus that causes anorexia. Phenylpropanolamine, a racemic mixture of norephedrine esters, causes a release of norepinephrine throughout the body and stimulates hypothalamic adrenoreceptors to reduce appetite.

Suitable noradrenergic agents include, but are not limited to, diethylpropion such as TENUATE™ (1-propanone, 2-(diethylamino)-1-phenyl-, hydrochloride) commercially available from Merrell; mazindol (or 5-(p-chlorophenyl)-2,5-dihydro-3H-imidazo[2,1-a]isoindol-5-ol) such as SANOREX™ commercially available from Novartis or MAZANOR™ commercially available from Wyeth Ayerst; phenylpropanolamine (or Benzenemethanol, alpha-(1-aminoethyl)-, hydrochloride); phentermine (or Phenol, 3-[[4,5-duhydro-1H-imidazol-2-yl]ethyl](4-methylphenyl)amino], monohydrochloride) such as ADIPEX-P™ commercially available from Lemmon, FASTIN™ commercially available from Smith-Kline Beecham and Ionamin™ commercially available from Medeva; phendimetrazine (or (2S,3S)-3,4-Dimethyl-2phenylmorpholine L-(+)-tartrate (1:1)) such as METRA™ commercially available from Forest, PLEGINE™ commercially available from Wyeth-Ayerst; PRELU-2™ commercially available from Boehringer Ingelheim, and STATOBEX™ commercially available from Lemmon; phendamine tartrate such as THEPHORIN™ (2,3,4,9-Tetrahydro-2-methyl-9-phenyl-1H-indenol[2,1-c]pyridine L-(+)-tartrate (1:1)) commercially available from Hoffmann-LaRoche; methamphetamine such as DESOXYN™ Tablets ((S)—N, (alpha)-dimethylbenzeneethanamine hydrochloride) commercially available from Abbott; and phendimetrazine tartrate such as BONTRIL™ Slow-Release Capsules (-3,4-Dimethyl-2-phenylmorpholine Tartrate) commercially available from Amarin.

Suitable serotonergic agents include, but are not limited to, sibutramine such as MERIDIA™ capsules (a racemic mixture of the (+) and (−) enantiomers of cyclobutanemethanamine, 1-(4-chlorophenyl)-N,N-dimethyl-(alpha)-(2-methylpropyl)-, hydrochloride, monohydrate) commercially available from Knoll, fenfluramine such as Pondimin™ (Benzeneethanamine, N-ethyl-alpha-methyl-3-(trifluoromethyl)-, hydrochloride) commercially available from Robbins; dexfenfluramine such as Redux™ (Benzeneethanamine, N-ethyl-alpha-methyl-3-(trifluoromethyl)-, hydrochloride) commercially available from Interneuron. Fenfluramine and dexfenfluramine stimulate release of serotonin and inhibit its reuptake. Sibutramine inhibits the reuptake of serotonin, norepinephrine and dopamine, but does not stimulate secretion of serotonin.

Other serotonergic agents useful with the practice of the present invention include, but are not limited to, certain auoretic gene 5HT1a inhibitors (brain, serotonin) such as carbidopa and benserazide as disclosed by U.S. Pat. No. 6,207,699 which is incorporated herein by reference; and certain neurokinin 1 receptor antagonist and selective serotonin reuptake inhibitors including fluoxetine, fluvoxamine, paroxtine, sertraline and other useful compounds as disclosed by U.S. Pat. No. 6,162,805 which is incorporated herein by reference. Other potential agents that may be employed include, for example, 5HT2c agonists.

Other useful compounds for reducing energy intake include, but are not limited to, certain aryl-substituted cyclobutylalkylamines as disclosed by U.S. Pat. No. 6,127,424 which is incorporated herein by reference; certain trifluoromethylthiophenylethylamine derivatives as disclosed by U.S. Pat. No. 4,148,923 which is incorporated herein by reference; certain compounds as disclosed by U.S. Pat. No. 6,207,699 which is incorporated herein by reference; certain kainite or AMPA receptor antagonists as disclosed by U.S. Pat. No. 6,191,117 which is incorporated herein by reference; certain neuropeptide receptor subtype 5 as disclosed by U.S. Pat. No. 6,140,354 which is incorporated herein by reference; and certain alpha-blocking agents as disclosed by U.S. Pat. No. 4,239,763 which is incorporated herein by reference.

Moreover, several peptides and hormones regulate feeding behavior. For example, cholecystokinin and serotonin act to decrease appetite and food intake. Leptin, a hormone produced by fat cells, controls food intake and energy expenditure. In obese persons who are losing weight without medications, a decrease in weight is associated with a decrease in circulating levels of leptin, suggesting its role in weight homeostasis. Obese patients with high leptin levels are thought to have peripheral leptin resistance secondary to the down-regulation of leptin receptors. Non-limiting examples of useful compounds affecting feeding behavior include certain leptin-lipolysis stimulated receptors as disclosed by WO 01/21647 which is incorporated herein by reference; certain phosphodiesterase enzyme inhibitors as disclosed by WO 01/35970 which is incorporated herein by reference; certain compounds having nucleotide sequences of the mahogany gene as disclosed by WO 00/05373 which is incorporated herein by reference; and certain sapogenin compounds as disclosed by U.S. Pat. No. 4,680,289 which is incorporated herein by reference.

Other useful compounds include certain gamma peroxisome proliferator activated receptor (PPAR) agonists as disclosed by WO 01/30343 and U.S. Pat. No. 6,033,656 which are incorporated herein by reference and certain polypeptides such as fibroblast growth factor-10 polypeptides as disclosed by WO 01/18210 which is incorporated herein by reference.

Moreover, monoamine oxidase inhibitors that decrease energy intake or increase energy expenditure are useful with the practice of the present invention. Suitable, but non-limiting, examples of monoamine oxidase inhibitors include befloxatone, moclobemide, brofaromine, phenoxathine, esuprone, befol, toloxatone, pirlindol, amiflamine, sercloremine, bazinaprine, lazabemide, milacemide, caroxazone and other certain compounds as disclosed by WO 01/12176 which is incorporated herein by reference.

Certain compounds that increase lipid metabolism are also useful with the practice of the present invention. Such compounds include, but are not limited to, evodiamine compounds as disclosed by U.S. Pat. No. 6,214,831 which is incorporated herein by reference.

Nutrient partitioning agents and digestive inhibitors are another strategy in the treatment of obesity by interfering with the breakdown, digestion or absorption of dietary fat in the gastrointestinal tract. Gastric and pancreatic lipases aid in the digestion of dietary triglycerides by forming them into free fatty acids that are then absorbed in the small intestine. Inhibition of these enzymes leads to inhibition of the digestion of dietary triglycerides. Non-limiting examples include a lipase inhibitor, orlistat, such as XENICAL™ capsules ((S)-2-formylamino-4-methyl-pentanoic acid (S)-1-[[(2S,3S)-3-hexyl-4-oxo-2-oxetanyl]methyl]-dodecyl ester) commercially available from Roche Laboratories and certain benzoxazinone compounds as described by WO 00/40247 which is incorporated herein by reference.

Agents that increase energy expenditure are also referred to as thermogenic medications. Non-limiting examples of suitable thermogenic medications include xanthines, such as caffeine and theophylline, selective β-3-adrenergic agonists, for example certain compounds in U.S. Pat. No. 4,626,549 which is incorporated by reference herein, and α-2-adrenergic and growth hormones compounds as described in U.S. Pat. Nos. 4,937,267 and 5,120,713 which are incorporated by reference herein.

Generally, a total dosage of the above-described obesity control agents or medications, when used in combination with a compound of this invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

Agents or drugs employed for increasing food intake and/or body weight include appetite stimulants such as megestrol acetate, adrenocorticoids such as prednisolone and dexamethasone, cyproheptidine, serotonergic drugs such as fenfluramine, neuropeptide Y, and androgen antagonists such as flutamide, nilutamide, and zanoterone.

Assays and Animal Models.

Selected compounds were tested in assays to determine binding and functional status, and were tested in animal models of feeding behavior as discussed below. The following assays and animal models were employed, with modifications as discussed in the examples.

Competitive inhibition assay using $[I^{125}]$-NDP-α-MSH. A competitive inhibition binding assay was performed using membrane homogenates prepared from HEK-293 cells that express recombinant hMC4-R, hMC3-R, or hMC5-R, and from B-16 mouse melanoma cells (containing endogenous MC1-R). In some instances, HEK-293 cells that express recombinant hMC1-R were employed. In the examples that follow, all MC3-R, MC4-R and MC5-R values are for human recombinant receptors. MC1-R values are for B-16 mouse melanoma cells, unless the heading is "hMC1-R", in which case the value is for human recombinant MC1-R. Assays were performed in 96 well GF/B Millipore multiscreen filtration plates (MAFB NOB10) pre-coated with 0.5% bovine serum albumin (Fraction V). Membrane homogenates were incubated with 0.2 nM (for hMC4-R) 0.4 nM (for MC3-R and MC5-R) or 0.1 nM (for mouse B16 MC1-R or hMC1-R) $[I^{125}]$-NDP-α-MSH (Perkin Elmer) and increasing concentrations of test compounds in buffer containing 25 mM HEPES buffer (pH 7.5) with 100 mM NaCl, 2 mM CaCl$_2$, 2 mM MgCl$_2$, 0.3 mM 1,10-phenanthroline, and 0.2% bovine serum albumin. After incubation for 60 minutes at 37° C., the assay mixture was filtered and the membranes washed three times with ice-cold buffer. Filters were dried and counted in a gamma counter for bound radioactivity. Non-specific binding was measured by inhibition of binding of $[I^{125}]$-NDP-α-MSH in the presence of 1 μM NDP-α-MSH. Maximal specific binding (100%) was defined as the difference in radioactivity (cpm) bound to cell membranes in the absence and presence of 1 μM NDP-α-MSH. Radioactivity (cpm) obtained in the presence of test compounds was normalized with respect to 100% specific binding to determine the percent inhibition of $[I^{125}]$-NDP-α-MSH binding. Each assay was conducted in triplicate and the actual mean values are described, with results less than 0% reported as 0%. Ki values for test compounds were determined using Graph-Pad Prism® curve-fitting software.

Competitive binding assay using $[I^{125}]$—AgRP (83-132). Competitive binding studies using $[I^{125}]$—AgRP (83-132) were carried out using membrane homogenates isolated from cells that express hMC4-R. The assays were performed in 96-well GF/B Millipore multiscreen filtration plates (MAFB NOB10) pre-coated with 0.5% bovine serum albumin (Fraction V). The assay mixture contained 25 mM HEPES buffer (pH 7.5) with 100 mM NaCl, 2 mM CaCl$_2$, 2 mM MgCl$_2$, 0.3 mM 1,10-phenanthroline, 0.5% bovine serum albumin, membrane homogenates, radioligand $[I^{125}]$—AgRP (83-132) (Perkin Elmer) and increasing concentrations of compounds in a total volume of 200 μL. Binding was measured at radioligand concentrations of 0.2 nM. After incubating for 1 hour at 37° C., the reaction mixture was filtered and washed with assay buffer containing 500 mM NaCl. The dried discs were punched out from the plate and counted on a gamma counter. The total binding of the radioligand did not exceed 10% of the counts added to the reaction mixture. Ki values for test compounds were determined using Graph-Pad Prism® curve-fitting software.

Assay for agonist activity. Accumulation of intracellular cAMP was examined as a measure of the ability of the test compounds to elicit a functional response in HEK-293 cells that express MC4-R. Confluent HEK-293 cells that express recombinant hMC4-R were detached from culture plates by incubation in enzyme-free cell dissociation buffer. Dispersed cells were suspended in Earle's Balanced Salt Solution containing 10 mM HEPES (pH 7.5), 1 mM MgCl$_2$, 1 mM glutamine, 0.5% albumin and 0.3 mM 3-isobutyl-1-methylxanthine (IBMX), a phosphodiesterase inhibitor. The cells were plated in 96-well plates at a density of $0.5 \times 10^5$ cells per well and pre-incubated for 30 minutes. Cells were exposed for 1 hour at 37° C. to test compounds dissolved in DMSO (final DMSO concentration of 1%) at a concentration range of 0.05-5000 nM in a total assay volume of 200 μL. NDP-α-MSH was used as the reference agonist. At the end of the incubation period, cells were disrupted by the addition of 50 μL of lysis buffer (cAMP EIA kit, Amersham) followed by vigorous pipetting. Levels of cAMP in the lysates were determined using a cAMP EIA kit (Amersham). Data analysis was performed by nonlinear regression analysis with Graph-Pad Prism® software. The maximum efficacies of the test compounds were compared to that achieved by the reference melanocortin agonist NDP-αMSH.

Food intake and body weight after IN and IP dosing. Changes in food intake and body weight were evaluated for selected compounds. Male C57BL/6 mice were obtained from Jackson labs (Bar Harbor, Me.). Animals were individually housed in conventional plexiglass hanging cages and maintained on a controlled 12 hour on/off light cycle. Water and pelleted (Harlan Teklad 2018 18% Protein Rodent Diet) food was provided ad libitum. The mice were dosed IP (by intraperitoneal injection) after a 24 hour fast or IN (by intranasal administration) with vehicle or selected compounds (0.1-3 mg/kg, and in some cases up to 10 mg/kg). All animals were dosed once a day (or up to four consecutive days) at the start of the "lights off" period. The changes in food intake for the 4 hour and 20 hour period after dosing relative to control animals administered vehicle were determined. Body weights were determine 4 hours prior to dosing and 20 hours after dosing, and the change in body weight relative to control animals administered vehicle were determined.

Determination of mass and nuclear magnetic resonance analysis. The mass values were determined using a Waters MicroMass ZQ device utilizing a positive mode. Mass determinations were compared with calculated values and expressed in the form of mass weight plus one (M+1 or M+H).

Proton NMR data was obtained using a Bruker 300 MHz spectrometer. The spectra were obtained after dissolving compounds in a deuteriated solvent such as chloroform, DMSO, or methanol as appropriate.

Synthetic Methods of the Invention.

One general strategy includes developing a linear intermediate using chiral building blocks such as amino acid derivatives. The linear intermediate can be cyclized using a Mitsunobo reaction strategy or by spontaneous cyclization through reactive groups such as a reaction between an amine and an ester or between an amine and an aldehyde function. In these cyclizations, the driving force for intramolecular reaction versus intermolecular reaction is the thermodynamically favored reaction forming a six-membered ring structure. In many instances, the methodology incorporates conditions that do not involve inversion or racemization of chiral centers. In some instances where a small percentage of racemate is observed, such as in use of an α-amino aldehyde in certain positions, the desired chiral product is easily purified by methods known in the art, such as flash chromatography on a silica gel column.

The group containing the Q ring is preferably made by use of an aldehyde derivative of a D-amino acid. By use of an α-amino aldehyde the resulting group has, in its most basic form, the general structure:

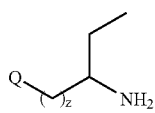

By way of example, where an aldehyde derivative of D-Phe is employed in synthesis, in the resulting compound z is 1, and Q is phenyl. However, it can readily be seen that any D-amino acid listed above may be employed as an aldehyde derivative, and may further be seen that one or both hydrogen atoms in the —NH$_2$ may be substituted by an amine capping group. In synthesis, preferably an N-protected D-amino acid aldehyde is employed, where the N-protecting group is conventionally Boc or Fmoc. Because of the inherent instability of an α-amino aldehyde in solution, these compounds are preferably synthesized immediately prior to use. Two different methods are used for synthesis.

In the first method, to an N-protected amino acid (such as with a Boc- or Fmoc-group) in dichloromethane was added TBTU (1 eq.) (here and elsewhere "eq." is an abbreviation for equivalent or equivalents, as the context requires) and NMM (1 eq.). The mixture was stirred for half an hour and N,O-dimethylhydroxylamine hydrochloride (1 eq.) and NMM (1 eq.) were added. The reaction was carried out overnight. The solvent was removed and EtOAc was added. The organic phase was washed by aqueous sodium bicarbonate, brine and dried over sodium sulfate. After evaporation of solvent and drying under vacuum the residue was dissolved in THF under nitrogen at −78° C. To this solution was added LAH (1 M in THF, 1.5 eq.) slowly. The solution was stirred for an additional half hour. The reaction was diluted by ether and quenched by aqueous potassium hydrogen sulfate. The organic phase was washed with 1 N HCl, water, brine and dried over sodium sulfate. After removal of solvent the aldehyde was used immediately for the next step reaction without purification.

In the second method, to an N-protected amino acid (such as with a Boc- or Fmoc-group) in THF was added borane-THF (1 M, 1.2 eq.) slowly at 0° C. The temperature was raised to room temperature and the solution stirred for 2 hours. The reaction was quenched by 1 N HCl and the solvent was evaporated. The crude product was purified on a silica gel column to give a pure N-protected amino alcohol. This alcohol was dissolved in dry dichloromethane and Dess-Martin periodinane (1.1 eq.) was added. The solution was stirred for 1 hour and the reaction was diluted by ether. The organic phase was washed by saturated sodium bicarbonate with 10% sodium thiosulfate, then water, then brine and dried over sodium sulfate. After removal of solvent the crude product was used for the next step reaction immediately without further purification.

In the synthetic methods employed, either of the foregoing methods may be employed to utilize a D-amino acid aldehyde.

In general, the synthetic methods employed were modifications of those described in applications cited above, including specifically patent application Ser. No. 10/837,519, but employing an amino acid aldehyde, and in most instances a D-amino acid aldehyde.

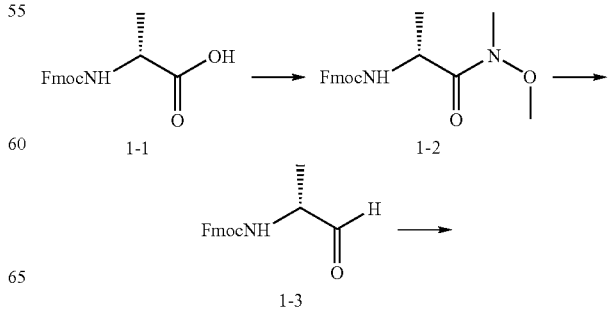

Scheme 1

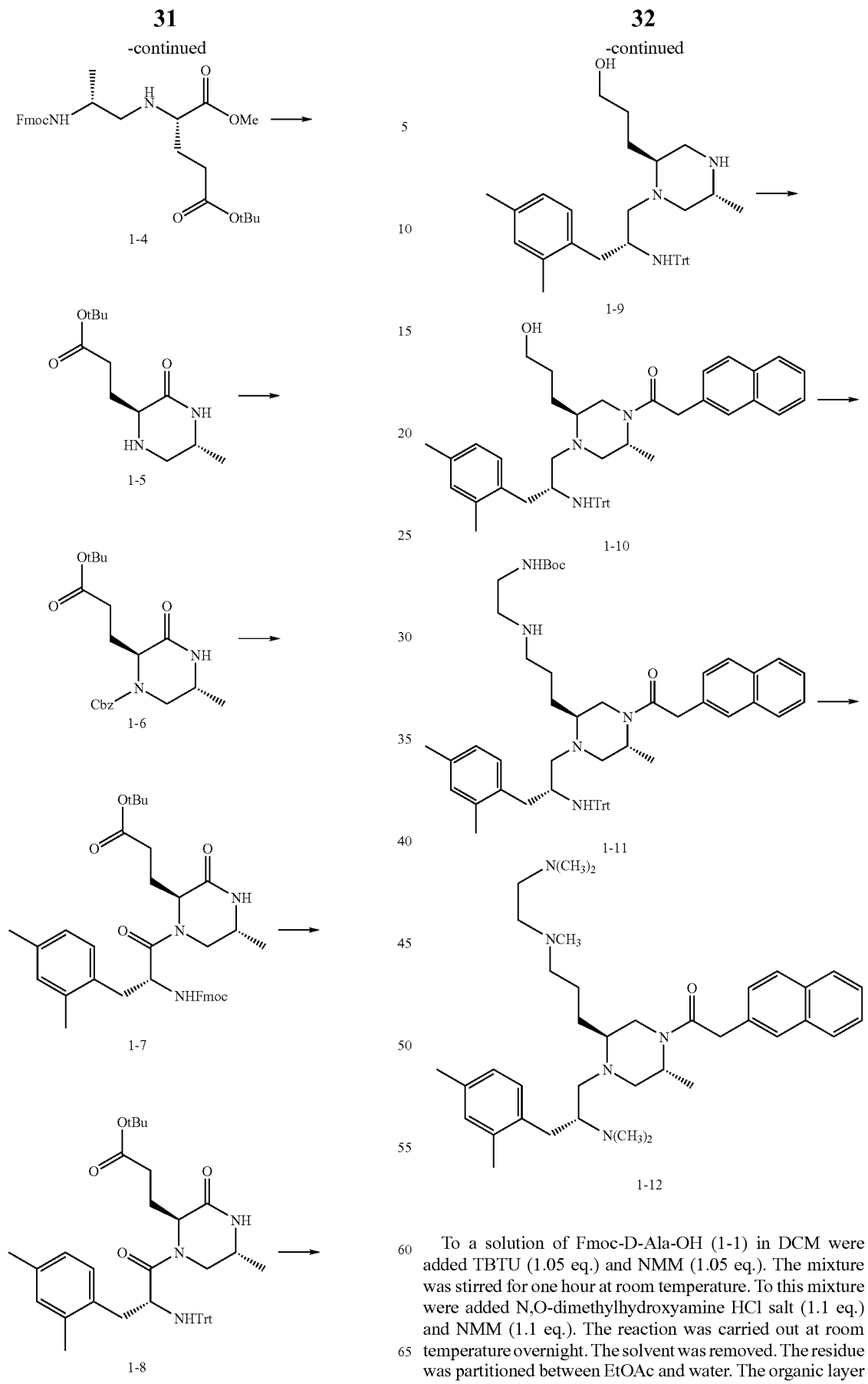

To a solution of Fmoc-D-Ala-OH (1-1) in DCM were added TBTU (1.05 eq.) and NMM (1.05 eq.). The mixture was stirred for one hour at room temperature. To this mixture were added N,O-dimethylhydroxyamine HCl salt (1.1 eq.) and NMM (1.1 eq.). The reaction was carried out at room temperature overnight. The solvent was removed. The residue was partitioned between EtOAc and water. The organic layer was washed by water, 1 N HCl, saturated sodium bicarbonate, brine and dried over sodium sulfate. The solvent was removed and the crude compound 1-2 was used for next step reaction.

Compounds with different groups in the $R_{2a}$ or $R_{2b}$ position may be used by employing Fmoc-NHCH$_2$R$_2$—COOH of the structure

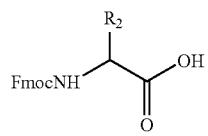

where R$_2$ is the group in position $R_{2a}$ or $R_{2b}$ of Structure I. Thus R$_2$ may be methyl, isobutyl, cyclohexylmethyl, benzyl or any other group as defined for $R_{2a}$ or $R_{2b}$.

To a solution of compound 1-2 in dry THF was added LAH (1.2 eq.) slowly under nitrogen at −78° C. After completion of addition the reaction mixture was stirred at −78 C for one hour. The reaction was quenched by addition of aqueous potassium hydrogen sulfate solution. The mixture was diluted with EtOAc and the solid was removed. The solvent of the filtrate was evaporated. The residue was dissolved in EtOAc and the organic layer was washed by 1 N HCl, water and dried over sodium sulfate. The solvent was removed and the crude product 1-3 was used for next step reaction.

To a suspension of NH$_2$-Glu(OtBu)-OMe HCl salt in THF was added triethyl amine (1 eq.). The mixture was stirred for 30 minutes under nitrogen. To this mixture was added 1-3 in THF, then 4 Å molecular sieves. The mixture was stirred for 2 hours at room temperature and sodium triacetoxy borohydride (1.5 eq.) was added. The reaction was carried out at room temperature overnight. The solids were removed by passing through a Celite pad. The solvent of filtrate was removed and the residue was partitioned between EtOAc and water. The organic layer was collected and dried over sodium sulfate. After removal of solvent the product 1-4 was obtained as a crude compound, which was used for next step reaction without further purification.

Compound 1-4 was dissolved in 30% diethyl amine in EtOAc. The reaction was carried out overnight at room temperature. The solvent was removed and the residue was purified on silica gel column to give pure product 1-5.

Compound 1-5 was dissolved in DCM and triethyl amine (1.5 eq.) was added. To this solution was added benzyl chloroformate (1.2 eq.) at 0° C. The reaction mixture was stirred overnight at room temperature. The solvent was removed from the reaction mixture and the residue was purified on silica gel column to give compound 1-6.

Compound 1-6 was dissolved in ethanol and stirred at one atmosphere of hydrogen in the presence of a catalytic amount of Pd/C (10%). The reaction was carried out at room temperature overnight. The catalyst was removed by filtration. The solvent of the filtrate was removed to give a crude product. To a mixture of Fmoc-D-2,4-di-methyl-phenylalanine (1.5 eq.), HOAt (1.5 eq.) and EDC (1.5 eq.) in DMF was added this crude product. The reaction was carried out at room temperature overnight. The solvent was removed and the residue was dissolved in EtOAc. The organic phase was washed by aqueous sodium bicarbonate, water, brine and dried over sodium sulfate. After removal of solvent the compound was purified on silica gel column to give product 1-7.

Compound 1-7 was treated with 30% diethylamine in EtOAc overnight at room temperature. The solvent was removed and dried under vacuum for 2 hours. This crude product was dissolved in DCM, to which was added TEA (1.2 eq.) and trityl chloride (1.2 eq.) at 0° C. The mixture was stirred at room temperature overnight. Solvent was removed and the compound was purified on silica gel column to give product 1-8.

Compound 1-8 was dissolved in THF. To this solution was added lithium aluminum hydride (4.5 eq.) in THF at 0° C. The mixture was stirred at room temperature for 4 hours and refluxed for 10 hours. The reaction mixture was cooled to 0° C., to which was added water, 15% sodium hydroxide and water sequentially. The solid was removed by filtration. The filtrate solvent was evaporated to give product 1-9.

Compound 1-9 was dissolved in DCM. To this solution was added TEA (2.0 eq.) and 2-naphthylacetyl chloride (2 eq.) at 0° C. The reaction was stirred at 0° C. for one hour and then at room temperature for three days. The reaction mixture was washed with water, brine and dried over sodium sulfate. After removal of solvent the residue was purified on silica gel column to give product 1-10.

Compound 1-10 was dissolved in DCM and Dess-Martin periodinane (1.1 eq.) was added portion-wise. The mixture was stirred at room temperature for 2 hours. The reaction mixture was diluted with ether. This mixture was stirred with a solution of sodium thiosulfate in saturated sodium bicarbonate for 30 minutes. After repeating three times, the organic layer was washed with water, brine and dried over sodium sulfate. The solvent was removed. The residue was dissolved in THF. To this solution was added N—Boc-ethylenediamine (4 eq.) and the mixture was stirred for two hours in the presence of 4 Å molecular sieves. To this mixture was added sodium triacetoxy borohydride (2 eq.) and the reaction was carried out overnight at room temperature. The product was extracted by EtOAc from water. The combined organic solution was washed with water, brine and dried over sodium sulfate. After removal of solvent the residue was purified on silica gel column to give product 1-11.

Compound 1-11 was stirred with TFA in DCM for one hour. After removal of solvent, cold ether was added to the residue. The precipitates was collected and basified with NMM in methanol. The solvent was removed and the residue was dissolved in dichloroethane. To this solution was added formaldehyde (37% aq. solution, 10 eq.). After 10 minutes stirring, sodium triacetoxyborohydride (5 eq.) was added. The mixture was then stirred overnight at room temperature. The reaction was washed with water, brine and dried over sodium sulfate. The solvent was removed and the product was purified by HPLC to give 1-12.

Scheme 2

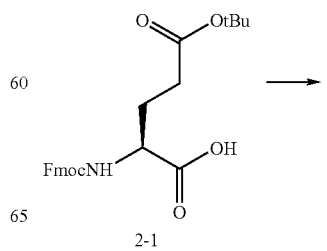

2-1

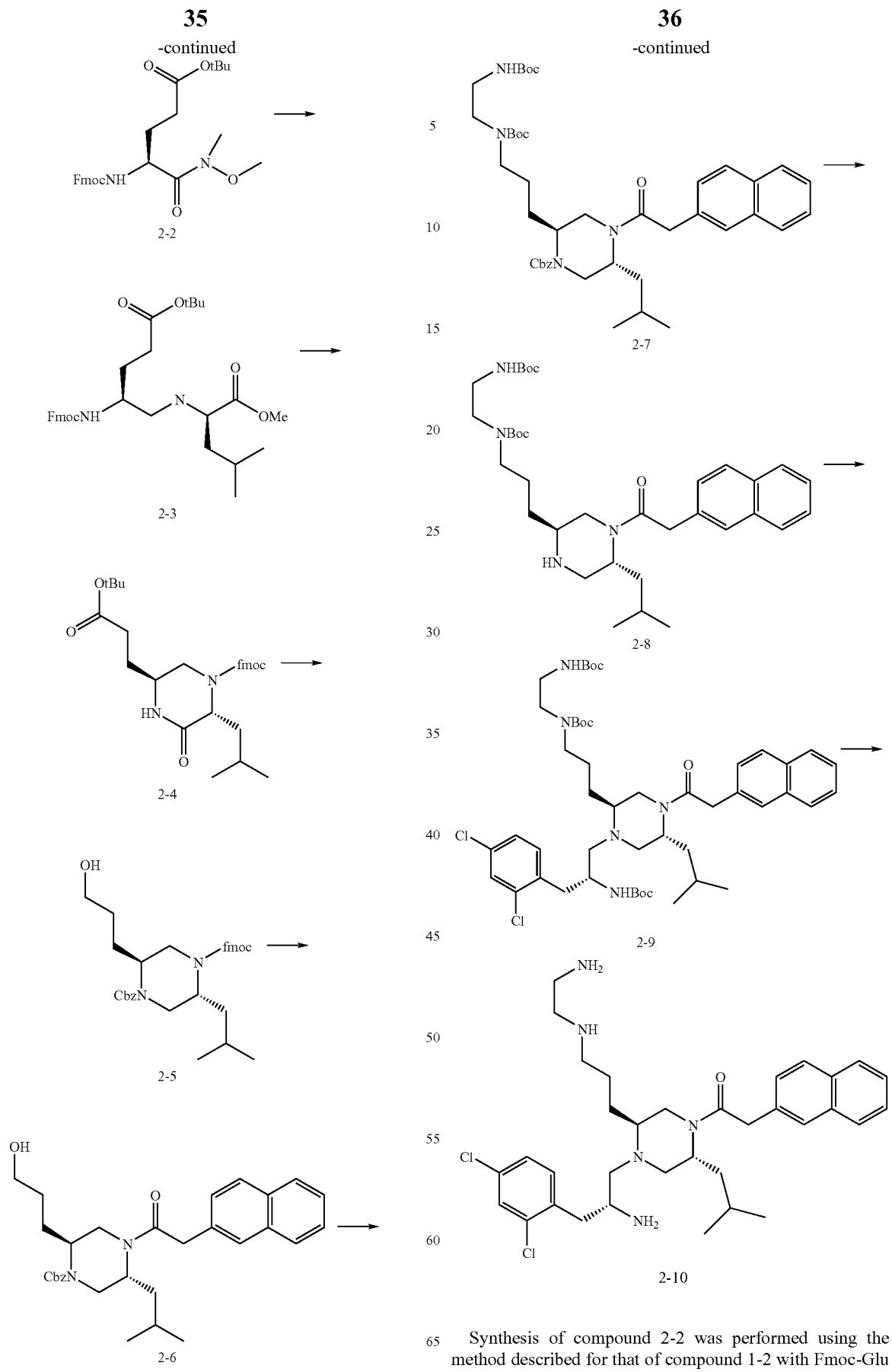
Synthesis of compound 2-2 was performed using the method described for that of compound 1-2 with Fmoc-Glu(OtBu)-OH (2-1) used as starting material.

Synthesis of compound 2-3 was performed using the method described for that of compound 1-3 and 1-4, with NH$_2$-D-Leu-OMe (NH$_2$—CH(R$_2$)—COOMe) used as one of the starting materials.

Compound 2-3 was dissolved in 30% diethyl amine in EtOAc. The reaction was carried out overnight at room temperature. The solvent was removed and the residue was dissolved in THF. To the solution was added 9-fluorenylmethyl chloroformate (1.2 eq.), followed by water and sodium bicarbonate (5 eq.). After stirring at room temperature for 90 minutes EtOAc and water were added. The organic layer was separated and washed with water and dried over sodium sulfate. The solvent was removed and residue was purified on silica gel column to give pure product 2-4.

To a solution of compound 2-4 in 350 mL of THF was added borane-THF (2.8 eq.) slowly at 0° C. The reaction was carried out at room temperature overnight. Additional amounts of borane-THF (1.4 eq.) were added and reaction mixture was stirred overnight. The mixture was cooled to 0° C. and 1 N HCl was added to adjust the pH to 2-3. This mixture was stirred overnight at room temperature. The pH were adjusted to 7-8 by sodium bicarbonate before addition of sodium bicarbonate (5 eq.), water and benzyl chloroformate (1.2 eq.). The reaction was stirred for 2 hours. Additional amounts of benzyl chloroformate (0.6 eq.) and sodium bicarbonate (2.5 eq.) were added. The reaction was carried out overnight at room temperature. EtOAc and water were added. The organic layer was washed by water until neutral pH was obtained and then dried over sodium sulfate. After removal of solvent the residue was purified on a silica gel column to give pure product 2-5.

Compound 2-5 was treated with 30% diethyl amine in EtOAc overnight at room temperature. After removal of solvent the residue was purified to give a product, which was dissolved in THF. To this solution was added triethyl amine (5 eq.), followed by 2-naphthyl acetyl chloride (Q-COOH) (4 eq.) in THF at 0° C. The reaction mixture was stirred at 0° C. for 1 hour and then room temperature overnight. The solvent was removed and the residue was treated with lithium hydroxide in methanol/THF/water for 60 hours. The product was extracted by ether four times. The combined organic layer was washed with water, brine and dried over sodium sulfate. After removal of solvent the residue was purified to give product 2-6.

Compound 2-6 was dissolved in DCM and Dess-Martin periodinane (1.1 eq.) was added portion-wise. The mixture was stirred at room temperature for 2 hours. The reaction mixture was diluted with ether. This mixture was stirred with a solution of sodium thiosulfate in saturated sodium bicarbonate for 30 minutes. After repeating three times the organic layer was washed with water, brine and dried over sodium sulfate. The solvent was removed. The residue was dissolved in THF. To this solution was added N—Boc-ethylenediamine (4 eq.) and the mixture stirred for two hours in the presence of 4 Å molecular sieves. To this mixture was added sodium triacetoxy borohydride (2 eq.) and the reaction was carried out overnight at room temperature. The product was extracted by EtOAc from water. The combined organic solution was washed with water and brine. The solvent was removed and the residue was dissolved in THF/water (2/1, v/v). To this solution were added di-t-butyl dicarbonate (4 eq.) and sodium bicarbonate (6 eq.). The mixture was stirred overnight at room temperature. EtOAc was added and the organic layer was washed by water and brine and dried over sodium sulfate. After removal of solvent the residue was purified on a silica gel column to give product 2-7.

Compound 2-7 was dissolved in ethanol and a catalytic amount of Pd/C (10%) was added. The mixture was treated with hydrogen under atmosphere pressure overnight at room temperature. After filtration the filtrate solvent was removed. The resulting compound 2-8 was used for the next step reaction without further purification.

Boc-D-2,4-diCl-D-Phe-OH was dissolved in THF at 0° C. Borane-THF (2 eq.) was added slowly. The solution was stirred for 4 hours and quenched by adding water. The solvent was removed and EtOAc was added, which was washed with 0.5 N HCl, water and brine and dried over sodium sulfate. After removal of solvent, an amino alcohol was used for the next step reaction. To a solution of the selected amino alcohol in dichloromethane was added Dess-Martin periodinane (1.2 eq.) in portions at room temperature. The solution was diluted with ether after 2 hours. To this reaction mixture was added saturated aqueous sodium bicarbonate and sodium thiosulfate. The organic layer was separated. The treatment with sodium bicarbonate and sodium thiosulfate was repeated, and the organic layer was washed with water (three times), brine and dried over sodium sulfate. The solvent was removed under vacuum and the crude aldehyde Boc-D-2,4-diCl-D-Phe-H was used immediately for the next step reaction without further purification.

The aldehyde (2 eq.) and compound 2-8 was mixed in THF in the presence of 4 Å molecular sieves. It was stirred for two hours and then sodium triacetoxy borohydride (2 eq.) was added in one portion. The mixture was stirred at room temperature overnight. After filtration to remove the solids, the filtrate was diluted with EtOAc and washed by water. The organic phase was separated and solvent was removed. The residue was purified on a silica gel column to give compound 2-9.

Compound 2-9 was treated with TFA/DCM (2/1) for 2 hours at room temperature. The solvent was removed and the residue was purified by HPLC to give compound 2-10.

Scheme 3

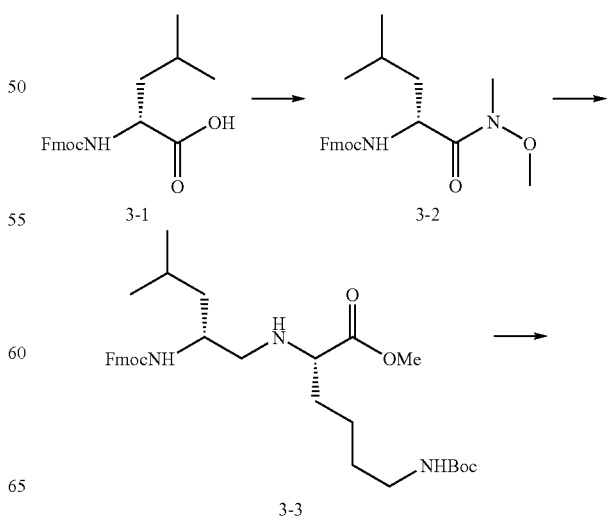

39
-continued
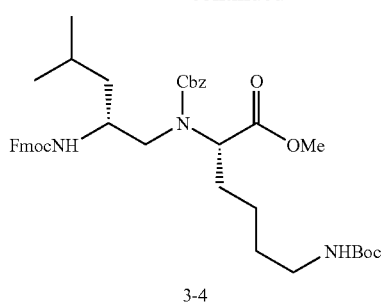
3-4
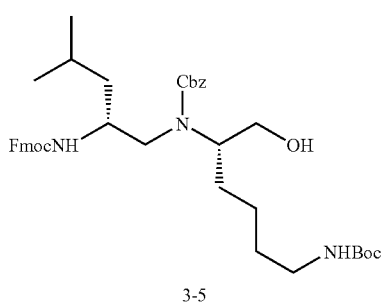
3-5
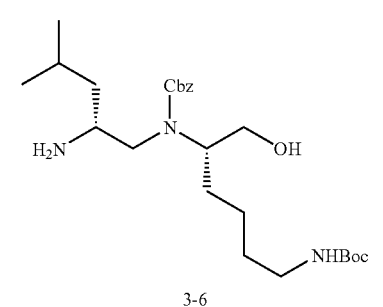
3-6
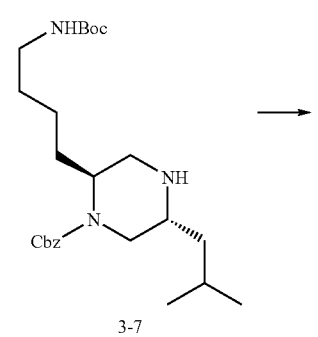
3-7
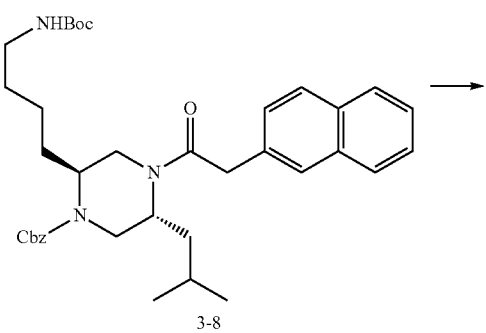
3-8
40
-continued
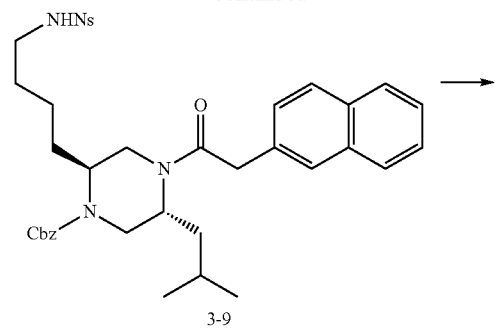
3-9
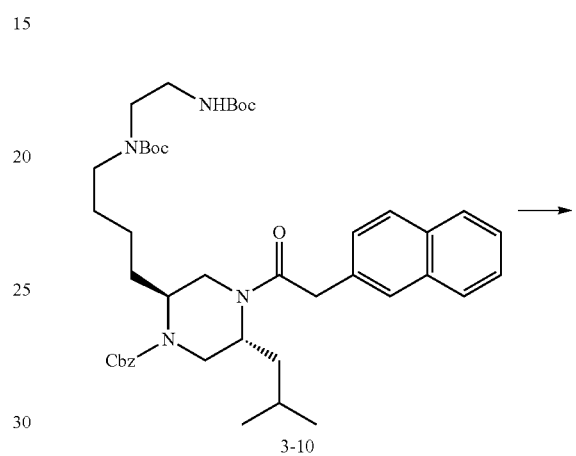
3-10
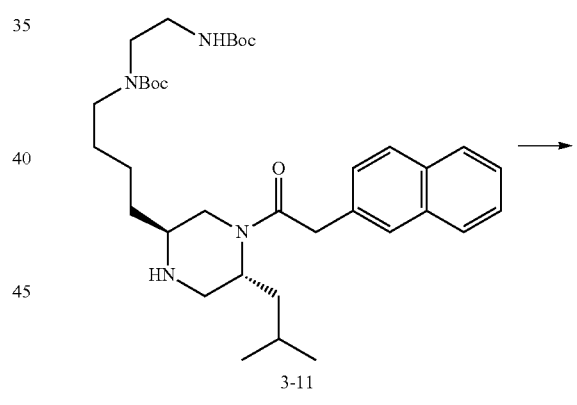
3-11
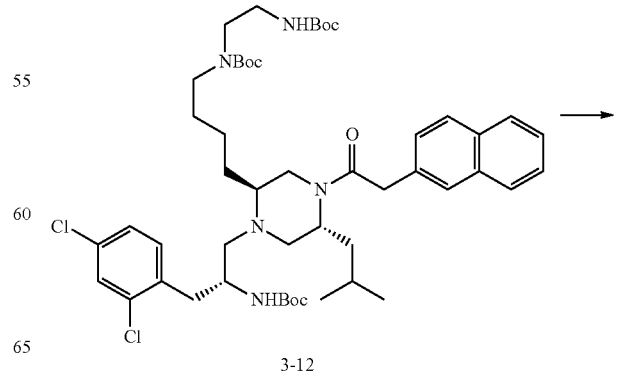
3-12

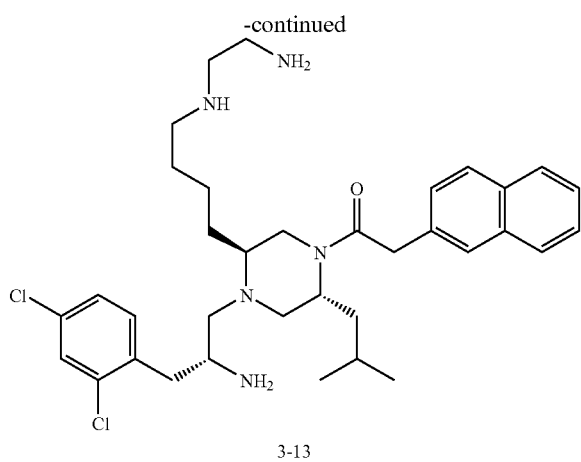

3-13

The syntheses of 3-2 and 3-3 used the methods as described for 2-2 and 2-3. The starting materials were Fmoc-D-Leucine (2-1) and NH$_2$-Lys(Boc)-OMe (NH$_2$—CH(R$_2$)—COOMe).

Compound 3-3 was dissolved in THF/water (v/v=2/1) and sodium bicarbonate (5 eq.) was added. To this mixture at 0° C. was added benzyl chloroformate (2 eq.). The mixture was stirred at room temperature for 2 hours. The organic solvent was removed and EtOAc was added to extract the product. After evaporation of EtOAc, the residue was purified on a column to give compound 3-4.

Compound 3-4 was dissolved in 500 mL of ethyl ether. To this solution was added lithium borohydride (1.5 eq.) slowly in portions while stirring vigorously. There were precipitates formed during the addition. After completion, methanol (1.5 eq.) was added slowly to the reaction mixture. The reaction was monitored by TLC and HPLC until no starting material left. The reaction was quenched with water. The ether layer was separated and washed by brine and dried over sodium sulfate. After removal of solvent the crude product 3-5 was treated with 25% diethylamine in EtOAc over night at room temperature. The solvent was removed and the residue purified on a silica gel column (hexane:EtOAc=1:1, EtOAc, then 25% methanol and 1% ammonium hydroxide in EtOAc) to give product 3-6.

Compound 3-6 and TPP (3 eq.) was dissolved in toluene, which was cooled to −15° C. To this solution was added slowly DIAD (2 eq.) in toluene. The reaction was continued overnight at room temperature. The solvent was removed. To the residue were added heptane and ether (v:v=1). After one hour the precipitate was removed by filtration. The filtrate solvent was removed and the residue was purified on a silica gel column to give product 3-7.

2-Naphthylacetic acid (Q-COOH) (2 eq.) and NMM (2 eq.) were dissolved in dry DCM at −15° C. To this solution was added IBCF (2 eq.) in DCM slowly. After completion, the solution was stirred for an additional one hour. To this solution was added compound 3-7 in DCM at −15° C. The mixture was stirred for one hour at −15° C. and the temperature gradually raised to room temperature and the reaction continued overnight. After removal of solvent the residue was purified on a silica gel column to give compound 3-8.

Compound 3-8 was treated with 25% TFA in DCM for one hour. The solvent was removed at room temperature. To the residue was added EtOAc, and then washed by saturated aqueous sodium bicarbonate solution, brine and dried over sodium sulfate. The solvent was removed and the crude compound was dried under vacuum for 6 hours. To a flask containing 2-nitrophenylsulfonyl chloride (2 eq.) in dry DCM at −78° C. was added a solution of the crude compound and pyridine (1 eq.) slowly. The reaction was carried out overnight. The solvent was removed and EtOAc was added. The organic phase was washed with 1 N HCl, brine and dried over sodium sulfate. After removal of solvent, the residue was purified on a column to give compound 3-9.

A solution of compound 3-9, N—Boc-ethanolamine (3 eq.) and TPP (3 eq.) in toluene was cooled to 0° C. To this solution was added slowly a solution of DIAD (3 eq.) in toluene. The mixture was stirred at 0° C. for one hour, then overnight at room temperature. After removal of solvent, EtOAc was added. The organic phase was washed with saturated sodium bicarbonate and brine and dried over sodium sulfate. The solvent was removed and the product purified on a silica gel column. The resulting compound was treated with 4-thiophenol (4.5 eq.) and potassium carbonate (6 eq.) overnight. The solvent was removed and the residue dissolved in THF/water in the presence of sodium bicarbonate (5 eq.). Di-t-butyl dicarbonate (2 eq.) was added in portions. The mixture was stirred for 4 hours. Organic solvent was removed and the aqueous solution was extracted by EtOAc. After removal of solvent the residue was purified on a column to give compound 3-10.

Compound 3-10 was subjected to a hydrogenolysis reaction in methanol in the presence of a catalytic amount of Pd/C and at atmospheric pressure hydrogen. The reaction was carried out overnight. After filtration to remove the catalysts, the solvent was evaporated from the filtrate. The resulting compound 3-11 was used for the next step reaction without purification.

Syntheses of 3-12 and 3-13 used the methods described for 2-9 and 2-10 with the product purified by HPLC to give compound 3-13.

Scheme 4

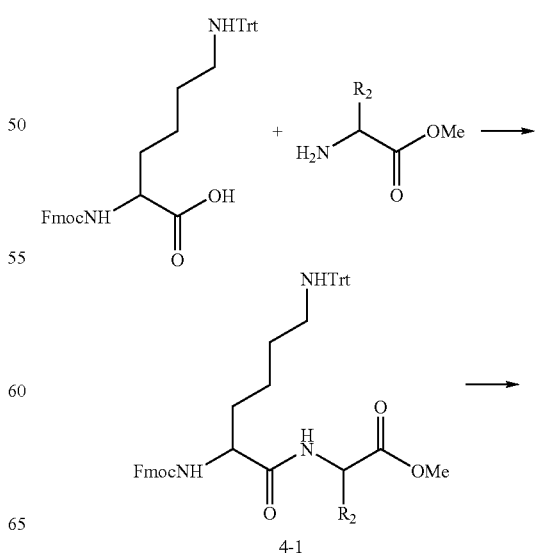

4-1

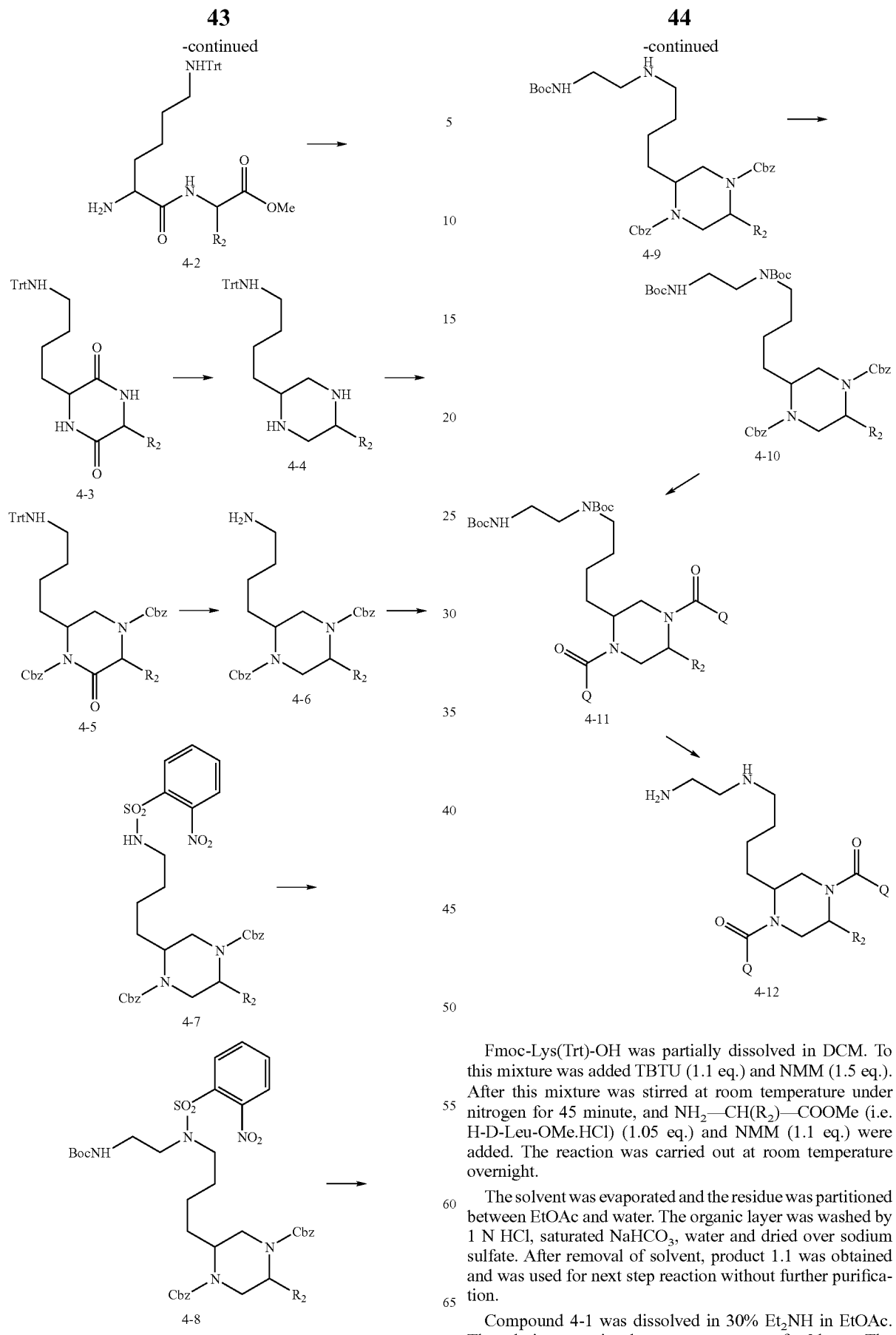

Fmoc-Lys(Trt)-OH was partially dissolved in DCM. To this mixture was added TBTU (1.1 eq.) and NMM (1.5 eq.). After this mixture was stirred at room temperature under nitrogen for 45 minute, and $NH_2$—$CH(R_2)$—COOMe (i.e. H-D-Leu-OMe.HCl) (1.05 eq.) and NMM (1.1 eq.) were added. The reaction was carried out at room temperature overnight.

The solvent was evaporated and the residue was partitioned between EtOAc and water. The organic layer was washed by 1 N HCl, saturated $NaHCO_3$, water and dried over sodium sulfate. After removal of solvent, product 1.1 was obtained and was used for next step reaction without further purification.

Compound 4-1 was dissolved in 30% $Et_2NH$ in EtOAc. The solution was stirred at room temperature for 2 hours. The solvent was removed. The crude product 4-2 was used for next step reaction without further purification.

Compound 4-2 was partially dissolved in dry DMF. The mixture was heated at 90° C. under nitrogen for three days. The reaction was stopped and DMF was removed under vacuum. This crude product was purified on silica gel column eluted with EtOAc/heptane (1:1), DCM, and subsequently MeOH/DCM (9:1). The final product 4-3 was collected after evaporation of solvent.

Compound 4-3 was suspended in THF at 0° C. under nitrogen. To this suspension was added LAH (3.5 eq.) dropwise. The suspension became a clear solution after addition of LAH was completed. The reaction was stirred at room temperature for 45 minutes and refluxed overnight. The reaction mixture was quenched by addition of water, 15% NaOH and water, in sequence at 0° C. The mixture was stirred for 20 minutes at room temperature. The solid was removed by filtration and washed with ether, with ether evaporated to give the crude product 4-4.

Compound 4-4 was dissolved in THF. To this solution benzyl chloroformate (3 eq.) was added, and followed by water and sodium bicarbonate (5 eq.). The reaction mixture was stirred at room temperature for 3 hours. To this mixture water and EtOAc was added. The organic layer was separated and washed by water till the aqueous layer reached neutral pH. The organic layer was dried over sodium sulfate. The solvent was evaporated and the residue was purified on silica gel column eluted with EtOAc/heptane (1:4) to give product 4-5.

Compounds 4-5 was dissolved in a solution of 5% TFA/1% TIS/DCM, and the mixture stirred for 1 hour. The reaction mixture was diluted with DCM. The organic phase was washed with saturated sodium bicarbonate, water, brine and dried over sodium sulfate. After evaporation of solvent the crude product 4-6 was used for next step reaction.

Compound 4-6 was dissolved in DCM. To this solution was added pyridine (10 eq.), and then 2-nitrobenzenesulfonyl chloride (2 eq.) slowly at 0° C. The temperature was raised to room temperature and stirred overnight. The solvent was removed. The residue was dissolved in EtOAc, which was washed by 1N HCl, water, brine and dried over sodium sulfate. After removal of solvent, the residue was purified on silica gel column eluted with 25% EtOAc in heptane. After removal of solvent, compound 4-7 was obtained.

Compound 4-7, TPP (3 eq.) and N—Boc-2-hydroxy-ethylamine (3 eq.) were dissolved in dry toluene. To this solution was added DIAD (3 eq.) in toluene at 0° C. The temperature was raised to room temperature after 30 minutes and the solution was stirred overnight. The solvent was removed and the residue purified on silica gel column eluted with 50% EtOAc in heptane. Compound 4-8 was obtained after removal of solvent.

Compound 4-8 was dissolved in dry acetonitrile. To this solution was added potassium carbonate (6 eq.) and 4-mercaptophenol (4.5 eq.). The mixture was stirred overnight at room temperature. The solvent was removed, and the residue partitioned with EtOAc and water. The organic layer was separated and washed by water, brine and dried over sodium sulfate. The crude compound 4-9 was used for next step reaction.

Compound 4-9 was dissolved in THF/water (2:1). To this solution sodium bicarbonate (5 eq.) and di-t-butyl carbonate (2 eq.) were added subsequently. The mixture was stirred overnight at room temperature. After removal of THF, EtOAc was added to extract the product. The organic layer was washed with 1 N HCl, water, brine and dried over sodium sulfate. The solvent was removed and the residue purified on silica gel column eluted with 25% EtOAc in heptane. Product 4-10 was obtained after removal of solvent.

Compound 4-10 was treated with catalytic amounts of Pd on carbon in ethanol under hydrogen (1 atm.) overnight at room temperature. After filtration through a Celite pad, the solvent was removed. The crude product was dried under vacuum and it was used for next step reaction without further purification.

Q-COOH (i.e. Boc-D-2-Naphthylalanine) (4 eq.), EDC (4 eq.) and HOAt (4 eq.) were dissolved in DMF. The mixture was stirred at 0° C. for 30 minutes. To this solution was added Compound 4-10 in one portion. The reaction was carried out overnight at room temperature. The solvent was removed and the residue was purified on silica gel column to give product 4-11.

Compound 4-11 was treated with TFA for 3 hours at room temperature. After removal of solvent the residue was purified by HPLC to give product 4-12.

Scheme 5

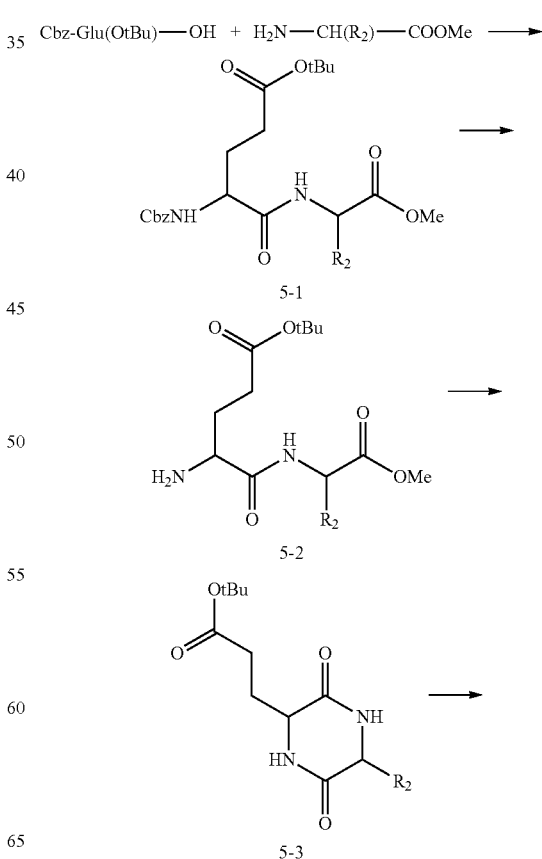

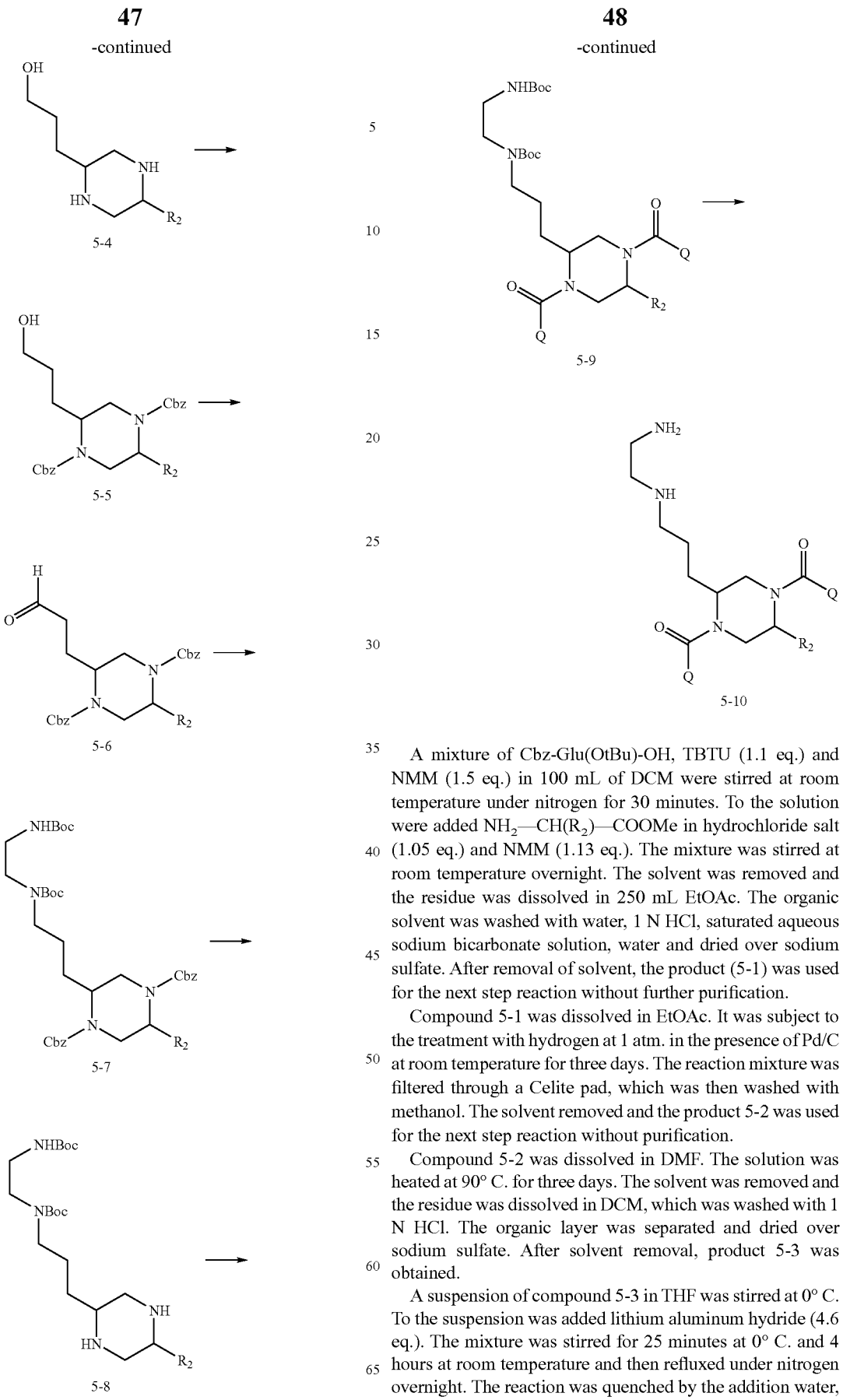

A mixture of Cbz-Glu(OtBu)-OH, TBTU (1.1 eq.) and NMM (1.5 eq.) in 100 mL of DCM were stirred at room temperature under nitrogen for 30 minutes. To the solution were added $NH_2$—$CH(R_2)$—COOMe in hydrochloride salt (1.05 eq.) and NMM (1.13 eq.). The mixture was stirred at room temperature overnight. The solvent was removed and the residue was dissolved in 250 mL EtOAc. The organic solvent was washed with water, 1 N HCl, saturated aqueous sodium bicarbonate solution, water and dried over sodium sulfate. After removal of solvent, the product (5-1) was used for the next step reaction without further purification.

Compound 5-1 was dissolved in EtOAc. It was subject to the treatment with hydrogen at 1 atm. in the presence of Pd/C at room temperature for three days. The reaction mixture was filtered through a Celite pad, which was then washed with methanol. The solvent removed and the product 5-2 was used for the next step reaction without purification.

Compound 5-2 was dissolved in DMF. The solution was heated at 90° C. for three days. The solvent was removed and the residue was dissolved in DCM, which was washed with 1 N HCl. The organic layer was separated and dried over sodium sulfate. After solvent removal, product 5-3 was obtained.

A suspension of compound 5-3 in THF was stirred at 0° C. To the suspension was added lithium aluminide hydride (4.6 eq.). The mixture was stirred for 25 minutes at 0° C. and 4 hours at room temperature and then refluxed under nitrogen overnight. The reaction was quenched by the addition water, 15% sodium hydroxide and water at 0° C. The mixture was stirred at room temperature for an additional 30 minutes. The solid was removed by filtration and washed with ether. The solvent was removed and dried under vacuum to give the crude compound 5-4.

Compound 5-4 was dissolved in THF. To this solution was added benzyl chloroformate (2.5 eq.) followed by water and sodium bicarbonate (6 eq.), such that the ratio of THF to water was 2 to 1. The mixture was stirred overnight at room temperature. To this mixture were added EtOAc and water. The organic layer was washed with water and dried over sodium sulfate. The solvent was removed and the residue was dissolved in methanol and 1 N sodium hydroxide (3 eq.). The reaction was carried out at room temperature for three days. The solvent was removed and the resulted residue was dissolved in EtOAc. The organic phase was washed with 1 N HCl, water, aqueous sodium bicarbonate and dried over sodium sulfate. The solvent was removed and the residue purified on a silica gel column to give product 5-5.

Compound 5-5 was dissolved in DCM. To this solution was added Dess-Martin periodinane (1.1 eq.). The reaction was continued at room temperature for 1.5 hours. Ether was added to dilute the mixture and the reaction was quenched by addition of a solution of sodium thiosulfate in saturated sodium bicarbonate. The organic layer was washed with the same solution and dried over sodium sulfate. After removal of solvent the crude product 5-6 was used for next step reaction without further purification.

To a solution of compound 5-6 and N-Boc-ethylenediamine (1.05 eq.) in THF was added molecular sieves. The mixture was stirred for 3 hours at room temperature. To this mixture was added sodium triacetoxyborohydride (1.5 eq.). The reaction mixture was stirred at room temperature overnight, and the solid removed by filtration. After the solvent was removed the residue was partitioned between EtOAc and water, the organic layer separated and the water layer extracted with EtOAc. The combined organic layer was dried over sodium sulfate. After removal of solvent the residue was dissolved in THF and water (v:v=2:1). To this solution were added di-t-butyl dicarbonate (1.2 eq.) and sodium bicarbonate (5 eq.). The mixture was stirred overnight at room temperature. EtOAc was added and the organic layer was washed with water and dried over sodium sulfate. After removal of solvent the residue was purified on silica gel column to give product 5-7.

Compound 5-7 was dissolved in ethanol and treated with hydrogen under atmosphere pressure in the presence of a catalytic amount of Pd/C. The reaction was carried out overnight at room temperature. The solid was filtered and washed with ethanol several times. The solvent was removed to give product 5-8.

To a solution of Q-COOH (4 eq.) in DMF was added HOAT (4 eq.) and EDC (4 eq.) at 0° C. After the mixture was stirred for 30 minutes, compound 5-8 was added to this mixture. The reaction was continued overnight at room temperature. The solvent was removed and the residue was purified on a silica gel column to give product 5-9.

Compound 5-9 was treated by TFA for three hours at room temperature. After removal of solvent, the residue was purified by HPLC to give compound 5-10.

Representative Compounds of the Invention

EXAMPLE 1

(R)-2-Amino-1-[(2S,5R)-2-[4-(2-amino-ethylamino)-butyl]-5-isobutyl-4-(2-naphthalen-2-yl-acetyl)-piperazin-1-yl]-3-(2,4-dichloro-phenyl)-propan-1-one The following compound was synthesized by the method of Scheme 3 using 2-naphthylacetic acid as J-COOH, Fmoc-D-Leu-OH as Fmoc-NHCH$_2$R$_2$—COOH, and Boc-D-2,4-dichloro-phenylalanine as Q-COOH. In step 3-11, the synthetic method of step 4-11 was employed. Following purification, the compound was tested as described above with the results shown. The mass was analyzed as 639.7 (M+H).

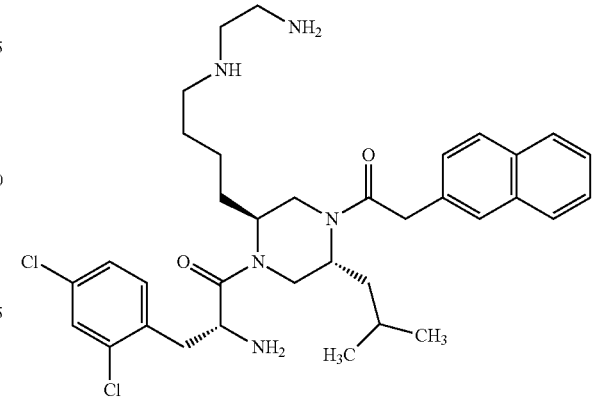

| MC1-R | MC3-R | MC4-R | MC5-R |
|---|---|---|---|
| Inhibition at 1 μM (NDP-α-MSH) | | | |
| 55% | 71% | 98% | 68% |
| Ki (nM) (NDP-α-MSH) | | | |
| 102 | 250 | 18 | 301 |

In a cAMP assay for determination of functionality in a cell line that expresses MC4-R, the maximum effect observed with the compound was 61% of the maximum achieved with NDP-α-MSH.

EXAMPLE 2

1-{(2R,5S)-4-[(R)-2-Amino-3-(2,4-dichloro-phenyl)-propyl]-5-[4-(2-amino-ethylamino)-butyl]-2-isobutyl-piperazin-1-yl}-2-naphthalen-2-yl-ethanone The following compound was synthesized by the method of Scheme 3 using 2-naphthylacetic acid as J-COOH, Fmoc-D-Leu-OH as Fmoc-NHCH$_2$R$_2$—COOH, and Boc-D-2,4-dichloro-phenylalanine as Q-COOH. Following purification, the compound was tested as described above with the results shown. The mass was analyzed as 625.8 (M+H).

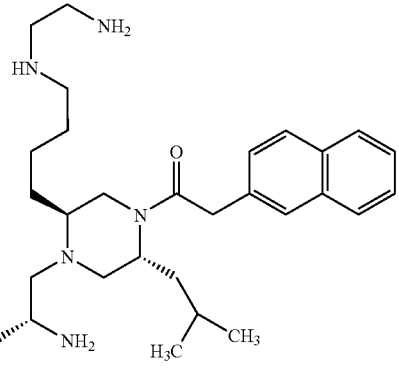

| MC1-R | MC3-R | MC4-R | MC5-R |
|---|---|---|---|
| Ki (nM) (NDP-α-MSH) | | | |
| 558 | 190 | 23 | 143 |
| Ki (nM) (AgRP) | | | |
| | ND | 72 | |

In a cAMP assay for determination of functionality in a cell line that expresses MC4-R, the maximum effect observed with the compound was 16% of the maximum achieved with NDP-α-MSH.

In mouse model IP feeding studies in fasted animals at a 3 mg/kg dose level, an average decrease in food intake of 28% compared to control animals was observed at 20 hours.

In mouse model IN feeding studies at a 0.1, 0.3 and 1 mg/kg dose level, an average decrease in body weight of 2.5%, 3% and 4.7%, respectively, compared to control animals was observed at 20 hours.

EXAMPLE 3

1-{(2R,5S)-4-[(R)-2-Amino-3-(2,4-dichloro-phenyl)-propyl]-5-[4-(2-amino-ethylamino)-butyl]-2-isobutyl-piperazin-1-yl}-2-naphthalen-2-yl-ethanone The following compound was synthesized by the method of Scheme 1. 1-11 was treated by TFA/DCM to give product. Following purification, the compound was tested as described above with the results shown. The mass was analyzed as 530.4 (M+H).

EXAMPLE 4

1-{(2R,5S)-4-[(R)-2-Amino-3-(2,4-dimethyl-phenyl)-propyl]-5-[3-(2-amino-ethylamino)-propyl]-2-methyl-piperazin-1-yl}-2-naphthalen-2-yl-ethanone The following compound was synthesized by the method of Scheme 1. 1-Boc-piperizine was used for the synthesis of 1-11, which was treated by TFA/DCM to give product. Following purification, the compound was tested as described above with the results shown. The mass was analyzed as 556.4 (M+H).

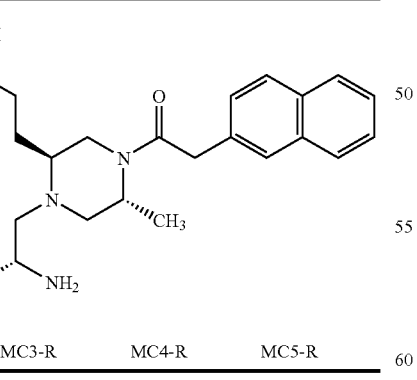

| MC1-R | MC3-R | MC4-R | MC5-R |
|---|---|---|---|
| Inhibition at 1 μM (NDP-α-MSH) | | | |
| 41% | 82% | 92% | 94% |
| Ki (nM) (NDP-α-MSH) | | | |
| 660 | 320 | 160 | 20 |

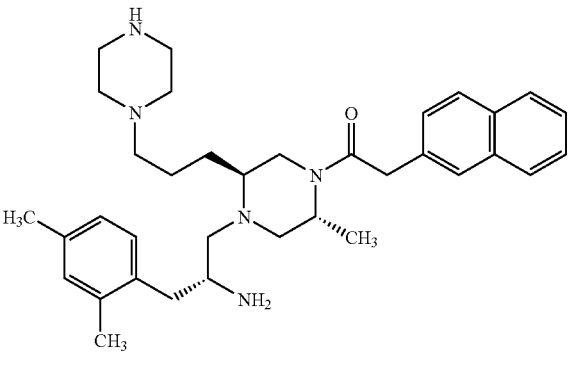

Inhibition at 1 μM (NDP-α-MSH)

| MC1-R | MC3-R | MC4-R | MC5-R |
|---|---|---|---|
| 12% | 43% | 55% | 97% |

EXAMPLE 5

1-{(2R,5S)-4-[(R)-2-Amino-3-(2,4-dimethyl-phenyl)-propyl]-2-methyl-5-[3-(pyrrolidin-3-ylamino)-propyl]-piperazin-1-yl}-2-naphthalen-2-yl-ethanone The following compound was synthesized by the method of Scheme 1. 1-Boc-imidazolidine was used for the synthesis of 1-11, which was treated by TFA/DCM to give product. Following purification, the compound was tested as described above with the results shown. The mass was analyzed as 556.4 (M+H).

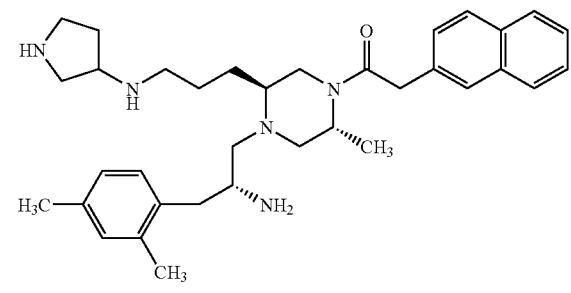

| MC1-R | MC3-R | MC4-R | MC5-R |
|---|---|---|---|
| Inhibition at 1 μM (NDP-α-MSH) | | | |
| 41% | 75% | 81% | 96% |
| Ki (nM) (NDP-α-MSH) | | | |
| 685 | 395 | 387 | 31 |

EXAMPLE 6

1-{(2R,5S)-5-[3-(2-Amino-cyclohexylamino)-propyl]-4-[(R)-2-amino-3-(2,4-dimethyl-phenyl)-propyl]-2-methyl-piperazin-1-yl}-2-naphthalen-2-yl-ethanone The following compound was synthesized by the method of Scheme 1. N-1-Boc-1,2-diaminocyclohexane was used for the synthesis of 1-11, which was treated by TFA/DCM to give product. Following purification, the compound was tested as described above with the results shown. The mass was analyzed as 584.4 (M+H).

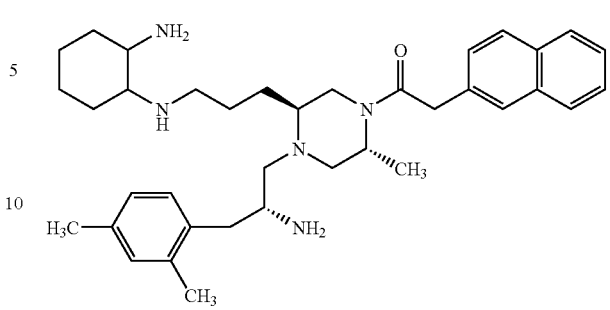

| MC1-R | MC3-R | MC4-R | MC5-R |
|---|---|---|---|
| Inhibition at 1 μM (NDP-α-MSH) | | | |
| 33% | 47% | 88% | 98% |
| Ki (nM) (NDP-α-MSH) | | | |
| 580 | 535 | 255 | 38 |

EXAMPLE 7

1-((2R,5S)-4-[(R)-2-Dimethylamino-3-(2,4-dimethyl-phenyl)-propyl]-2-methyl-5-{3-[methyl-(1-methyl-pyrrolidin-3-yl)-amino]-propyl}-piperazin-1-yl)-2-aphthalen-2-yl-ethanone The following compound was synthesized by the method of Scheme 1. The product of Example 5 was subjected to the method of 1-12 to produce the product. Following purification, the compound was tested as described above with the results shown. The mass was analyzed as 612.9 (M+H).

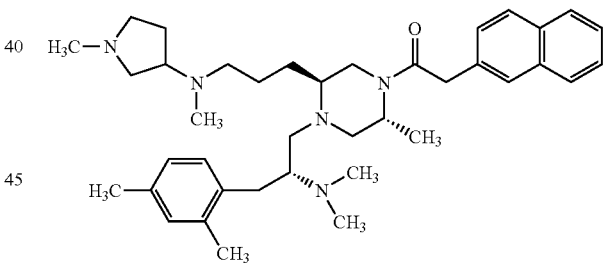

| | Inhibition at 1 μM (NDP-α-MSH) | | |
|---|---|---|---|
| MC1-R | MC3-R | MC4-R | MC5-R |
| 4% | 0% | 56% | 44% |

EXAMPLE 8

1-{(2R,5S)-5-{(3-[(2-Dimethylamino-cyclohexyl)-methyl-amino]-propyl}-4-[(R)-2-dimethylamino-3-(2,4-dimethyl-phenyl)-propyl]-2-methyl-piperazin-1-yl}-2-naphthalen-2-yl-ethanone The following compound was synthesized by method of Scheme 1. The product of Example 6 was subject to the method of 1-12 to produce the product. Following purification, the compound was tested as described above with the results shown. The mass was analyzed as 645.9 (M+H).

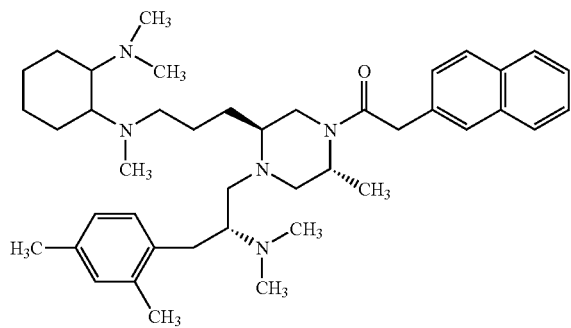

| Inhibition at 1 μM (NDP-α-MSH) | | | |
|---|---|---|---|
| MC1-R | MC3-R | MC4-R | MC5-R |
| 26% | 28% | 52% | 48% |

EXAMPLE 9

1-((2R,5S)-4-[(R)-2-Dimethylamino-3-(2,4-dimethyl-phenyl)-propyl]-5-{3-[(2-dimethylamino-ethyl)-methyl-amino]-propyl}-2-methyl-piperazin-1-yl)-2-naphthalen-2-yl-ethaone The following compound was synthesized by the method of Scheme 1. Following purification, the compound was tested as described above with the results shown. The mass was analyzed as 599.7 (M+H).

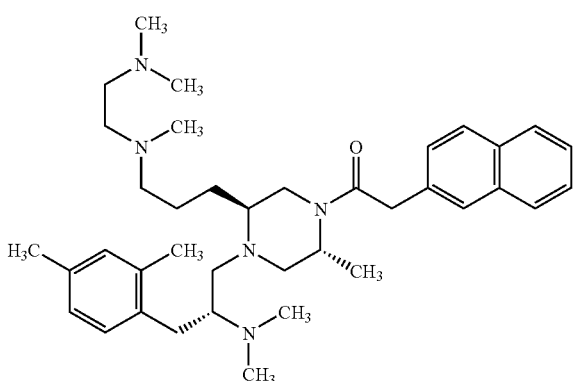

| Inhibition at 1 μM (NDP-α-MSH) | | | |
|---|---|---|---|
| MC1-R | MC3-R | MC4-R | MC5-R |
| 0% | 9% | 49% | 51% |

EXAMPLE 10

1-{(2R,5S)-4-[(R)-2-Dimethylamino-3-(2,4-dimethyl-phenyl)-propyl]-2-methyl-5-[3-(4-methyl-piperazin-1-yl)-propyl]-piperazin-1-yl}-2-naphthalen-2-1-ethanone The following compound was synthesized by the method of Scheme 1. The product of Example 4 was subject to the method of 1-12 to produce the product. Following purification, the compound was tested as described above with the results shown. The mass was analyzed as 597.7 (M+H).

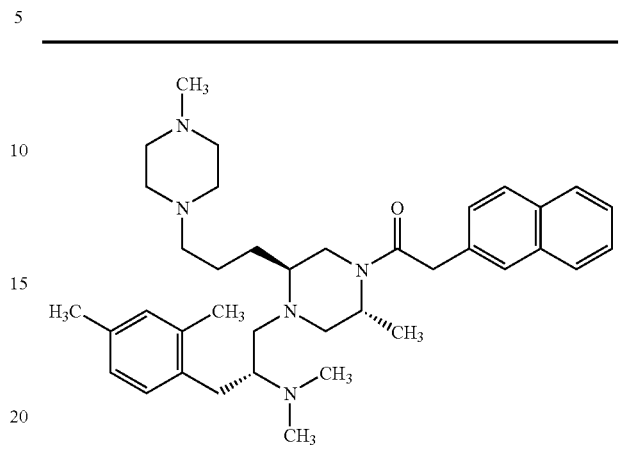

| Inhibition at 1 μM (NDP-α-MSH) | | | |
|---|---|---|---|
| MC1-R | MC3-R | MC4-R | MC5-R |
| 28% | 15% | 47% | 54% |

EXAMPLE 11

1-{(2R,5S)-4-[(R)-2-Amino-3-(2,4-dimethyl-phenyl)-propyl]-5-[4-(2-amino-ethylamino)-benzyl]-2-methyl-piperazin-1-yl}-2-naphthalen-2-yl-ethanone The following compound was synthesized by the method of Scheme 1. L-4'-(Cb₂-amino)-phenylalanine methyl ester was used for the synthesis of intermediate 1-4 instead of L-Orn(Boc)-OMe. The analog of 1-11 was treated by TFA/DCM to give product. Following purification, the compound was tested as described above with the results shown. The mass was analyzed as 578 (M+H).

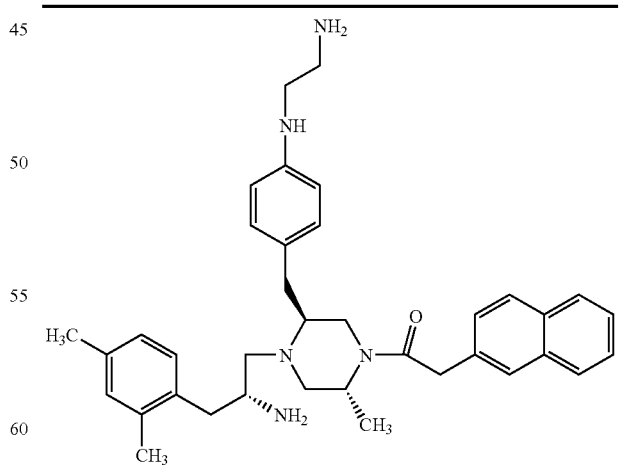

| Inhibition at 1 μM (NDP-α-MSH) | | | |
|---|---|---|---|
| hMC1-R | MC3-R | MC4-R | MC5-R |
| 3% | 29% | 39% | 36% |

EXAMPLE 12

(R)-2-Amino-1-{(2R,5S)-4-[(R)-2-amino-3-(2,4-dichloro-phenyl)-propionyl]-5-[3-(2-amino-ethylamino)-propyl]-2-isobutyl-piperazin-1-yl}-3-(2,4-dichloro-phenyl)-propan-1-one The following compound was synthesized by the method of Scheme 5 using Boc-D-2,4 dichloro-phenylalanine as Q-COOH, and D-Leu-OMe as $NH_2$—$CH(R_2)$—COOMe. Following purification, the compound was tested as described above with the results shown. The mass was analyzed as 672.3 (M+H).

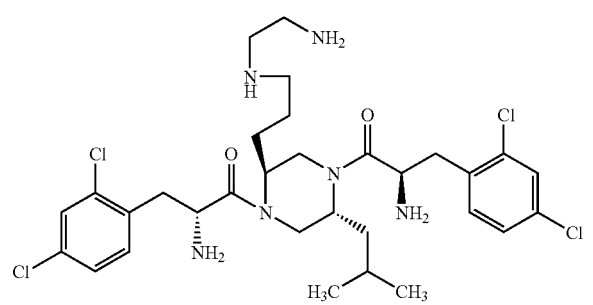

| hMC1-R | MC3-R | MC4-R | MC5-R |
|---|---|---|---|
| Inhibition at 1 μM (NDP-α-MSH) | | | |
| 23% | 41% | 89% | 55% |
| Ki (nM) (NDP-α-MSH) | | | |
| 309 | 574 | 44 | ND |

In mouse model IN feeding studies at a 0.1 and 0.3 mg/kg dose level, an average decrease in body weight of 0.7% and 3.1%, respectively, compared to control animals was observed at 20 hours.

EXAMPLE 13

(R)-2-Amino-1-[(2R,5S)-5-[3-(2-amino-ethylamino)-propyl]-4-((R)-2-amino-3-naphthalen-2-yl-propionyl)-2-isobutyl-piperazin-1-yl]-3-naphthalen-2-yl-propan-1-one The following compound was synthesized by the method of Scheme 5 using Boc-D-2'-naphthylalanine acid as Q-COOH and D-Leu-OMe as $NH_2$—$CH(R_2)$—COOMe. Following purification, the compound was tested as described above with the results shown. The mass was analyzed as 636.6 (M+H).

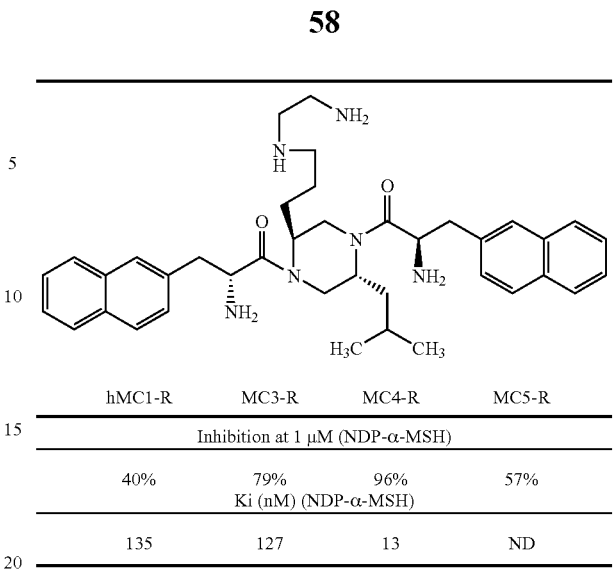

| hMC1-R | MC3-R | MC4-R | MC5-R |
|---|---|---|---|
| Inhibition at 1 μM (NDP-α-MSH) | | | |
| 40% | 79% | 96% | 57% |
| Ki (nM) (NDP-α-MSH) | | | |
| 135 | 127 | 13 | ND |

In mouse model IN feeding studies at a 0.1, 0.3 and 1 mg/kg dose level, an average decrease in body weight of 1%, 3% and 3.2%, respectively, compared to control animals was observed at 20 hours.

EXAMPLE 14

(R)-2-Amino-1-{(2R,5S)-4-[(R)-2-amino-3-(2,4-dimethyl-phenyl)-propionyl]-5-[3-(2-amino-ethylamino)-propyl]-2-cyclohexylmethyl-piperazin-1-yl}-3-(2,4-dimethyl-phenyl)-propan-1-one The following compound was synthesized by the method of Scheme 5 using Boc-2,4-dimethyl-phenylalanine as Q-COOH and D-cyclohexylalamine as $NH_2$—$CH(R_2)$—COOMe. Following purification, the compound was tested as described above with the results shown. The mass was analyzed as 632.8 (M+H).

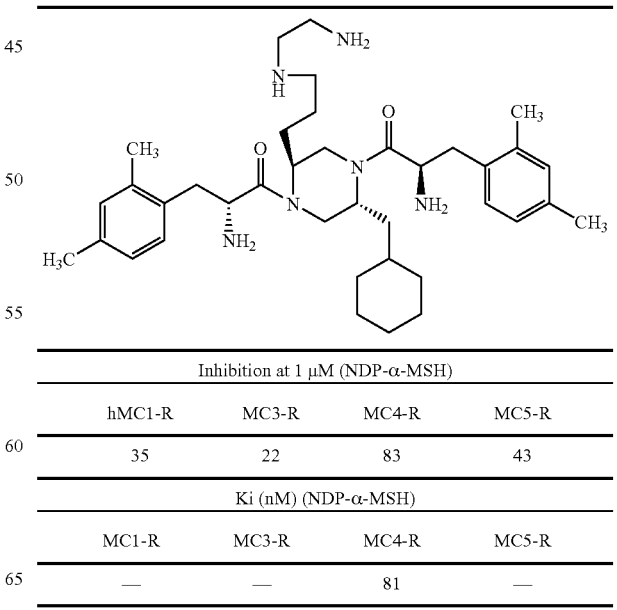

| Inhibition at 1 μM (NDP-α-MSH) | | | |
|---|---|---|---|
| hMC1-R | MC3-R | MC4-R | MC5-R |
| 35 | 22 | 83 | 43 |
| Ki (nM) (NDP-α-MSH) | | | |
| MC1-R | MC3-R | MC4-R | MC5-R |
| — | — | 81 | — |

EXAMPLE 15

(R)-2-Amino-1-{(2R,5S)-4-[(R)-2-amino-3-(2,4-dichloro-phenyl)-propionyl]-5-[3-(2-amino-ethylamino)-propyl]-2-cyclohexylmethyl-piperazin-1-yl}-3-(2,4-dichloro-phenyl)-propan-1-one The following compound was synthesized by the method of Scheme 5 using Boc-2,4-dichloro-phenylalanine as Q-COOH and D-cyclohexylalamine as $NH_2$—$CH(R_2)$—COOMe. Following purification, the compound was tested as described above with the results shown. The mass was analyzed as 712.6 (M+H).

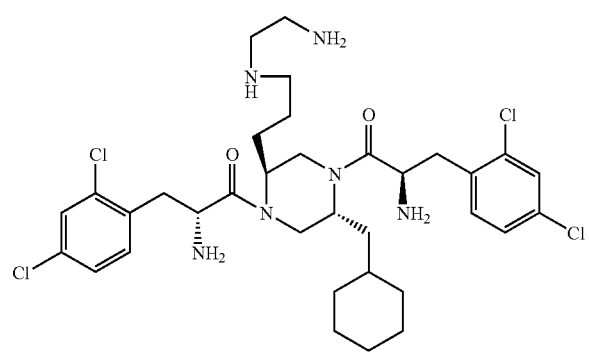

| Inhibition at 1 μM (NDP-α-MSH) | | | |
|---|---|---|---|
| hMC1-R | MC3-R | MC4-R | MC5-R |
| 27% | 36% | 83% | 31% |

| Ki (nM) (NDP-α-MSH) | | | |
|---|---|---|---|
| MC1-R | MC3-R | MC4-R | MC5-R |
| ND | ND | 74 | ND |

EXAMPLE 16

(R)-2-Amino-1-[(2R,5S)-5-[3-(2-amino-ethylamino)-propyl]-4-((R)-2-amino-3-naphthalen-2-yl-propionyl)-2-cyclohexylmethyl-piperazin-1-yl]-3-naphthalen-2-yl-propan-1-one The following compound was synthesized by the method of Scheme 5 using Boc-D-2'-naphthylalanine acid as Q-COOH and D-cyclohexylalamine as $NH_2$—$CH(R_2)$—COOMe. Following purification, the compound was tested as described above with the results shown. The mass was analyzed as 676.6 (M+H).

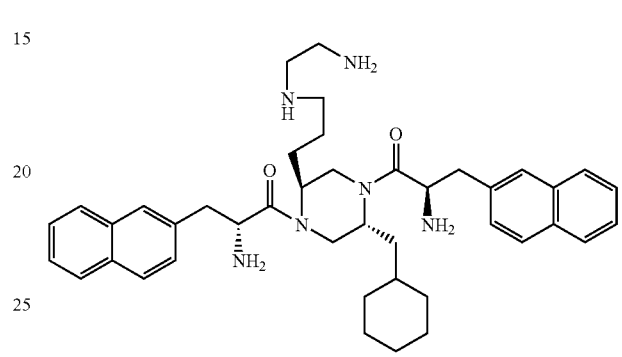

| Ki (nM) (NDP-α-MSH) | | | |
|---|---|---|---|
| hMC1-R | MC3-R | MC4-R | MC5-R |
| 22 | 36 | 81 | 30 |

| Ki (nM) (NDP-α-MSH) | | | |
|---|---|---|---|
| MC1-R | MC3-R | MC4-R | MC5-R |
| — | — | 99 | — |

EXAMPLE 17

(R)-2-Amino-1-{(2S,5R)-4-[(R)-2-amino-3-(2,4-dimethyl-phenyl)-propionyl]-2-[3-(2-amino-ethylamino)-propyl]-5-isobutyl-piperazin-1-yl}-3-(2,4-dimethyl-phenyl)-propan-1-one The following compound was synthesized by the method of Scheme 5 using Boc-2,4-dimethyl-phenylalanine as Q-COOH and D-Leu-OMe as $NH_2$—$CH(R_2)$—COOMe. Following purification, the compound was tested as described above with the results shown. The mass was analyzed as 592.9 (M+H).

| hMC1-R | MC3-R | MC4-R | MC5-R |
|---|---|---|---|
| Inhibition at 1 μM (NDP-α-MSH) | | | |
| 22% | 14% | 83% | 38% |
| Ki (nM) (NDP-α-MSH) | | | |
| ND | ND | 60 | ND |

EXAMPLE 18

1-{(2R,5S)-4-[(R)-2-Amino-3-(2,4-dichloro-phenyl)-propyl]-5-[3-(2-amino-ethylamino)-propyl]-2-isobutyl-piperazin-1-yl}-2-naphthalen-2-yl-ethanone The following compound was synthesized by the method of Scheme 3. Following purification, the compound was tested as described above with the results shown. The mass was analyzed as 612 (M+H).

| Ki (nM) (NDP-α-MSH) | | | |
|---|---|---|---|
| hMC1-R | MC3-R | MC4-R | MC5-R |
| 359 | 297 | 106 | 188 |

In mouse model IP feeding studies in fasted animals at a 3 mg/kg dose level, an average decrease in food intake of 30% compared to control animals was observed at 20 hours.

In mouse model IN feeding studies at a 0.1, 0.3 and 1 mg/kg dose level, an average decrease in body weight of 3%, 3.5% and 6.2%, respectively, compared to control animals was observed at 20 hours.

Example 19

(R)-2-Amino-1-{(2R,5S)-4-[(R)-2-amino-3-(2,4-dichloro-phenyl)-propionyl]-5-[4-(2-amino-ethylamino)-butyl]-2-isobutyl-piperazin-1-yl}-3-(2,4-dichloro-phenyl)-propan-1-one The following compound was synthesized by the method of Scheme 4 using Boc-2,4-dichloro-phenylalanine as Q-COOH and D-Leu-OMe as NH$_2$—CH(R$_2$)—COOMe. Following purification, the compound was tested as described above with the results shown. The mass was analyzed as 687 (M+H).

| hMC1-R | MC3-R | MC4-R | MC5-R |
|---|---|---|---|
| Inhibition at 1 μM (NDP-α-MSH) | | | |
| 36% | 59% | 97% | 47% |
| Ki (nM) (NDP-α-MSH) | | | |
| 754 | 327 | 36 | 296 |

Example 20

(R)-2-Amino-1-[(2R,5S)-5[4-(2-amino-ethylamino)-butyl]-4-((R)-2-amino-3-naphthalen-2-yl-propionyl)-2-isobutyl-piperazin-1-yl]-3-naphthalen-2-yl-propan-1-one The following compound was synthesized by the method of Scheme 4 using Boc-D-2'-naphthylalanine acid as Q-COOH and D-Leu-OMe as $NH_2$—$CH(R_2)$—COOMe. Following purification, the compound was tested as described above with the results shown. The mass was analyzed as 651.3 (M+H).

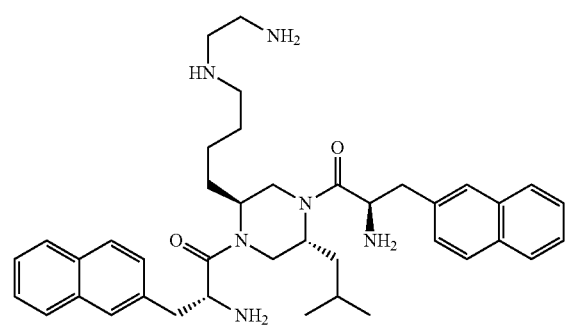

| hMC1-R | MC3-R | MC4-R | MC5-R |
|---|---|---|---|
| Inhibition at 1 µM (NDP-α-MSH) | | | |
| 68% | 62% | 99% | 49% |
| Ki (nM) (NDP-α-MSH) | | | |
| 215 | 321 | 9 | 253 |

In mouse model IN feeding studies in fed animals at a 0.1 and 0.3 mg/kg dose level, an average decrease in body weight of 1.2%, and 3%, respectively, compared to control animals was observed at 20 hours.

Example 21

(R)-2-Amino-1-{(2R,5S)-4-[(R)-2-amino-3-(2,4-dimethyl-phenyl)-propionyl]-5[4-(2-amino-ethylamino)-butyl]-2-isobutyl-piperazin-1-yl}-3-(2,4-dimethyl-phenyl)-propan-1-one The following compound was synthesized by the method of Scheme 4 using Boc-2,4-dimethyl-phenylalanine as Q-COOH and D-Leu-OMe as $NH_2$—$CH(R_2)$—COOMe. Following purification, the compound was tested as described above with the results shown. The mass was analyzed as 607.4 (M+H).

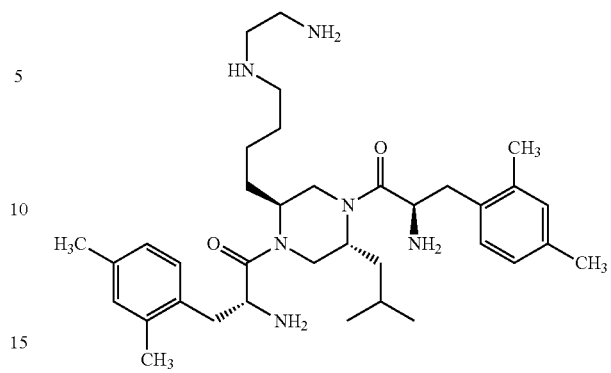

| hMC1-R | MC3-R | MC4-R | MC5-R |
|---|---|---|---|
| Inhibition at 1 µM (NDP-α-MSH) | | | |
| 39% | 55% | 95% | 51% |
| Ki (nM) (NDP-α-MSH) | | | |
| 567 | 1047 | 83 | 450 |

Example 22

(R)-2-Amino-1-{(2R,5S)-4-[(R)-2-amino-3-(3,4-dichloro-phenyl)-propionyl]-5-[4-(2-amino-ethylamino)-butyl]-2-isobutyl-piperazin-1-yl}-3-(3,4-dichloro-phenyl)-propan-1-one The following compound was synthesized by the method of Scheme 4 using Boc-3,4-dichloro-phenylalanine as Q-COOH and D-Leu-OMe as $NH_2$—$CH(R_2)$—COOMe. Following purification, the compound was tested as described above with the results shown. The mass was analyzed as 687.2 (M+H).

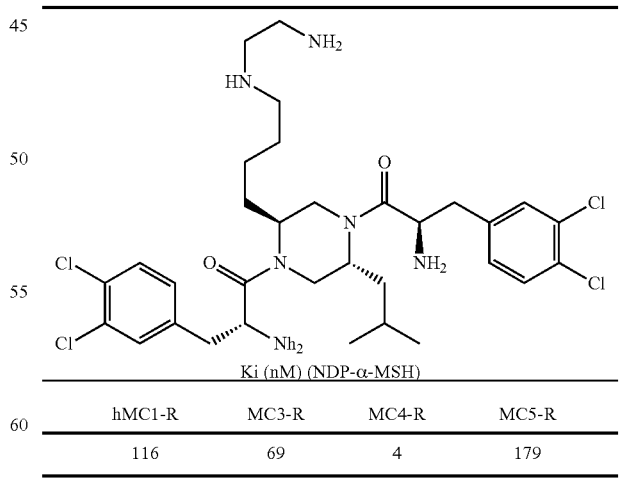

| hMC1-R | MC3-R | MC4-R | MC5-R |
|---|---|---|---|
| Ki (nM) (NDP-α-MSH) | | | |
| 116 | 69 | 4 | 179 |

In mouse model IN feed studies at a 0.1 and 0.3 mg/kg dose level, an average decrease in body weight of 0.6% and 4.9%, respectively, compared to control animals was observed at 20 hours.

Example 23

(R)-2-Amino-1-[(2R,5S)-5-[4-(2-amino-ethylamino)-butyl]-4-((R)-2-amino-3-naphthalen-2-yl-propionyl)-2-cyclohexylmethyl-piperazin-1-yl]-3-naphthalen-2-yl-propan-1-one The following compound was synthesized by the method of Scheme 4 using Boc-D-2'-naphthylalanine as Q-COOH and D-Cyclohexylalanine as $NH_2$—$CH(R_2)$—COOMe. Following purification, the compound was tested as described above with the results shown. The mass was analyzed as 691.3 (M+H).

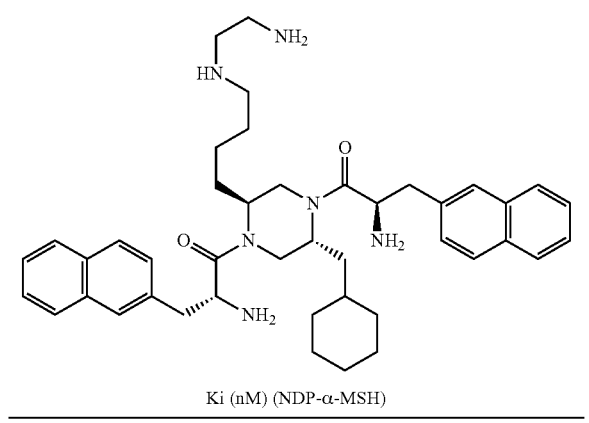

Ki (nM) (NDP-α-MSH)

| hMC1-R | MC3-R | MC4-R | MC5-R |
|---|---|---|---|
| 153 | 435 | 20 | 103 |

In mouse model IN feed studies at a 0.1 and 0.3 mg/kg dose level, an average decrease in body weight of 1.6% and 2.6%, respectively, compared to control animals was observed at 20 hours.

Example 24

(R)-2-Amino-1-{(2R,5S)-4-[(R)-2-amino-3-(2,4-dichloro-phenyl)-propionyl]-5-[4-(2-amino-ethylamino)-butyl]-2-cyclohexylmethyl-piperazin-1-yl}-3-(2,4-dichloro-phenyl)-propan-1-one The following compound was synthesized by the method of Scheme 4 using Boc-2,4-dichloro-phenylalanine as Q-COOH and D-Cyclohexylalanine as $NH_2$—$CH(R_2)$—COOMe. Following purification, the compound was tested as described above with the results shown. The mass was analyzed as 727 (M+H).

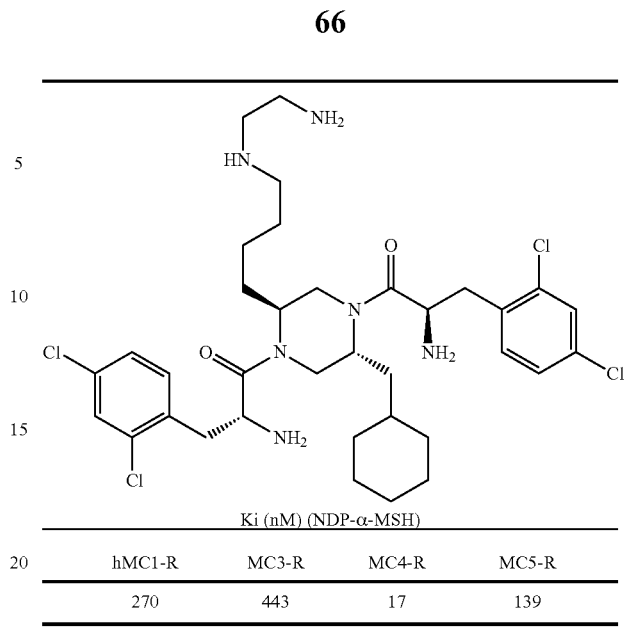

Ki (nM) (NDP-α-MSH)

| hMC1-R | MC3-R | MC4-R | MC5-R |
|---|---|---|---|
| 270 | 443 | 17 | 139 |

EXAMPLE 25

(R)-2-Amino-1-{(2R,5S)-4-[(R)-2-amino-3-(2,4-dichloro-phenyl)-propionyl]-5-[3-(2-amino-ethylamino)-propyl]-2-methyl-piperazin-1-yl}-3-(2,4-dichloro-phenyl)-propan-1-one The following compound was synthesized by the method of Scheme 5 using Boc-2,4-dichloro-phenylalanine as Q-COOH and D-Ala-OMe as $NH_2$—$CH(R_2)$—COOMe. Following purification, the compound was tested as described above with the results shown. The mass was analyzed as 631 (M+H).

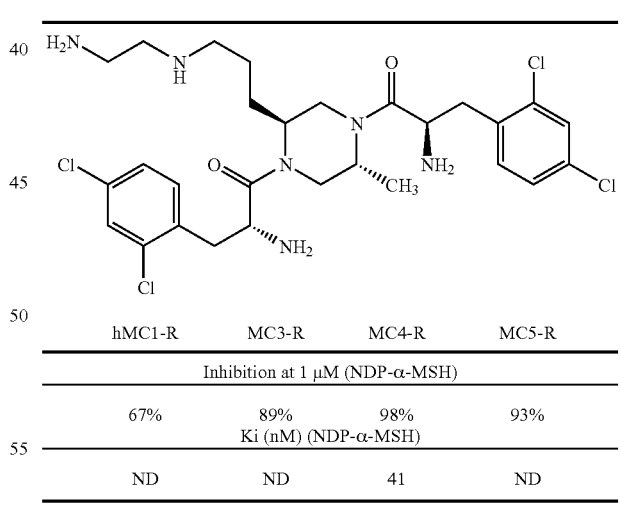

| hMC1-R | MC3-R | MC4-R | MC5-R |
|---|---|---|---|
| Inhibition at 1 μM (NDP-α-MSH) | | | |
| 67% | 89% | 98% | 93% |
| Ki (nM) (NDP-α-MSH) | | | |
| ND | ND | 41 | ND |

EXAMPLE 26

(R)-2-Amino-1-{(2R,5S)-4-[(R)-2-amino-3-(2,4-dimethyl-phenyl)-propionyl]-5-[3-(2-amino-ethylamino)-propyl]-2-methyl-piperazin-1-yl}-3-(2,4-dimethyl-phenyl)-propan-1-one The following compound was synthesized by the method of Scheme 5 using Boc-2,4-dimethyl-phenylalanine as Q-COOH and D-Ala-OMe as NH$_2$—CH(R$_2$)—COOMe. Following purification, the compound was tested as described above with the results shown. The mass was analyzed as 551.3 (M+H).

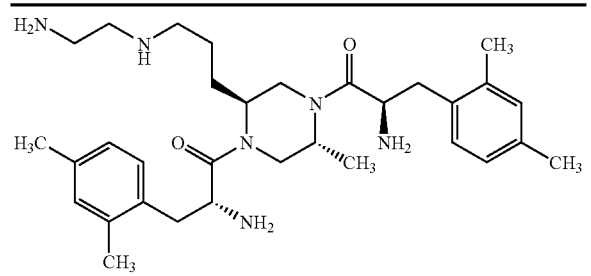

| hMC1-R | MC3-R | MC4-R | MC5-R |
|---|---|---|---|
| Inhibition at 1 μM (NDP-α-MSH) | | | |
| 53% | 57% | 96% | 76% |
| Ki (nM) (NDP-α-MSH) | | | |
| ND | ND | 64 | ND |

EXAMPLE 27

(R)-2-Amino-1-[(2R,5S)-5-[3-(2-amino-ethylamino)-propyl]-4-((R)-2-amino-3-naphthalen-2-yl-propionyl)-2-methyl-piperazin-1-yl]-3-naphthalen-2-yl-propan-1-one The following compound was synthesized by the method of Scheme 5 using Boc-D-2'-naphthylalanine acid as Q-COOH and D-Ala-OMe as NH$_2$—CH(R$_2$)—COOMe. Following purification, the compound was tested as described above with the results shown. The mass was analyzed as 595.2 (M+H).

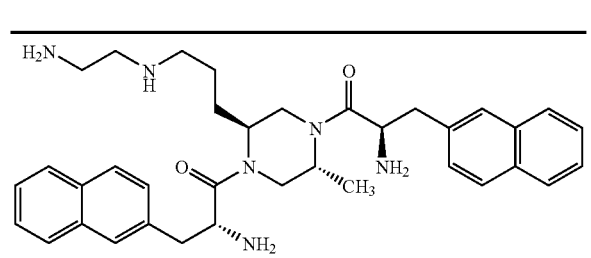

| hMC1-R | MC3-R | MC4-R | MC5-R |
|---|---|---|---|
| Inhibition at 1 μM (NDP-α-MSH) | | | |
| 62% | 79% | 93% | 73% |
| Ki (nM) (NDP-α-MSH) | | | |
| ND | ND | 42 | ND |

EXAMPLE 28

(R)-2-Amino-1-{(2R,5S)-4-[(R)-2-amino-3-(3,4-dichloro-phenyl)-propionyl]-5-[3-(2-amino-ethylamino)-propyl]-2-methyl-piperazin-1-yl}-3-(3,4-dichloro-phenyl)-propan-1-one The following compound was synthesized by the method of Scheme 5 using Boc-3,4-dichloro-phenylalanine as Q-COOH and D-Ala-OMe as NH$_2$—CH(R$_2$)—COOMe. Following purification, the compound was tested as described above with the results shown. The mass was analyzed as 631 (M+H).

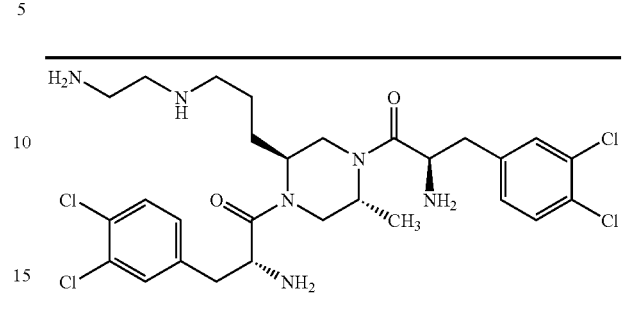

| hMC1-R | MC3-R | MC4-R | MC5-R |
|---|---|---|---|
| Inhibition at 1 μM (NDP-α-MSH) | | | |
| 77% | 94% | 96% | 84% |
| Ki (nM) (NDP-α-MSH) | | | |
| ND | ND | 19 | ND |

EXAMPLE 29

1-{(2R,5S)-4-[(R)-2-Amino-3-(2,4-dichloro-phenyl)-propyl]-5-[3-(3-amino-propylamino)-propyl]-2-isobutyl-piperazin-1-yl}-2-naphthalen-2-yl-ethanone The following compound was synthesized by the method of Scheme 3. N—Boc-1,3-propanediamine was used for the synthesis of intermediate 3-7. Following purification, the compound was tested as described above with the results shown. The mass was analyzed as 625.8 (M+H).

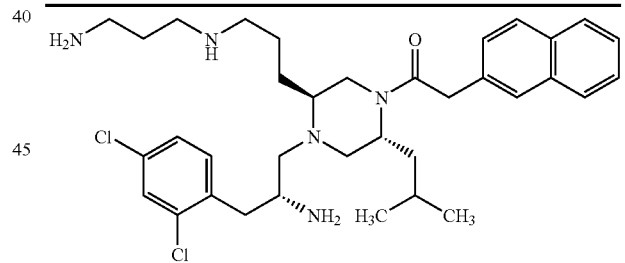

| | Inhibition at 1 μM (NDP-α-MSH) | | |
|---|---|---|---|
| hMC1-R | MC3-R | MC4-R | MC5-R |
| 33% | 65% | 91% | 84% |

EXAMPLE 30

1-{(2R,5S)-5-[3-(4-Amino-butylamino)-propyl]-4-[(R)-2-amino-3-(2,4-dichloro-phenyl)-propyl]-2-isobutyl-piperazin-1-yl}-2-naphthalen-2-yl-ethanone The following compound was synthesized by the method of Scheme 3. N—Boc-1,4-butanediamine was used for the synthesis of intermediate 3-7. Following purification, the compound was tested as described above with the results shown. The mass was analyzed as 639.7 (M+H).

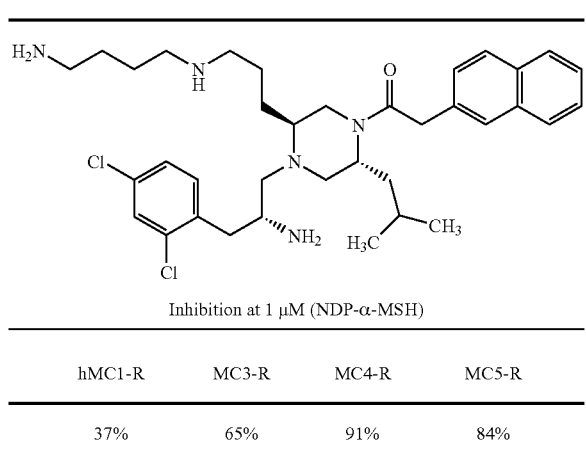

Inhibition at 1 µM (NDP-α-MSH)

| hMC1-R | MC3-R | MC4-R | MC5-R |
|---|---|---|---|
| 37% | 65% | 91% | 84% |

EXAMPLE 31

1-{(2R,5S)-4-[(R)-2-Amino-3-(2,4-dichloro-phenyl)-propyl]-5-[3-(5-amino-pentylamino)-propyl]-2-isobutyl-piperazin-1-yl}-2-naphthalen-2-yl-ethanone The following compound was synthesized by the method of Scheme 3. N—Boc-1,5-heptanediamine was used for the synthesis of intermediate 3-7. Following purification, the compound was tested as described above with the results shown. The mass was analyzed as 653.8 (M+H).

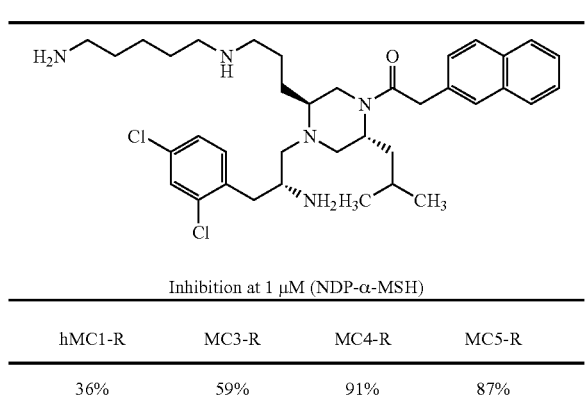

Inhibition at 1 µM (NDP-α-MSH)

| hMC1-R | MC3-R | MC4-R | MC5-R |
|---|---|---|---|
| 36% | 59% | 91% | 87% |

EXAMPLE 32

1-{(2R,5S)-5-{3-[(2-Amino-ethyl)-methyl-amino]-propyl}-4-[(R)-3-(2,4-dichloro-phenyl)-2-dimethylamino-propyl]-2-isobutyl-piperazin-1-yl}-2-naphthalen-2-yl-ethanone The following compound was synthesized by the method of Scheme 3. Methylation of amines was carried out by the method described in the synthesis of 2-12. Following purification, the compound was tested as described above with the results shown. The mass was analyzed as 653.6 (M+H).

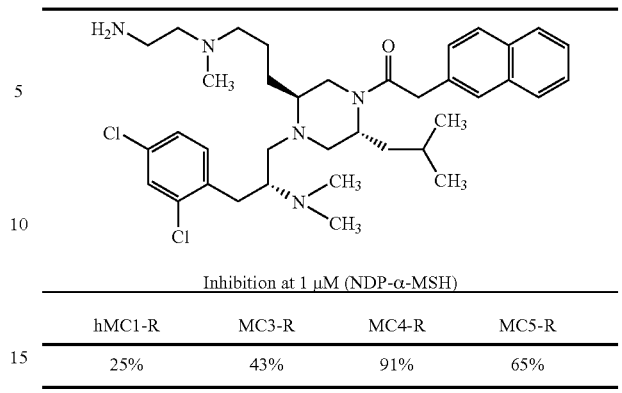

Inhibition at 1 µM (NDP-α-MSH)

| hMC1-R | MC3-R | MC4-R | MC5-R |
|---|---|---|---|
| 25% | 43% | 91% | 65% |

The preceding examples can be repeated with similar success by substituting the generically or specifically described reactants and/or synthetic conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:
1. A compound having the formula of structure I:

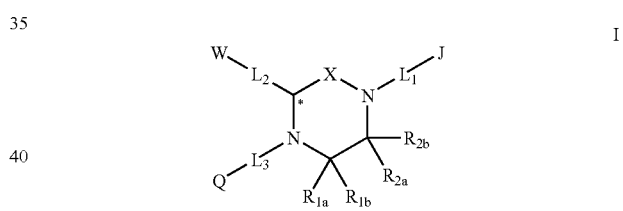

or an enantiomer, stereoisomer or diastereoisomer thereof, or a pharmaceutically acceptable salt thereof,
wherein
J is a ring structure selected from the group consisting of substituted or unsubstituted aromatic carbocyclic rings, substituted or unsubstituted aromatic fused carbobicyclic ring groups, or two substituted or unsubstituted aromatic carbocyclic rings wherein the rings are joined by a bond, —CH$_2$—, or —O—, wherein in each instance the ring attached to L$_1$ has 6 ring atoms;
W is a diamine heteroatom unit with at least one cationic center, hydrogen bond donor or hydrogen bond acceptor;
Q is an aromatic carbocyclic ring selected from the group consisting of phenyl, substituted phenyl, naphthyl and substituted naphthyl;
L$_1$ is —C(=O)—CH(N(R$_{10a}$R$_{10b}$))—CH$_2$—;
L$_2$ is a bond or —(CH$_2$)$_z$—;
L$_3$ is —C(=O)—CH(N(R$_{10a}$R$_{10b}$))—CH$_2$—;
one or two of R$_{1a}$, R$_{1b}$, R$_{2a}$, and R$_{2b}$ are independently a C$_1$ to C$_6$ aliphatic linear or branched chain and the remaining of R$_{1a}$, R$_{1b}$, R$_{2a}$, and R$_{2b}$ are hydrogen, provided that at least one of R$_{1a}$ and R$_{1b}$ and at least one of R$_{2a}$ and R$_{2b}$ are hydrogen;

or one of $R_{1a}$, $R_{1b}$, $R_{2a}$, and $R_{2b}$ are

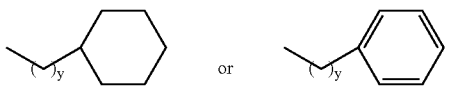

and the remaining of $R_{1a}$, $R_{1b}$, $R_{2a}$, and $R_{2b}$ are hydrogen;

or $R_{1a}$ and $R_{1b}$ together form =O and one of $R_{2a}$ and $R_{2b}$ is a $C_1$ to $C_6$ aliphatic linear or branched chain,

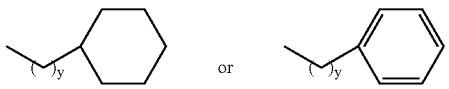

and the remaining of $R_{2a}$ and $R_{2b}$ is hydrogen;

each occurrence of $R_{10a}$ and $R_{10b}$ is independently hydrogen, acetyl, methyl, ethyl, propyl, isopropyl, butyl, pentyl, hexyl, isobutyl, benzyl, benzoyl, hexanoyl, propionyl, butanoyl, pentanoyl, heptanoyl, cyclopropyl, cyclopropylmethyl, cyclobutyl, cyclobutylmethyl, cyclohexyl, cyclohexylmethyl, or polyethylene glycol;

X is $CH_2$, C=O or C=S;

z is an index value from 1 to 6; and y is an index value from 0 to 5;

wherein the carbon atom marked with an asterisk can have any stereochemical configuration.

2. The compound of claim 1 wherein J is linked to $L_1$ through an aromatic carbocyclic ring forming a part thereof and is:

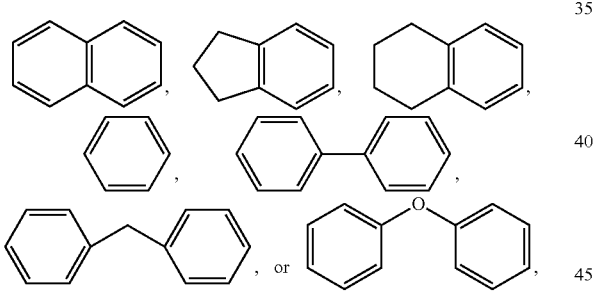

unsubstituted or substituted with one or more ring substituents.

3. The compound of claim 2 wherein J is substituted with one or more ring substituents independently selected from the group consisting of hydroxyl, halogen, sulfonamide, alkyl, —O-alkyl, aryl, and —O-aryl.

4. The compound of claim 1 wherein Q is:

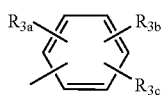

wherein $R_{3a}$, $R_{3b}$ and $R_{3c}$ are optional ring substituents, and when one or more are present, are the same or different and independently hydroxyl, halogen, alkyl, —O-alkyl, aryl, or —O-aryl.

5. The compound of claim 4 wherein at least one of $R_{3a}$, $R_{3b}$ or $R_{3c}$ is —$CH_3$ or —O—$CH_3$.

6. The compound of claim 4 wherein at least one of $R_{3a}$, $R_{3b}$ or $R_{3c}$ is —Cl or —$CF_3$.

7. The compound of claim 1 wherein Q and J are the same.

8. The compound of claim 1 wherein W is:

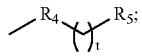

$R_4$ is

NH,

O, provided that $R_5$ comprises a diamine, $CH_2$, provided that $R_5$ comprises a diamine, $C_6H_5$, provided that $R_5$ comprises a diamine, N(—$CH_2$)$_z$ where N($CH_2$)$_z$ together with $R_5$ forms a ring, or N($CH_2$)$_y$—$CH_3$);

$R_5$ is $NH_2$, provided that $R_4$ comprises an amine,

NH—($CH_2$)$_z$ where NH—($CH_2$)$_z$ together with $R_4$ forms a ring,

NH—($CH_2$)$_y$—$CH_3$,

N(—($CH_2$)$_y$—$CH_3$)$_2$,

NH—($CH_2$)$_z$—$NH_2$,

NH—($CH_2$)$_z$—NH—($CH_2$)$_y$—$CH_3$,

NH—($CH_2$)$_z$—N—(($CH_2$)$_y$—$CH_3$)$_2$,

N(—($CH_2$)$_y$—$CH_3$)—($CH_2$)$_z$—NH($CH_2$)$_y$—$CH_3$,

N(—($CH_2$)$_y$—$CH_3$)—($CH_2$)$_z$—N(($CH_2$)$_y$—$CH_3$)$_2$,

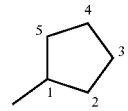

where one or more of positions 1 to 5 are a heteroatom selected from N for position 1 and S, O or NH for positions 2 to 5, provided that only one N is present if $R_4$ comprises an amine, and otherwise $R_5$ comprises a diamine,

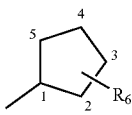

where none, one or two of positions 1 to 5 are a heteroatom selected from N for position 1 and for the position to which $R_6$ is bound if such position does not comprise C, and otherwise S, O or NH, provided that $R_5$ including $R_6$ comprises only one N if $R_4$ comprises an amine, and otherwise $R_5$ including $R_6$ comprises a diamine,

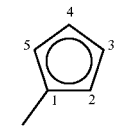

where at least one bond between adjacent ring atoms is a double bond, and one or more of positions 1 to 5 are a heteroatom selected from N for position 1 and any double bond position and otherwise S, O or NH for positions 2 to 5, provided that not more than one position is S or O, and further provided that only one N is present if $R_4$ comprises an amine, and otherwise $R_5$ comprises a diamine,

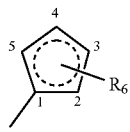

where at least one bond between adjacent ring atoms is a double bond, and one or more of positions 1 to 5 are optionally a heteroatom selected from N for position 1, the position to which $R_6$ is bound if such position does not comprise C, and any double bond position and otherwise S, O or NH for positions 2 to 5, provided that not more than one position is S or O, and further provided that $R_5$ including $R_6$ comprises only one N if $R_4$ comprises an amine, and otherwise $R_5$ including $R_6$ comprises a diamine,

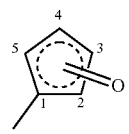

where at least one bond between adjacent ring atoms is a double bond, the oxo is bound to a ring carbon, and one or more of the remaining of positions 1 to 5 are optionally a heteroatom selected from N for position 1 and any double bond position and otherwise S, O or NH for positions 2 to 5, provided that not more than one ring position is S or O, and further provided that only one N is present if $R_4$ comprises an amine, and otherwise $R_5$ comprises a diamine,

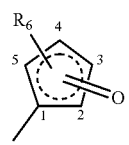

where at least one bond between adjacent ring atoms is a double bond, the oxo is bound to a ring carbon, and one or more of positions 1 to 5 are optionally a heteroatom selected from N for position 1, the position to which $R_6$ is bound if such position does not comprise C, and any double bond position and otherwise S, O or NH for positions 2 to 5, provided that not more than one position is S or O, and further provided that $R_5$ including $R_6$ comprises only one N if $R_4$ comprises an amine, and otherwise $R_5$ including $R_6$ comprises a diamine,

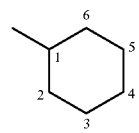

where one or more of positions 1 to 6 are a heteroatom selected from N for position 1 and S, O or NH for positions 2 to 6, provided that $R_5$ together with $R_6$ comprises only one N if $R_4$ comprises an amine, and otherwise $R_5$ including $R_6$ comprises a diamine,

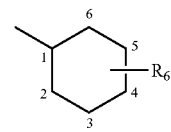

where one or two of positions 1 to 6 are a heteroatom selected from N for position 1 and the position to which $R_6$ is bound if such position does not comprise C, and otherwise S, O or NH, provided that $R_5$ including $R_6$ comprises only one N if $R_4$ comprises an amine, and otherwise $R_5$ including $R_6$ comprises a diamine,

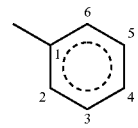

where at least one bond between adjacent ring atoms is a double bond, and one or more of positions 1 to 6 are a heteroatom selected from N for position 1 and any double bond position and otherwise S, O or NH or N—$(CH_2)_y$—$CH_3$ for positions 2 to 6, provided that not more than two positions are S or O, and further provided that $R_5$ together with $R_6$ comprises only one N if $R_4$ comprises an amine, and otherwise $R_5$ including $R_6$ comprises a diamine,

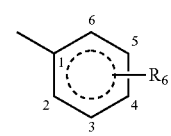

where at least one bond between adjacent ring atoms is a double bond, and one or more of positions 1 to 6 are optionally a heteroatom selected from N for position 1 and any double bond position and otherwise S, O or NH for positions 2 to 6, provided that not more than two positions are S or O, and further provided that $R_5$ including $R_6$ comprises only one N if $R_4$ comprises an amine, and otherwise $R_5$ including $R_6$ comprises a diamine,

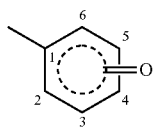

where at least one bond between adjacent ring atoms is a double bond, the oxo is bound to a ring carbon, and one or more of the remaining of positions 1 to 6 are optionally a heteroatom selected from N for position 1 and any double bond position and otherwise S, O or NH for positions 2 to 6, provided that not more than two positions are S or O, and further provided that only one N is present if $R_4$ comprises an amine, and otherwise $R_5$ comprises a diamine, or

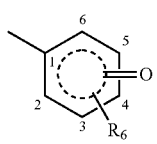

where at least one bond between adjacent ring atoms is a double bond, the oxo is bound to a ring carbon, and one or more of positions 1 to 6 are optionally a heteroatom selected from N for position 1, the position to which $R_6$ is bound if such position does not comprise C, and any double bond position and otherwise S, O or NH for positions 2 to 6, provided that not more than two positions are S or O, and further provided that $R_5$ including $R_6$ comprises only one N if $R_4$ comprises an amine, and otherwise $R_5$ including $R_6$ comprises a diamine;

$R_6$ is hydroxyl, $(CH_2)_y$—$CH_3$, $(CH_2)_y$—$NH_2$, $NH_2$, $NH$—$(CH_2)_y$—$CH_3$ or $N(-(CH_2)_y-CH_3)_2$;

t is an index value from 0 to 6;

z is an index value from 1 to 6; and y is in each instance independently an index value from 0 to 5;

provided that, any NH or $NH_2$ in the foregoing may be substituted by N-Prg or NH-Prg, respectively, where each Prg is independently an amine protecting group.

9. The compound of claim 8 wherein each Prg is independently acetyl, adamantyloxy, benzoyl, benzyl, benzyloxy, t-butoxycarbonyl, mesitylene-2-sulfonyl, 4-methoxy-2,3-6-trimethyl-benzenesulfonyl, 2,2,4,6,7-pentamethyldihydrobenzofurane-5-sulfonyl, 2,2,5,7,8-pentamethylchromane-6-sulfonyl, or tosyl.

10. The compound of claim 1 wherein W is:

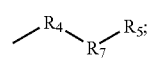

$R_4$ is

NH,

O, provided that $R_5$ comprises a diamine, $CH_2$, provided that $R_5$ comprises a diamine, $N(-CH_2)_z$ where $N(CH_2)_z$ together with $R_5$ forms a ring, $N(-(CH_2)_y-CH_3)$, $C(=O)$, provided that $R_5$ comprises a diamine, $C(=O)$—O, provided that $R_5$ comprises a diamine, or $O$—$C(=O)$, provided that $R_5$ comprises a diamine;

$R_5$ is $NH_2$, provided that $R_4$ comprises one N,

NH—$(CH_2)_z$ where NH—$(CH_2)_z$ together with $R_4$ forms a ring,

NH—$(CH_2)_y$—$CH_3$, $N((CH_2)_y$—$CH_3)_2$,

NH—$(CH_2)_z$—$NH_2$,

NH—$(CH_2)_z$—NH—$(CH_2)_y$—$CH_3$,

NH—$(CH_2)_z$—N—$((CH_2)_y$—$CH_3)_2$, $N(-(CH_2)_y-CH_3)-(CH_2)_z-NH(CH_2)_y-CH_3$, $N(-(CH_2)_y-CH_3)-(CH_2)_z-N((CH_2)_y-CH_3)_2$,

NH—$C(=O)$—$(CH_2)_y$—$NH_2$, $SO_2$—$(CH_2)_y$—$CH_3$, provided that $R_4$ comprises a diamine,

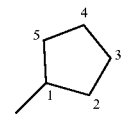

where one or more of positions 1 to 5 are a heteroatom selected from N for position 1 and S, O or NH for positions 2 to 5, provided that only one N is present if $R_4$ comprises an N, and otherwise $R_5$ comprises a diamine,

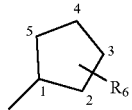

where one or two of positions 1 to 5 are a heteroatom selected from N for position 1 and for the position to which $R_6$ is bound if such position does not comprise C, and otherwise S, O or NH, provided that $R_5$ including $R_6$ comprises only one N if $R_4$ comprises an amine, and otherwise $R_5$ including $R_6$ comprises a diamine,

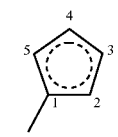

where at least one bond between adjacent ring atoms is a double bond, and none or one or more of positions 1 to 5 are a heteroatom selected from N for position 1 and any double bond position and otherwise S, O or NH for positions 2 to 5, provided that not more than one position is S or O, and further provided that only one N is present if $R_4$ comprises an amine, and otherwise $R_5$ comprises a diamine,

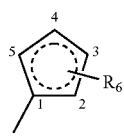

where at least one bond between adjacent ring atoms is a double bond, and one or more of positions 1 to 5 are optionally a heteroatom selected from N for position 1, the position to which $R_6$ is bound if such position does not comprise C, and any double bond position and otherwise S, O or NH for positions 2 to 5, provided that not more than one position is S or O, and further provided that $R_5$ including $R_6$ comprises only one N if $R_4$ comprises an amine, and otherwise $R_5$ including $R_6$ comprises a diamine,

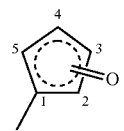

where at least one bond between adjacent ring atoms is a double bond, the oxo is bound to a ring carbon, and one or more of the remaining of positions 1 to 5 are optionally a heteroatom selected from N for position 1 and any double bond position and otherwise S, O or NH for positions 2 to 5, provided that not more than one ring position is S or O, and further provided that only one N is present if $R_4$ comprises an amine, and otherwise $R_5$ comprises a diamine,

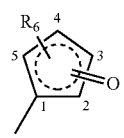

where at least one bond between adjacent ring atoms is a double bond, the hydroxyl is bound to a ring carbon, and one or more of positions 1 to 5 are optionally a heteroatom selected from N for position 1, the position to which $R_6$ is bound if such position does not comprise C, and any double bond position and otherwise S, O or NH for positions 2 to 5, provided that not more than one position is S or O, and further provided that $R_5$ including $R_6$ comprises only one N if $R_4$ comprises an amine, and otherwise $R_5$ including $R_6$ comprises a diamine,

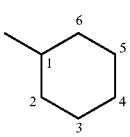

where one or more of positions 1 to 6 are a heteroatom selected from N for position 1 and S, O or NH for positions 2 to 6, provided that $R_5$ together with $R_6$ comprises only one N if $R_4$ comprises an amine, and otherwise $R_5$ including $R_6$ comprises a diamine,

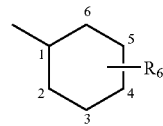

where none, one or two of positions 1 to 6 are a heteroatom selected from N for position 1 and the position to which $R_6$ is bound if such position does not comprise C, and otherwise S, O or NH, provided that $R_5$ including $R_6$ comprises only one N if $R_4$ comprises an amine, and otherwise $R_5$ including $R_6$ comprises a diamine,

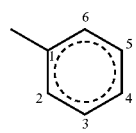

where at least one bond between adjacent ring atoms is a double bond, and one or more of positions 1 to 6 are a heteroatom selected from N for position 1 and any double bond position and otherwise S, O or NH or N—$(CH_2)_y$—$CH_3$ for positions 2 to 6, provided that not more than two positions are S or O, and further provided that $R_5$ together with $R_6$ comprises only one N if $R_4$ comprises an amine, and otherwise $R_5$ including $R_6$ comprises a diamine,

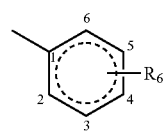

where at least one bond between adjacent ring atoms is a double bond, and one or more of positions 1 to 6 are optionally a heteroatom selected from N for position 1 and any double bond position and otherwise S, O or NH for positions 2 to 6, provided that not more than two positions are S or O, and further provided that $R_5$ including $R_6$ comprises only one N if $R_4$ comprises an amine, and otherwise $R_5$ including $R_6$ comprises a diamine,

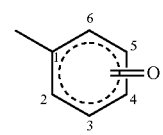

where at least one bond between adjacent ring atoms is a double bond, the oxo is bound to a ring carbon, and one or more of the remaining of positions 1 to 6 are optionally a heteroatom selected from N for position 1 and any double bond position and otherwise S, O or NH for positions 2 to 6, provided that not more than two positions are S or O, and further provided that only one N is present if $R_4$ comprises an amine, and otherwise $R_5$ comprises a diamine, or

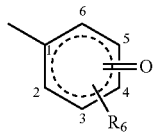

where at least one bond between adjacent ring atoms is a double bond, the oxo is bound to a ring carbon, and one or more of positions 1 to 6 are optionally a heteroatom selected from N for position 1, the position to which $R_6$ is bound if such position does not comprise C, and any double bond position and otherwise S, O or NH for positions 2 to 6, provided that not more than two positions are S or O, and further provided that $R_5$ including $R_6$ comprises only one N if $R_4$ comprises an amine, and otherwise $R_5$ including $R_6$ comprises a diamine;

$R_6$ is hydroxyl, $(CH_2)_y$—$CH_3$, $(CH_2)_y$—$NH_2$, $NH_2$, $NH$—$(CH_2)_y$—$CH_3$ or $N(—(CH_2)_y—CH_3)_2$;

$R_7$ is a $C_4$ to $C_{10}$ aliphatic comprising an optionally substituted cycloalkane or aryl ring;

z is an index value from 1 to 6; and y is in each instance independently an index value from 0 to 5;

wherein any NH or $NH_2$ in the foregoing may be substituted by N-Prg or NH-Prg, respectively, where each Prg is independently an amine protecting group.

11. The compound of claim 10 wherein each Prg is independently acetyl, adamantyloxy, benzoyl, benzyl, benzyloxycarbonyl, t-butoxycarbonyl, mesitylene-2-sulfonyl, 4-methoxy-2,3-6-trimethyl-benzenesulfonyl, 2,2,4,6,7-pentamethyldihydrobenzofurane-5-sulfonyl, 2,2,5,7,8-pentamethylchromane-6-sulfonyl, 9-fluorenylmethoxycarbonyl or tosyl.

12. The compound of claim 1 wherein the polyethylene glycol has a formula molecular weight of between 100 and 50,000.

13. The compound of claim 1 wherein one of $R_{2a}$ and $R_{2b}$ is

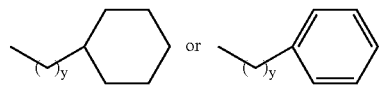

and the remaining of $R_{2a}$ and $R_{2b}$ and both $R_{1a}$ and $R_{1b}$ are hydrogen.

14. The compound of claim 1 of a formula:

1-{(2R,5S)-4-[(R)-2-amino-3-(2,4-dimethyl-phenyl)-propyl]-5-[4-(2-amino-ethylamino)-benzyl]-2-methyl-piperazin-1-yl}-2-naphthalen-2-yl-ethanone;

(R)-2-amino-1-{(2R,5S)-4-[(R)-2-amino-3-(2,4-dichloro-phenyl)-propionyl]-5-[3-(2-amino-ethylamino)-propyl]-2-isobutyl-piperazin-1-yl}-3-(2,4-dichloro-phenyl)-propan-1-one;

(R)-2-amino-1-[(2R,5S)-5-[3-(2-amino-ethylamino)-propyl]-4-((R)-2-amino-3-naphthalen-2-yl-propionyl)-2-isobutyl-piperazin-1-yl]-3-naphthalen-2-yl-propan-1-one;

(R)-2-amino-1-{(2R,5S)-4-[(R)-2-amino-3-(2,4-dimethyl-phenyl)-propionyl]-5-[3-(2-amino-ethylamino)-propyl]-2-cyclohexylmethyl-piperazin-1-yl}-3-(2,4-dimethyl-phenyl)-propan-1-one;

(R)-2-amino-1-{(2R,5S)-4-[(R)-2-amino-3-(2,4-dichloro-phenyl)-propionyl]-5-4-(2-amino-ethylamino)-propyl]-2-cyclohexylmethyl-piperazin-1-yl}-3-(2,4-dichloro-phenyl)-propan-1-one;

(R)-2-amino-1-[(2R,5S)-5-[3-(2-amino-ethylamino)-propyl]-4-((R)-2-amino-3-naphthalen-2-yl-propionyl)-2-cyclohexylmethyl-piperazin-1-yl]-3-naphthalen-2-yl-propan-1-one;

(R)-2-amino-1-{(2S,5R)-4-[(R)-2-amino-3-(2,4-dimethyl-phenyl)-propionyl]-2-[4-(2-amino-ethylamino)-propyl]-5-isobutyl-piperazin-1-yl}-3-(2,4-dimethyl-phenyl)-propan-1-one;

(R)-2-Amino-1-{(2R,5S)-4-[(R)-2-amino-3-(2,4-dichloro-phenyl)-propionyl]-5-[4-(2-amino-ethylamino)-butyl]-2-isobutyl-piperazin-1-yl}-3-(2,4-dichloro-phenyl)-propan-1-one;

(R)-2-Amino-1-[(2R,5S)-5-[4-(2-amino-ethylamino)-butyl]-4-((R)-2-amino-3-naphthalen-2-yl-propionyl)-2-isobutyl-piperazin-1-yl]-3-naphthalen-2-yl-propan-1-one;

(R)-2-Amino-1-{(2R,5S)-4-[(R)-2-amino-3-(2,4-dimethyl-phenyl)-propionyl]-5-[4-(2-amino-ethylamino)-butyl]-2-isobutyl-piperazin-1-yl}-3-(2,4-dimethyl-phenyl)-propan-1-one;

(R)-2-Amino-1-{(2R,5S)-4-[(R)-2-amino-3-(3,4-dichloro-phenyl)-propionyl]-5-[4-(2-amino-ethylamino)-butyl]-2-isobutyl-piperazin-1-yl}-3-(3,4-dichloro-phenyl)-propan-1-one;

(R)-2-amino-1-[(2S,5R)-2-[4-(2-amino-ethylamino)-butyl]-4-((R)-2-amino-3-naphtha)en-2-yl-propionyl)-5-cyclohexylmethyl-piperazin-1-yl]-3-naphthalen-2-yl-propan-1-one;

(R)-2-amino-1-{(2S,5R)-4-[(R)-2-amino-3-(2,4-dichloro-phenyl)-propionyl]-2-[4-(2-amino-ethylamino)-butyl]-5-cyclohexylmethyl-piperazin-1-yl}-3-(2,4-dichloro-phenyl)-propan-1-one;

(R)-2-amino-1-{(2R,5S)-4-[(R)-2-amino-3-(2,4-dichloro-phenyl)-propionyl]-5-[3-(2-amino-ethylamino)-propyl]-2-methyl-piperazin-1-yl}-3-(2,4-dichloro-phenyl)-propan-1-one;

(R)-2-amino-1-{(2R,5S)-4-[(R)-2-amino-3-(2,4-dimethyl-phenyl)-propionyl]-5-[3-(2-amino-ethylamino)-propyl]-2-methyl-piperazin-1-yl}-3-(2,4-dimethyl-phenyl)-propan-1-one;

(R)-2-amino-1-[(2R,5S)-5-[3-(2-amino-ethylamino)-propyl]-4-((R)-2-amino-3-naphthalen-2-yl-propionyl)-2-methyl-piperazin-1-yl]-3-naphthalen-2-yl-propan-1-one; or (R)-2-amino-1-{(2R,5S)-4-[(R)-2-amino-3-(3,4-dichloro-phenyl)-propionyl]-5-[3-(2-amino-ethylamino)-propyl]-2-methyl-piperazin-1-yl}-3-(3,4-dichloro-phenyl)-propan-1-one;

or a pharmaceutically acceptable salt thereof.

15. A compound having the formula of structure II:

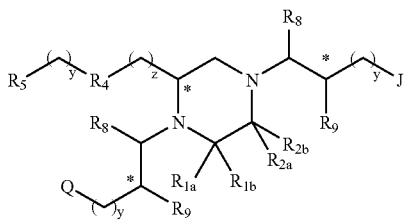

or an enantiomer, stereoisomer or diastereoisomer thereof, or a pharmaceutically acceptable salt thereof,
wherein
J is a ring structure selected from the group consisting of substituted or unsubstituted aromatic carbocyclic rings, substituted or unsubstituted aromatic fused carbobicyclic ring groups, and two substituted or unsubstituted aromatic carbocyclic rings wherein the rings are joined by a bond, —$CH_2$— or —O—, wherein in each instance the ring attached to $L_1$ has 6 ring atoms;
Q is an aromatic carbocyclic ring selected from the group consisting of phenyl, substituted phenyl, naphthyl and substituted naphthyl;
one or two of $R_{1a}$, $R_{1b}$, $R_{2a}$, and $R_{2b}$ are independently a $C_1$ to $C_6$ aliphatic linear or branched chain and the remaining of $R_{1a}$, $R_{1b}$, $R_{2a}$, and $R_{2b}$ are hydrogen, provided that at least one of $R_{1a}$ and $R_{1b}$ and at least one of $R_{2a}$ and $R_{2b}$ are hydrogen;
or one of $R_{1a}$, $R_{1b}$, $R_{2a}$, and $R_{2b}$ are and the remaining of $R_{1a}$, $R_{1b}$, $R_{2a}$, and $R_{2b}$ are hydrogen;
or $R_{1a}$ and $R_{1b}$ together form =O and one of $R_{2a}$ and $R_{2b}$ is a $C_1$ to $C_6$ aliphatic linear or branched chain, and the remaining of $R_{2a}$ and $R_{2b}$ is hydrogen;
$R_4$ is NH or N(—$(CH_2)_y$—$CH_3$);
$R_5$ is $NH_2$, NH—$(CH_2)_y$—$CH_3$, or N(—$(CH_2)_y$—$CH_3$)$_2$;
$R_8$ is in each instance =O;
$R_9$ is in each instance N($R_{10a}$)($R_{10b}$);
$R_{10a}$ and $R_{10b}$ are each independently hydrogen, acetyl, methyl, ethyl, propyl, isopropyl, butyl, pentyl, hexyl, isobutyl, benzyl, pentyl, hexyl, benzoyl, hexanoyl, propionyl, butanoyl, pentanoyl, heptanoyl, cyclopropyl, cyclopropylmethyl, cyclobutyl, cyclobutylmethyl, cyclohexyl, or cyclohexylmethyl;
y is in each instance the index value 1; and
z is an index value from 1 to 6;
wherein the carbon atoms marked with an asterisk can have any stereochemical configuration.

16. A pharmaceutical composition comprising a compound of claim 1 and a pharmaceutically acceptable carrier.

* * * * *

UNITED STATES PATENT AND TRADEMARK OFFICE
CERTIFICATE OF CORRECTION

PATENT NO. : 7,968,548 B2  
APPLICATION NO. : 11/464053  
DATED : June 28, 2011  
INVENTOR(S) : Shubh D. Sharma et al.

Page 1 of 2

It is certified that error appears in the above-identified patent and that said Letters Patent is hereby corrected as shown below:

In the Claims

Claim 2, Column 71, line 34 to line 46, delete the entire second and replace with

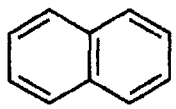 ,

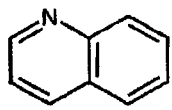 ,

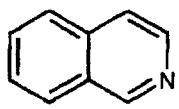 ,

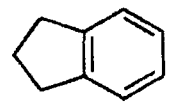 ,

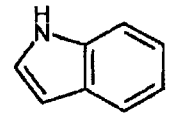 ,

--

Signed and Sealed this
Nineteenth Day of August, 2014

Michelle K. Lee
*Deputy Director of the United States Patent and Trademark Office*

CERTIFICATE OF CORRECTION (continued)

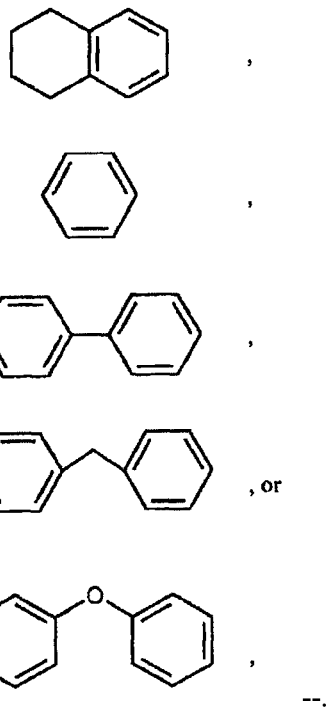

Claim 14, Column 80, line 10 through line 13, delete the section and replace with -- (R)-2-amino-1-{(2R,5S)-4-[(R)-2-amino-3-(2,4-dichloro-phenyl)-propionyl]-5-[3-(2-amino-ethylamino)-propyl]-2-cyclohexylmethyl-piperazin-1-yl}-3-(2,4-dichloro-phenyl)-propan-1-one; --.

Claim 14, Column 80, line 19 through line 20, delete the section and replace with -- (R)-2-amino-1-{(2S,5R)-4-[(R)-2-amino-3-(2,4-dimethyl-phenyl)-propionyl]-2-[3-(2-amino-ethylamino)-propyl]-5-isobutyl-piperazin-1-yl}-3-(2,4-dimethyl-phenyl)-propan-1-one; --.

Claim 14, Column 80, line 41 through line 44, delete the section and replace with -- (R)-2-amino-1-[(2S,5R)-2-[4-(2-amino-ethylamino)-butyl]-4-((R)-2-amino-3-naphthalen-2-yl-propionyl)-5-cyclohexylmethyl-piperazin-1-yl]-3-naphthalen-2-yl-propan-1-one; --.